(12) United States Patent
Langer et al.

(10) Patent No.: US 12,016,901 B2
(45) Date of Patent: Jun. 25, 2024

(54) TISSUE CATALYZED GROWTH OF POLYMER AS EPITHELIAL LININGS FOR THERAPY

(71) Applicants: Massachusetts Institute of Technology, Cambridge, MA (US); The Brigham and Women's Hospital, Inc., Boston, MA (US)

(72) Inventors: Robert S. Langer, Newton, MA (US); Carlo Giovanni Traverso, Newton, MA (US); Junwei Li, Cambridge, MA (US); Thomas Wang, Cambridge, MA (US); Ameya R. Kirtane, Somerville, MA (US); Yunhua Shi, Arlington, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 402 days.

(21) Appl. No.: 17/118,521

(22) Filed: Dec. 10, 2020

(65) Prior Publication Data
US 2021/0177938 A1    Jun. 17, 2021

Related U.S. Application Data

(60) Provisional application No. 63/050,216, filed on Jul. 10, 2020, provisional application No. 63/050,206, filed on Jul. 10, 2020, provisional application No. 62/947,582, filed on Dec. 13, 2019.

(51) Int. Cl.
| | | |
|---|---|---|
| A61K 38/17 | (2006.01) | |
| A61K 31/495 | (2006.01) | |
| A61K 45/06 | (2006.01) | |
| A61L 24/04 | (2006.01) | |
| A61L 24/06 | (2006.01) | |
| A61L 24/08 | (2006.01) | |
| A61L 27/16 | (2006.01) | |
| A61L 27/18 | (2006.01) | |
| A61L 27/20 | (2006.01) | |
| C12N 9/08 | (2006.01) | |

(52) U.S. Cl.
CPC ........ *A61K 38/1787* (2013.01); *A61K 31/495* (2013.01); *A61K 45/06* (2013.01); *A61L 24/046* (2013.01); *A61L 24/06* (2013.01); *A61L 24/08* (2013.01); *A61L 27/16* (2013.01); *A61L 27/18* (2013.01); *A61L 27/20* (2013.01); *C12N 9/0065* (2013.01); *A61L 2300/254* (2013.01); *A61L 2300/256* (2013.01); *A61L 2300/438* (2013.01); *A61L 2400/04* (2013.01); *A61L 2430/06* (2013.01); *A61L 2430/16* (2013.01); *C12Y 111/01006* (2013.01)

(58) Field of Classification Search
None
See application file for complete search history.

(56) References Cited

U.S. PATENT DOCUMENTS

| | | |
|---|---|---|
| 7,025,791 B2 | 4/2006 | Levine et al. |
| 7,335,210 B2 | 2/2008 | Smit |
| 8,110,208 B1 | 2/2012 | Hen |
| 8,414,559 B2 | 4/2013 | Gross |
| 9,707,070 B2 | 7/2017 | Gittard et al. |
| 9,833,541 B2 | 12/2017 | McCoy et al. |
| 2009/0232876 A1 | 9/2009 | Montes et al. |
| 2010/0129427 A1 | 5/2010 | Hen et al. |
| 2014/0205636 A1 | 7/2014 | Khatri |
| 2017/0232141 A1 | 8/2017 | Surti et al. |
| 2023/0101687 A1 | 3/2023 | Traverso et al. |

FOREIGN PATENT DOCUMENTS

| | | |
|---|---|---|
| CN | 102302796 A | 1/2012 |
| CN | 103561726 A | 2/2014 |
| CN | 104491910 A | 4/2015 |
| GB | 2554101 A | 3/2018 |
| JP | 2006-528975 A | 12/2006 |
| WO | WO 2010/077301 A1 | 7/2010 |
| WO | WO 2013/025685 A1 | 2/2013 |
| WO | WO 2015/021375 A1 | 2/2015 |
| WO | WO 2018/052951 A1 | 3/2018 |
| WO | WO 2018/081757 A1 | 5/2018 |

OTHER PUBLICATIONS

In Vivo vs. In Vitro: What Does It All Mean? Healthline, 2013, pp. 1-41 (Year: 2013).*
Kim et al. Oxygen Concentration Control of Dopamine-Induced High Uniformity Surface Coating Chemistry. ACS Appl Mater Interfaces. Jan. 23, 2013;5(2):233-8.*
Abuhelwa et al., A Quantitative Review and Meta-Models of the Variability and Factors Affecting Oral Drug Absorption-Part I: Gastrointestinal pH. AAPS J. Sep. 2016; 18(5):1309-1321. doi: 10.1208/s12248-016-9952-8. Epub Aug. 5, 2016.
Andrews et al., Comparison of endoscopic, necropsy and histology scoring of equine gastric ulcers. Equine Vet J. Jul. 2002;34(5):475-8. doi: 10.2746/042516402776117827.
Ball et al., Kinetics of polydopamine film deposition as a function of pH and dopamine concentration: insights in the polydopamine deposition mechanism. J Colloid Interface Sci. Nov. 15, 2012;386(1):366-72. doi: 10.1016/j.jcis.2012.07.030. Epub Jul. 20, 2012.

(Continued)

*Primary Examiner* — Maury A Audet
(74) *Attorney, Agent, or Firm* — Wolf, Greenfield & Sacks, P.C.

(57) ABSTRACT

The present disclosure provides compositions, methods, and kits that enable the in situ growth of polymers on or within a subject. In some aspects, the monomer, dopamine, polymerizes in vivo to form a polymer on a tissue. In additional aspects, the compositions, methods, and kits are useful for treating or preventing a disease or disorder.

15 Claims, 37 Drawing Sheets

(56) References Cited

OTHER PUBLICATIONS

Figure 1A:
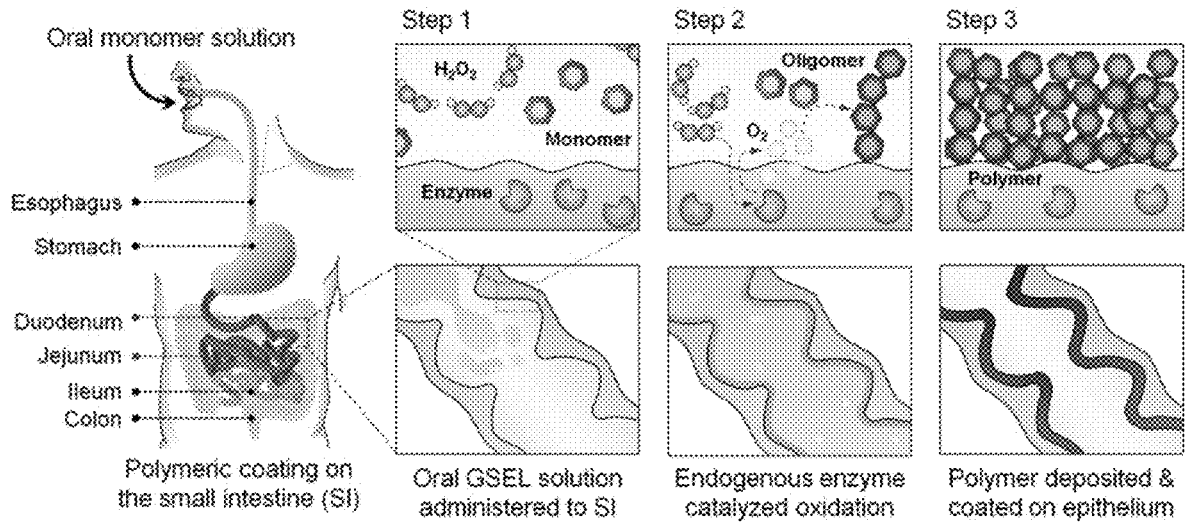

Barkun et al., Topical hemostatic agents: a systematic review with particular emphasis on endoscopic application in GI bleeding. Gastrointest Endosc. May 2013;77(5):692-700. doi: 10.1016/j.gie.2013.01.020.
Candi et al., The cornified envelope: a model of cell death in the skin. Nat Rev Mol Cell Biol. Apr. 2005;6(4):328-40. doi: 10.1038/nrm1619.
Carino et al., Oral insulin delivery. Adv Drug Deliv Rev. Feb. 1, 1999;35(2-3):249-257. doi: 10.1016/s0169-409x(98)00075-1.
Chahal et al., High rate of re-bleeding after application of Hemospray for upper and lower gastrointestinal bleeds. Dig Liver Dis. Jul. 2020;52(7):768-772. doi: 10.1016/j.dld.2020.01.009. Epub Feb. 29, 2020.
Connock et al., Catalase particles in the epithelial cells of the guinea-pig small intestine. Histochem J. Sep. 1970;2(5):371-80. doi: 10.1007/BF01004718.
Cui et al., Monodisperse Polymer Capsules: Tailoring Size, Shell Thickness, and Hydrophobic Cargo Loading via Emulsion Templating. Adv Funct Mater. May 25, 2010;20(10):1625-31. doi: 10.1002/adfm.201000209.
Doenhoff et al., Praziquantel: mechanisms of action, resistance and new derivatives for schistosomiasis. Curr Opin Infect Dis. Dec. 2008;21(6):659-67. doi: 10.1097/QCO.0b013e328318978f.
Dressman et al., Pharmaceutical Dissolution Testing. 1st Edition. Jul. 2005. CRC Press, Boca Raton, FL. 429 pages.
Forrest et al., Endoscopy in gastrointestinal bleeding. Lancet. Aug. 17, 1974;2(7877):394-7. doi: 10.1016/s0140-6736(74)91770-x.
Gallico et al., Permanent coverage of large burn wounds with autologous cultured human epithelium. N Engl J Med. Aug. 16, 1984;311(7):448-51. doi: 10.1056/NEJM198408163110706.
Godin et al., Species-related variations in tissue antioxidant status—I. Differences in antioxidant enzyme profiles. Comp Biochem Physiol B. Nov. 1992;103(3):737-42. doi: 10.1016/0305-0491(92)90399-c.
Green et al., Celiac disease. N Engl J Med. Oct. 25, 2007;357(17):1731-43. doi: 10.1056/NEJMra071600.
Harris, F.C., Pyloric stenosis: hold-up of enteric coated aspirin tablets. Br J Surg. Dec. 1973;60(12):979-81. doi: 10.1002/bjs.1800601217.
Khan et al., A pH-dependent colon targeted oral drug delivery system using methacrylic acid copolymers. I. Manipulation of drug release using Eudragit L100-55 and Eudragit S100 combinations. J Control Release. Mar. 29, 1999;58(2):215-22. doi: 10.1016/s0168-3659(98)00151-5.
Kirkegaard et al., Experimental nonsuture colonic anastomoses. Am J Surg. Feb. 1980;139(2):233-6. doi: 10.1016/0002-9610(80)90261-5.
Kirkman et al., Mammalian catalase: a venerable enzyme with new mysteries. Trends Biochem Sci. Jan. 2007;32(1):44-50. doi: 10.1016/j.tibs.2006.11.003. Epub Dec. 8, 2006.
Kirtane et al., A once-a-month oral contraceptive. Sci Transl Med. Dec. 4, 2019;11(521):eaay2602. doi: 10.1126/scitranslmed.aay2602.
Lambrecht et al., The airway epithelium in asthma. Nat Med. May 4, 2012;18(5):684-92. doi: 10.1038/nm.2737.
Lanas et al., Non-variceal upper gastrointestinal bleeding. Nat Rev Dis Primers. Apr. 19, 2018;4:18020. doi: 10.1038/nrdp.2018.20.
Laulicht et al., Diuretic bioactivity optimization of furosemide in rats. Eur J Pharm Biopharm. Oct. 2011;79(2):314-9. doi: 10.1016/j.ejpb.2011.04.014. Epub May 5, 2011.
Lee et al., Therapeutic luminal coating of the intestine. Nat Mater. Sep. 2018;17(9):834-842. doi: 10.1038/s41563-018-0106-5. Epub Jun. 11, 2018.
Patel et al., EndoBarrier®: a Safe and Effective Novel Treatment for Obesity and Type 2 Diabetes? Obes Surg. Jul. 2018;28(7):1980-1989. doi: 10.1007/s11695-018-3123-1.
Nahon et al., Epidemiological and prognostic factors involved in upper gastrointestinal bleeding: results of a French prospective multicenter study. Endoscopy. Nov. 2012;44(11):998-1008. doi: 10.1055/s-0032-1310006. Epub Oct. 29, 2012.
Ofikwu et al., EVICEL glue-induced small bowel obstruction after laparoscopic gastric bypass. Surg Laparosc Endosc Percutan Tech. Feb. 2013;23(1):e38-40. doi: 10.1097/SLE.0b013e318275b2cb.
Peterson et al., Intestinal epithelial cells: regulators of barrier function and immune homeostasis. Nat Rev Immunol. Mar. 2014;14(3):141-53. doi: 10.1038/nri3608.
Ponzio et al., Robust Alginate-Catechol@Polydopamine Free-Standing Membranes Obtained from the Water/Air Interface. Langmuir. Mar. 7, 2017;33(9):2420-2426. doi: 10.1021/acs.langmuir.6b04435. Epub Feb. 22, 2017.
Sonis, S.T., The pathobiology of mucositis. Nat Rev Cancer. Apr. 2004;4(4):277-84. doi: 10.1038/nrc1318.
Squier et al., Human Oral Mucosa: Development, Structure and Function. Dec. 2010. Wiley-Blackwell.
Sun et al., Inhibition of autophagy ameliorates acute lung injury caused by avian influenza A H5N1 infection. Sci Signal. Feb. 21, 2012;5(212):ra16. doi: 10.1126/scisignal.2001931.
Taboada et al., Overcoming the translational barriers of tissue adhesives. Nat Rev Mater. Feb. 27, 2020;5(4):310-29. doi: 10.1038/s41578-019-0171-7.
Thakral et al., Eudragit: a technology evaluation. Expert Opin Drug Deliv. Jan. 2013;10(1):131-49. doi: 10.1517/17425247.2013.736962. Epub Oct. 26, 2012.
Van Leerdam et al., Acute upper GI bleeding: did anything change? Time trend analysis of incidence and outcome of acute upper GI bleeding between 1993/1994 and 2000. Am J Gastroenterol. Jul. 2003;98(7):1494-9. doi: 10.1111/j.1572-0241.2003.07517.x.
Xu et al., Bioadhesive hydrogels demonstrating pH-independent and ultrafast gelation promote gastric ulcer healing in pigs. Sci Transl Med. Aug. 26, 2020;12(558):eaba8014. doi: 10.1126/scitranslmed.aba8014.
Yui et al., Functional engraftment of colon epithelium expanded in vitro from a single adult Lgr5+ stem cell. Nat Med. Mar. 11, 2012;18(4):618-23. doi: 10.1038/nm.2695.
Yuk et al., Dry double-sided tape for adhesion of wet tissues and devices. Nature. Nov. 2019;575(7781):169-174. doi: 10.1038/s41586-019-1710-5. Epub Oct. 30, 2019.
Zelikin et al., Materials and methods for delivery of biological drugs. Nat Chem. Oct. 21, 2016;8(11):997-1007. doi: 10.1038/nchem.2629.
Zhan et al., A new targeted delivery approach by functionalizing drug nanocrystals through polydopamine coating. Eur J Pharm Biopharm. May 2017;114:221-229. doi: 10.1016/j.ejpb.2017.01.020. Epub Feb. 1, 2017.
Zihni et al., Tight junctions: from simple barriers to multifunctional molecular gates. Nat Rev Mol Cell Biol. Sep. 2016;17(9):564-80. doi: 10.1038/nrm.2016.80. Epub Jun. 29, 2016.
Kim et al., Oxygen concentration control of dopamine-induced high uniformity surface coating chemistry. ACS Appl Mater Interfaces. Jan. 23, 2013;5(2):233-8. doi: 10.1021/am302439g. Epub Jan. 3, 2013.
Zavada et al., Radical-Mediated Enzymatic Polymerizations. Int. J. Mol. Sci. 2016;17:195. https://doi.org/10.3390/ijms17020195.
International Search Report and Written Opinion dated Apr. 12, 2021 for International Application No. PCT/US2020/064364.
International Preliminary Report on Patentability dated Jun. 23, 2022 for International Application No. PCT/US2020/064364.
International Search Report and Written Opinion dated Apr. 12, 2021 for International Application No. PCT/US2020/064368.
International Preliminary Report on Patentability dated Jun. 23, 2022 for International Application No. PCT/US2020/064368.
[No Author Listed], 2. Classification and Diagnosis of Diabetes: Standards of Medical Care in Diabetes-2018. Diabetes Care. Jan. 2018;41(Suppl 1):S13-S27. doi: 10.2337/dc18-S002.
[No Author Listed], Maxidex® (dexamethasone ophthalmic suspension) Label. Alcon Laboratories, Inc. Jul. 2022. 6 pages.
[No Author Listed], Oral Health Care Drug Products for Over-the-Counter Human Use; Antigingivitis/Antiplaque Drug Products; Establishment of a Monograph; Proposed Rules. Department of

(56) References Cited

OTHER PUBLICATIONS

Health and Human Services, Food and Drug Administration. Federal Register. May 29, 2003;68(103):32232-87. 57 pages.
[No Author Listed], Test No. 407: Repeated Dose 28-day Oral Toxicity Study in Rodents. OECD Guidelines for the Testing of Chemicals. Oct. 3, 2008. Section 4. OECD Publishing. 13 pages. doi: 10.1787/9789264070684-en.
Abramson et al., A luminal unfolding microneedle injector for oral delivery of macromolecules. Nat Med. Oct. 2019;25(10):1512-1518. doi: 10.1038/s41591-019-0598-9. Epub Oct. 7, 2019.
Anselmo et al., Non-invasive delivery strategies for biologics. Nat Rev Drug Discov. Jan. 2019;18(1):19-40. doi: 10.1038/nrd.2018. 183. Epub Nov. 30, 2018.
Arakawa et al., Quality of ulcer healing in gastrointestinal tract: its pathophysiology and clinical relevance. World J Gastroenterol. Sep. 21, 2012;18(35):4811-22. doi: 10.3748/wjg.v18.i35.4811.
Azari et al., Conjunctivitis: a systematic review of diagnosis and treatment. JAMA. Oct. 23, 2013;310(16):1721-9. doi: 10.1001/jama. 2013.280318. Erratum in: JAMA. Jan. 1, 2014;311(1):95. Dosage error in article text.
Babaee et al., Temperature-responsive biometamaterials for gastrointestinal applications. Sci Transl Med. Apr. 17, 2019;11(488):eaau8581. doi: 10.1126/scitranslmed.aau8581.
Barker, N., Adult intestinal stem cells: critical drivers of epithelial homeostasis and regeneration. Nat Rev Mol Cell Biol. Jan. 2014;15(1):19-33. doi: 10.1038/nrm3721. Epub Dec. 11, 2013.
Bellinger et al., Oral, ultra-long-lasting drug delivery: Application toward malaria elimination goals. Sci Transl Med. Nov. 16, 2016;8(365):365ra157. doi: 10.1126/scitranslmed.aag2374.
Bisaglia et al., Kinetic and structural analysis of the early oxidation products of dopamine: analysis of the interactions with alpha-synuclein. J Biol Chem. May 25, 2007;282(21):15597-605. doi: 10.1074/jbc.M610893200. Epub Mar. 29, 2007.
Camaschella, C., Iron-deficiency anemia. N Engl J Med. May 7, 2015;372(19):1832-43. doi: 10.1056/NEJMra1401038.
Elloumi-Hannachi et al., Cell sheet engineering: a unique nanotechnology for scaffold-free tissue reconstruction with clinical applications in regenerative medicine. J Intern Med. Jan. 2010;267(1):54-70. doi: 10.1111/j.1365-2796.2009.02185.x.
Fagerberg et al., Analysis of the human tissue-specific expression by genome-wide integration of transcriptomics and antibody-based proteomics. Mol Cell Proteomics. Feb. 2014;13(2):397-406. doi: 10.1074/mcp.M113.035600. Epub Dec. 5, 2013.
Fishbein, T.M., Intestinal transplantation. N Engl J Med. Sep. 3, 2009;361(10):998-1008. doi: 10.1056/NEJMra0804605. Erratum in: N Engl J Med. Oct. 1, 2009;361(14):1416.
Forooshani et al., Recent approaches in designing bioadhesive materials inspired by mussel adhesive protein. J Polym Sci A Polym Chem. Jan. 1, 2017;55(1):9-33. doi: 10.1002/pola.28368. Epub Oct. 11, 2016.
Freedman et al., Biomaterials to Mimic and Heal Connective Tissues. Adv Mater. May 2019;31(19):e1806695. doi: 10.1002/adma.201806695. Epub Mar. 25, 2019.
Gerber et al., Recent advances in radiation therapy. Am Fam Physician. Dec. 1, 2008;78(11):1254-62.
Gipson, I.K., Goblet cells of the conjunctiva: A review of recent findings. Prog Retin Eye Res. Sep. 2016;54:49-63. doi: 10.1016/j.preteyeres.2016.04.005. Epub Apr. 16, 2016.
Goyal et al., Human catalase: looking for complete identity. Protein Cell. Oct. 2010;1(10):888-97. doi: 10.1007/s13238-010-0113-z. Epub Nov. 9, 2010.
Gralnek et al., Management of acute bleeding from a peptic ulcer. N Engl J Med. Aug. 28, 2008;359(9):928-37. doi: 10.1056/NEJMra0706113.
Heber et al., Endocrine and nutritional management of the post-bariatric surgery patient: an Endocrine Society Clinical Practice Guideline. J Clin Endocrinol Metab. Nov. 2010;95(11):4823-43. doi: 10.1210/jc.2009-2128. Erratum in: J Clin Endocrinol Metab. May 1, 20213;106(6):e2459.

Holmes et al., Direct cardiac effects of dopamine. Circ Res. Jan. 1962; 10:68-72. doi: 10.1161/01.res.10.1.68.
Hong et al., Progressive fuzzy cation-π assembly of biological catecholamines. Sci Adv. Sep. 7, 2018;4(9):eaat7457. doi: 10.1126/sciadv.aat7457.
Kersey et al., Corticosteroid-induced glaucoma: a review of the literature. Eye (Lond). Apr. 2006;20(4):407-16. doi: 10.1038/sj.eye. 6701895.
Khademhosseini et al., A decade of progress in tissue engineering. Nat Protoc. Oct. 2016;11(10):1775-81. doi: 10.1038/nprot.2016. 123. Epub Sep. 1, 2016.
Kitano et al., Bioengineering of functional human induced pluripotent stem cell-derived intestinal grafts. Nat Commun. Oct. 10, 2017;8(1):765. doi: 10.1038/s41467-017-00779-y.
Laine, L., Upper Gastrointestinal Bleeding Due to a Peptic Ulcer. N Engl J Med. Jun. 16, 2016;374(24):2367-76. doi: 10.1056/NEJMcp1514257.
Lavker et al., Epithelial stem cells: the eye provides a vision. Eye (Lond). Nov. 2003;17(8):937-42. doi: 10.1038/sj.eye.6700575.
Leader et al., Protein therapeutics: a summary and pharmacological classification. Nat Rev Drug Discov. Jan. 2008;7(1):21-39. doi: 10.1038/nrd2399.
Lee et al., Facile Conjugation of Biomolecules onto Surfaces via Mussel Adhesive Protein Inspired Coatings. Adv Mater. Jan. 26, 2009;21(4):431-434. doi: 10.1002/adma.200801222.
Lee et al., In Situ Self-Cross-Linkable, Long-Term Stable Hyaluronic Acid Filler by Gallol Autoxidation for Tissue Augmentation and Wrinkle Correction. Chem Mater. Nov. 21, 2019;31(23):9614-24. doi: 10.1021/acs.chemmater.9b02802.
Lee et al., Mussel-inspired surface chemistry for multifunctional coatings. Science. Oct. 19, 2007;318(5849):426-30. doi: 10.1126/science.1147241.
Li et al., Dramatic enhancement of the detection limits of bioassays via ultrafast deposition of polydopamine. Nat Biomed Eng. 2017;1:0082. doi: 10.1038/s41551-017-0082. Epub Jun. 5, 2017.
Li et al., Gastrointestinal synthetic epithelial linings. Sci Transl Med. Aug. 26, 2020;12(558):eabc0441. doi: 10.1126/scitranslmed. abc0441.
Lin et al., Treatment of diabetic gastroparesis by high-frequency gastric electrical stimulation. Diabetes Care. May 2004;27(5):1071-6. doi: 10.2337/diacare.27.5.1071.
Liu et al., Triggerable tough hydrogels for gastric resident dosage forms. Nat Commun. Jul. 25, 2017;8(1):124. doi: 10.1038/s41467-017-00144-z.
Lomer et al., Review article: lactose intolerance in clinical practice—myths and realities. Aliment Pharmacol Ther. Jan. 15, 2008;27(2):93-103. doi: 10.1111/j.1365-2036.2007.03557.x. Epub Oct. 23, 2007.
Maier et al., Adaptive synergy between catechol and lysine promotes wet adhesion by surface salt displacement. Science. Aug. 7, 2015;349(6248):628-32. doi: 10.1126/science.aab0556.
Manell et al., Establishment of a Refined Oral Glucose Tolerance Test in Pigs, and Assessment of Insulin, Glucagon and Glucagon-Like Peptide-1 Responses. PLoS One. Feb. 9, 2016;11(2):e0148896. doi: 10.1371/journal.pone.0148896.
Margoliash et al., A study of the inhibition of catalase by 3-amino-1:2:4:-triazole. Biochem J. Mar. 1958;68(3):468-75. doi: 10.1042/bj0680468.
Mingrone et al., Bariatric surgery versus conventional medical therapy for type 2 diabetes. N Engl J Med. Apr. 26, 2012;366(17):1577-85. doi: 10.1056/NEJMoa1200111. Epub Mar. 26, 2012.
Nishida et al., Corneal reconstruction with tissue-engineered cell sheets composed of autologous oral mucosal epithelium. N Engl J Med. Sep. 16, 2004;351(12):1187-96. doi: 10.1056/NEJMoa040455.
Obermeier et al., Development, maintenance and disruption of the blood-brain barrier. Nat Med. Dec. 2013;19(12):1584-96. doi: 10.1038/nm.3407. Epub Dec. 5, 2013.
Odenwald et al., The intestinal epithelial barrier: a therapeutic target? Nat Rev Gastroenterol Hepatol. Jan. 2017;14(1):9-21. doi: 10.1038/nrgastro.2016.169. Epub Nov. 16, 2016.
Park et al., Polydopamine-based simple and versatile surface modification of polymeric nano drug carriers. ACS Nano. Apr. 22, 2014;8(4):3347-56. doi: 10.1021/nn405809c. Epub Mar. 19, 2014.

(56) References Cited

OTHER PUBLICATIONS

Rajagopalan et al., Endoscopic Duodenal Mucosal Resurfacing for the Treatment of Type 2 Diabetes: 6-Month Interim Analysis From the First-in-Human Proof-of-Concept Study. Diabetes Care. Dec. 2016;39(12):2254-2261. doi: 10.2337/dc16-0383. Epub Aug. 12, 2016.

Richard et al., Influenza A viruses are transmitted via the air from the nasal respiratory epithelium of ferrets. Nat Commun. Feb. 7, 2020;11(1):766. doi: 10.1038/s41467-020-14626-0.

Rosado et al., Enzyme replacement therapy for primary adult lactase deficiency. Effective reduction of lactose malabsorption and milk intolerance by direct addition of beta-galactosidase to milk at mealtime. Gastroenterology. Nov. 1984;87(5):1072-82.

Scully, C., Aphthous ulceration. N Engl J Med. Jul. 13, 2006;355(2):165-72. doi: 10.1056/NEJMcp054630.

Storhaug et al., Country, regional, and global estimates for lactose malabsorption in adults: a systematic review and meta-analysis. Lancet Gastroenterol Hepatol. Oct. 2017;2(10):738-746. doi: 10.1016/S2468-1253(17)30154-1. Epub Jul. 7, 2017.

Sweeney et al., Blood-brain barrier breakdown in Alzheimer disease and other neurodegenerative disorders. Nat Rev Neurol. Mar. 2018;14(3):133-150. doi: 10.1038/nrneurol.2017.188. Epub Jan. 29, 2018.

Sáenz et al., Acid and the basis for cellular plasticity and reprogramming in gastric repair and cancer. Nat Rev Gastroenterol Hepatol. May 2018;15(5):257-273. doi: 10.1038/nrgastro.2018.5. Epub Feb. 21, 2018.

Thelen et al., Cytochrome P450-mediated metabolism in the human gut wall. J Pharm Pharmacol. May 2009;61(5):541-58. doi: 10.1211/jpp/61.05.0002.

Thi et al., Engineered horseradish peroxidase-catalyzed hydrogels with high tissue adhesiveness for biomedical applications. J Ind Eng Chem. Oct. 25, 2019;78:34-52. doi: 10.1016/j.jiec.2019.05.026.

Tokura et al., Fabrication of Defined Polydopamine Nanostructures by DNA Origami-Templated Polymerization. Angew Chem Int Ed Engl. Feb. 5, 2018;57(6):1587-1591. doi: 10.1002/anie.201711560. Epub Jan. 15, 2018.

Torres et al., Crohn's disease. Lancet. Apr. 29, 2017;389(10080):1741-1755. doi: 10.1016/S0140-6736(16)31711-1. Epub Dec. 1, 2016.

Traverso et al., Perspective: Special delivery for the gut. Nature. Mar. 26, 2015;519(7544):S19. doi: 10.1038/519S19a.

Turner, J.R., Intestinal mucosal barrier function in health and disease. Nat Rev Immunol. Nov. 2009;9(11):799-809. doi: 10.1038/nri2653.

Vacanti et al., Tissue engineering: the design and fabrication of living replacement devices for surgical reconstruction and transplantation. Lancet. Jul. 1999;354 Suppl 1:SI32-4. doi: 10.1016/s0140-6736(99)90247-7.

Vale et al., Praziquantel for Schistosomiasis: Single-Drug Metabolism Revisited, Mode of Action, and Resistance. Antimicrob Agents Chemother. Apr. 24, 2017;61(5):e02582-16. doi: 10.1128/AAC.02582-16.

Varga et al., Endothelial cell infection and endotheliitis in COVID-19. Lancet. May 2, 2020;395(10234):1417-1418. doi: 10.1016/S0140-6736(20)30937-5. Epub Apr. 21, 2020.

Vera-Llonch et al., Oral mucositis in patients undergoing radiation treatment for head and neck carcinoma. Cancer. Jan. 15, 2006;106(2):329-36. doi: 10.1002/cncr.21622.

Winterwerber et al., Photocontrolled Dopamine Polymerization on DNA Origami with Nanometer Resolution. Angew Chem Int Ed Engl. Apr. 6, 2020;59(15):6144-6149. doi: 10.1002/anie.201911249. Epub Dec. 27, 2019.

\* cited by examiner

FIG. 2A
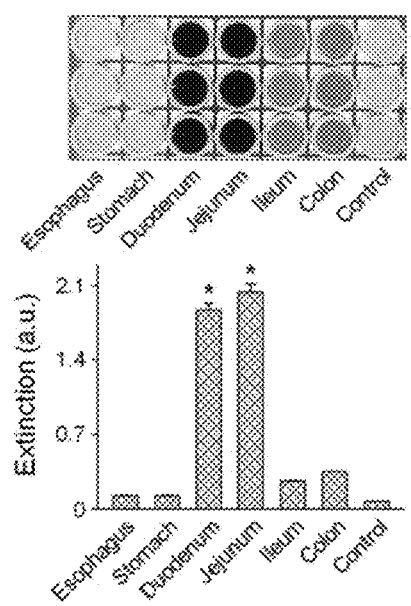
FIG. 2B
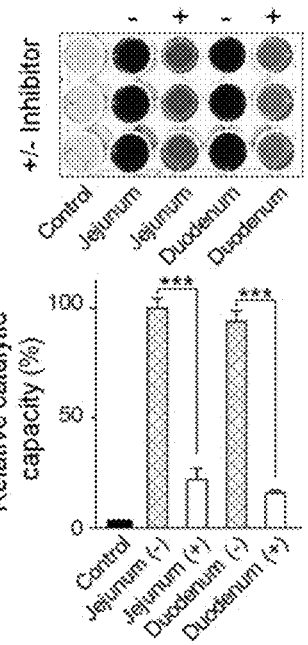
FIG. 2C
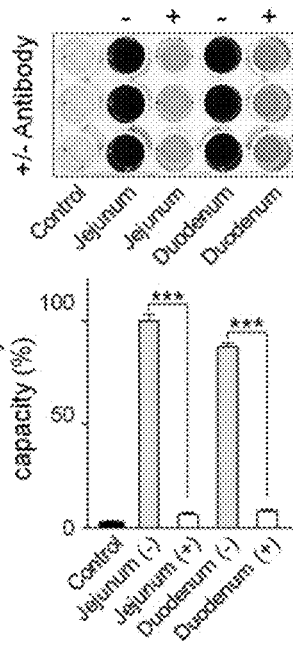
FIG. 2D
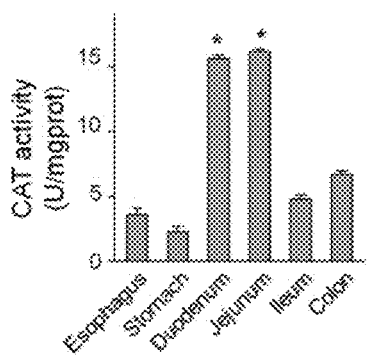
FIG. 2E
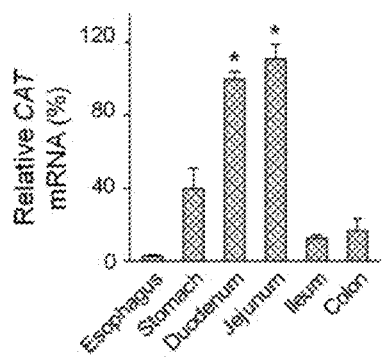
FIG. 2F
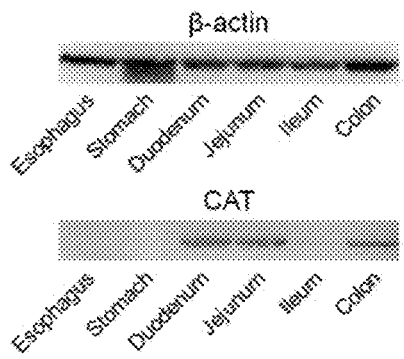
FIG. 2G Without staining
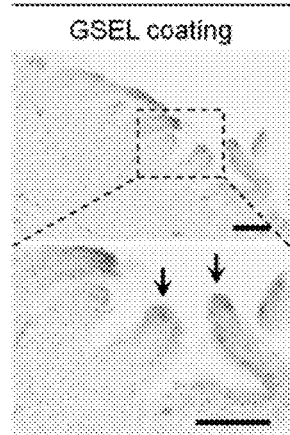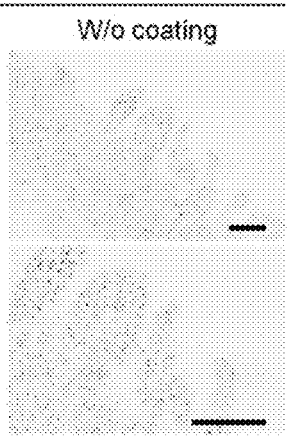
FIG. 2H Specific staining
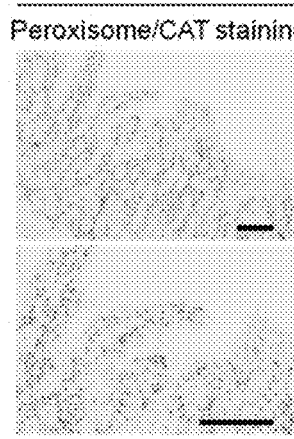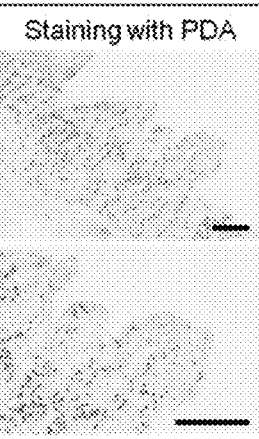

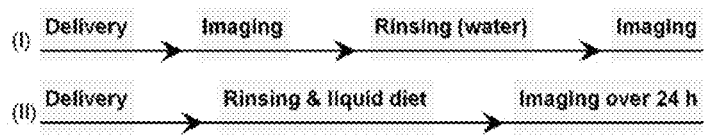

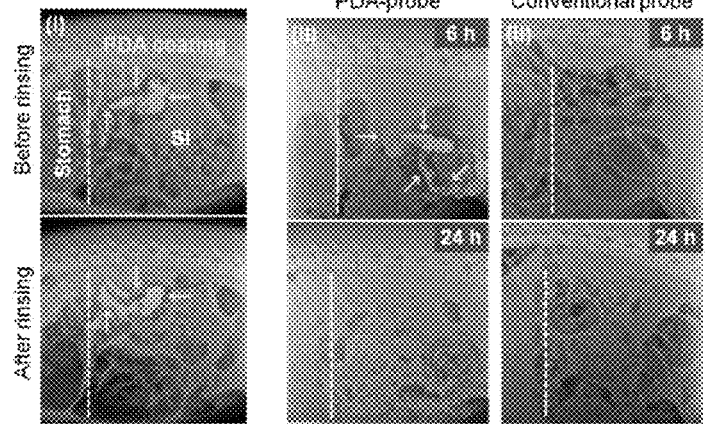

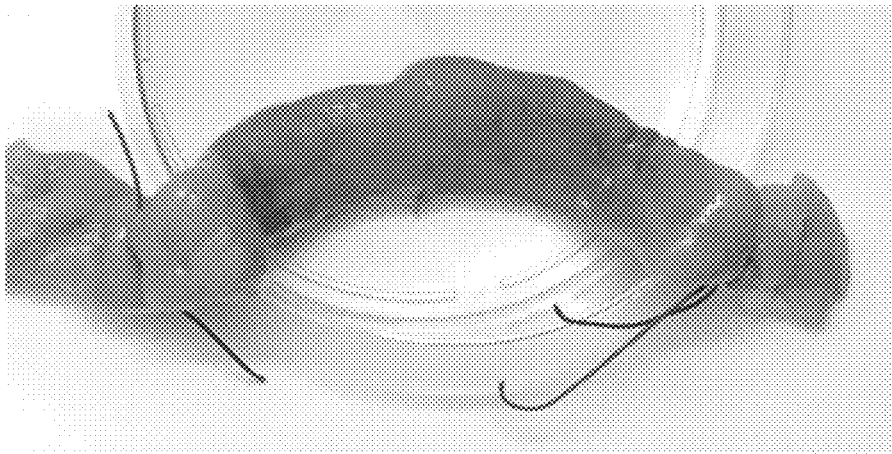
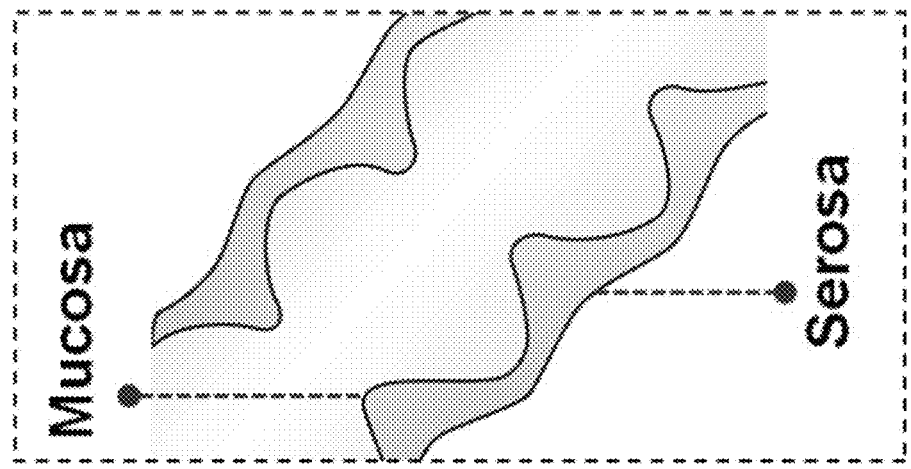
FIG. 9

5 min
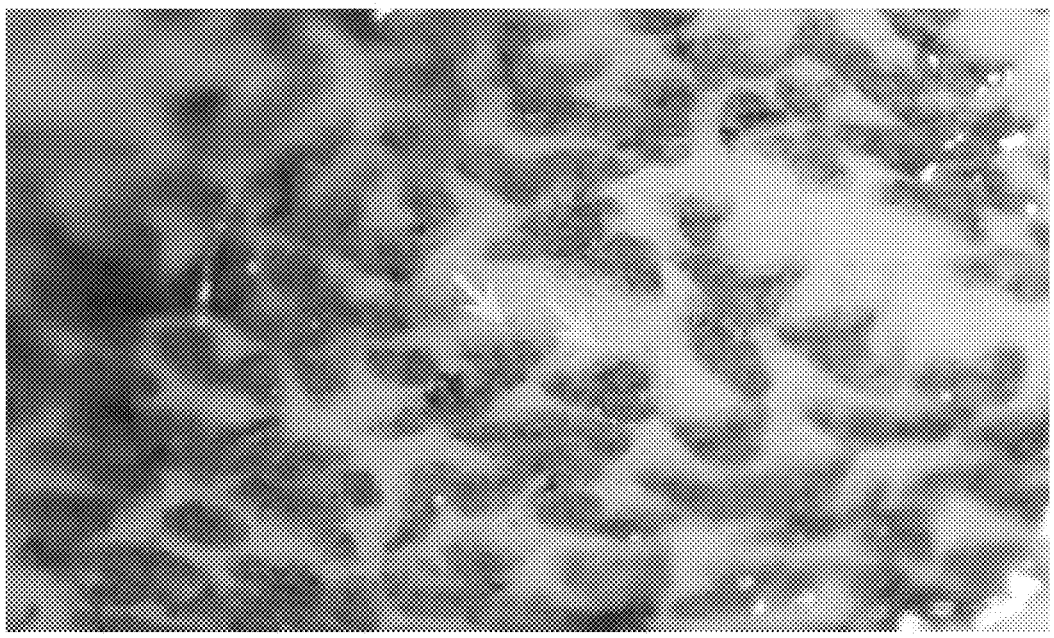
15 min
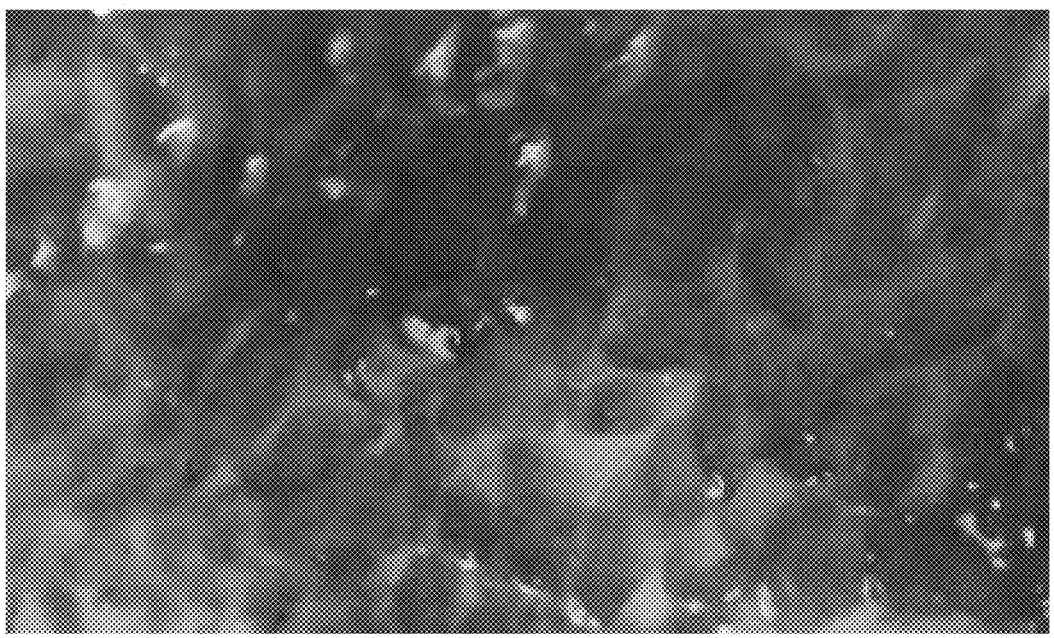
FIG. 13

Hematological results (mean ± s.d.)

| | Control | PDA | GSEL soln. |
|---|---|---|---|
| WBC | 10.52 ± 2.75 | 7.35 ± 1.50 | 10.29 ± 4.01 |
| NEU | 21.71 ± 4.72 | 26.70 ± 3.65 | 21.08 ± 2.38 |
| LYM | 72.75 ± 5.24 | 67.71 ± 5.34 | 74.06 ± 3.58 |
| MON | 4.89 ± 0.73 | 5.06 ± 2.25 | 4.11 ± 1.42 |
| EOS | 0.50 ± 0.19 | 0.38 ± 0.16 | 0.66 ± 0.50 |
| BAS | 0.15 ± 0.19 | 0.15 ± 0.03 | 0.09 ± 0.06 |
| RBC | 7.46 ± 0.22 | 7.30 ± 0.43 | 7.25 ± 0.13 |
| HB | 16.75 ± 0.91 | 16.08 ± 1.07 | 15.73 ± 0.30 |
| HCT | 43.00 ± 1.61 | 41.30 ± 2.52 | 40.65 ± 0.78 |
| MCV | 57.63 ± 1.93 | 56.60 ± 0.14 | 56.08 ± 1.99 |
| MCH | 22.45 ± 0.91 | 22.00 ± 0.24 | 21.70 ± 0.45 |
| MCHC | 38.95 ± 0.76 | 38.93 ± 0.33 | 38.70 ± 0.88 |
| RDW | 14.60 ± 0.20 | 14.90 ± 0.20 | 14.85 ± 0.44 |
| MPV | 6.75 ± 0.26 | 7.33 ± 0.64 | 7.00 ± 0.45 |

Note. *WBC* (K/μL), white blood cells; *NEU* (%), neutrophils; *LYM* (%), lymphocytes; *MON* (%), monocytes; *EOS* (%), eosinophils; *BAS* (%), basophils; *RBC* (M/μL), red blood cells; *HB* (g/dL), hemoglobin; *HCT*(%), hematocrits; *MCV* (fl), mean corpuscular volume; *MCH* (pg), mean corpuscular hemoglobin; *MCHC* (g/dL), mean corpuscular hemoglobin concentration; *RDW* (%), red cell distribution width; *MPV* (fl), mean platelet volume.

FIG. 21

| Blood biochemistry results (mean ± s.d.) | | | |
|---|---|---|---|
| | Control | PDA | GSEL soln. |
| AST | 73.25 ± 2.63 | 87.25 ± 10.34 | 79.25 ± 9.74 |
| GGT | 0.50 ± 0.58 | 1.00 ± 0.00 | 0.25 ± 0.50 |
| ALB | 3.23 ± 0.17 | 3.55 ± 0.10 | 3.43 ± 0.19 |
| TBIL | 0.20 ± 0.00 | 0.25 ± 0.06 | 0.20 ± 0.00 |
| CRE | 0.68 ± 0.15 | 0.83 ± 0.30 | 0.70 ± 0.08 |
| CHO | 57.50 ± 9.75 | 68.25 ± 9.71 | 61.50 ± 7.85 |
| GLU | 223.50 ± 53.97 | 198.00 ± 18.02 | 212.00 ± 49.96 |
| P | 7.73 ± 0.67 | 8.28 ± 1.38 | 7.83 ± 0.33 |
| Cl | 100.25 ± 1.71 | 100.25 ± 1.71 | 99.75 ± 2.22 |
| K | 8.38 ± 1.16 | 9.60 ± 2.64 | 8.23 ± 0.49 |
| Na | 138.00 ± 2.16 | 138.25 ± 2.22 | 138.50 ± 3.11 |

Note. AST (IU/L), aspartate aminotransferase; GGT (IU/L), gamma glutamyl transferase; ALB (g/dL), albumin; TBIL (mg/dL), total bilirubin; CRE (mg/dL), creatinine; CHO (mg/dL), cholesterol; GLU (mg/dL), glucose; P (mg/dL), phosphorus; Cl (mEq/L), chloride; K (mEq/L), potassium; Na (mEq/L), sodium.

FIG. 22

FIG. 36A Gentle scratching with finger
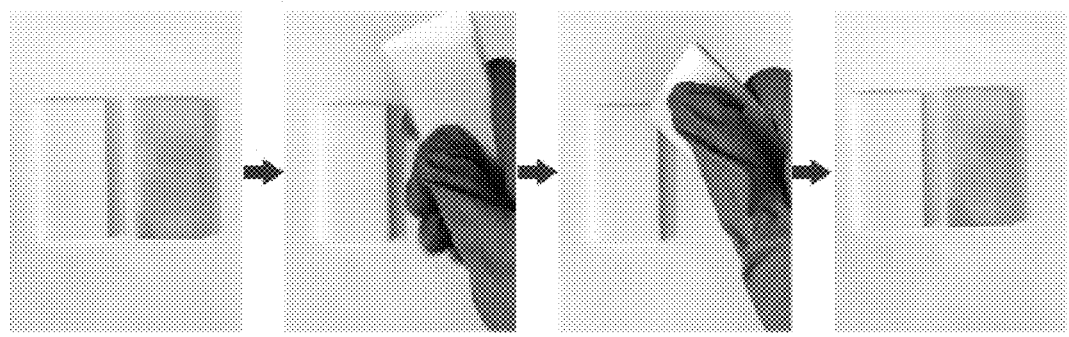
FIG. 36B Vigorous scratching with spine of a scalpel
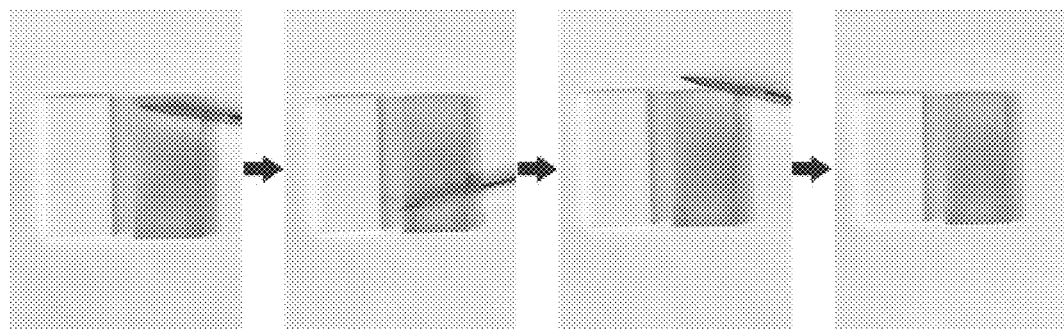
FIG. 36C Extremely vigorous scratching with sandpaper
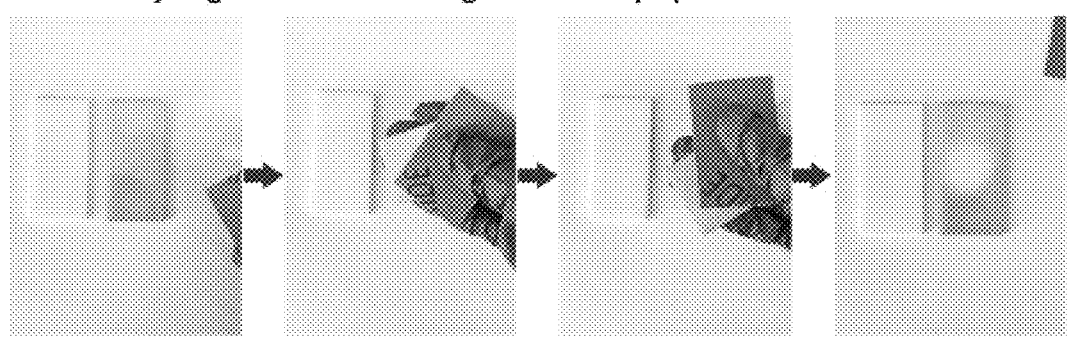

US 12,016,901 B2

TISSUE CATALYZED GROWTH OF POLYMER AS EPITHELIAL LININGS FOR THERAPY

CROSS-REFERENCE TO RELATED APPLICATIONS

This application claims priority under 35 U.S.C. § 119(e) to U.S. Provisional Patent Application, U.S. Ser. No. 62/947,582, filed Dec. 13, 2019, U.S. Provisional Patent Application U.S. Ser. No. 63/050,206, filed Jul. 10, 2020, and U.S. Provisional Patent Application U.S. Ser. No. 63/050,216, filed Jul. 10, 2020, the contents of each of which are incorporated herein by reference in their entirety.

GOVERNMENT SUPPORT

This invention was made with government support under EB000244 awarded by the National Institutes of Health. The government has certain rights in the invention.

BACKGROUND OF THE INVENTION

The small intestine is a versatile organ with multiple physiological functions. The epithelium that covers the gastrointestinal tract is a versatile tissue, playing essential roles as a permeable barrier for selective transport (e.g., absorption) and as a protective armor against various pathogens. In particular, epithelial tissue of the gastrointestinal tract, especially small intestinal epithelium, is not only a protective shield against physical abrasion, chemical stress, and pathogens, but also a dynamic lining for signal sensing, molecule transport, and immunity coordination. Selective intervention of the small intestinal mucosa is pertinent in disease treatment and health management. In parallel, to address the challenge of specifically and efficiently restoring or augmenting functions of small intestinal epithelium, a large variety of meticulously designed biotechnologies have been developed. These particular technologies, leveraging either exquisitely designed tissue adhesives (e.g., pH-dependent polymers, metal complexes, and targeted nanoparticles) or systematically engineered tissue substitutes (e.g., epithelial grafts, autologous cell-sheets, and plastic epithelium-sleeve), are effective tools for facilitating restoration of epithelial dysfunctions and treatment of systemic diseases[1-7]. Despite these advances in research laboratories, broad adoption of these technologies in medical laboratories and healthcare clinics has been limited, consequently stifling their impact[8-10]. This narrow implementation is a result of multiple factors: invasive transplantation, potential immunogenicity, toxicity, and the inaccuracy, instability and inconvenience of current tissue targeting strategies, restricting selective small intestine access.

Similarly, the capability of intervention in the small intestine for digestive disorders and systemic disease treatments has intrigued the scientists to develop a variety of targeted medications[31,32]. However, the challenge of small intestine specific targeting has stifled broad adoption[9,10]. Alternative technologies such as the intestinal sleeve, which needs surgical implantation, are limited to therapeutics with complex procedure, low biocompatibility, risks of inflammation, and high cost. Thus, evolving functions of epithelial linings through advanced biotechnology while maintaining physiologic properties of the tissue remains a challenge.

SUMMARY OF THE INVENTION

Disclosed herein are compositions, methods, and kits for forming a polymer in situ in a subject. This disclosure enables the growth of polymers on the surface of the epithelial tissue, providing a transient coating layer with tunable functions. The polymeric coating relies on dopamine polymerization catalyzed by an endogenous cellular enzyme (catalase), strong tissue-adhesion generated through chemical crosslinking, and, optionally, functional agents incorporated through facile conjugation. For example, catalase in the epithelial tissue in the gastrointestinal epithelium catalyzes polydopamine growth on small intestinal mucosa. In addition, catalase expression levels along tissues such as the gastrointestinal tract allow for efficient and specific formation of polymeric coatings.

The disclosed compositions, methods, and kits are useful in, for example, augmenting digestion of lactose by immobilizing galactosidase in the intestine, leading to the improvement of lactose digestion; regulation of nutrient uptake by impeding glucose absorption; and the control of drug delivery through prolonging residence time of active pharmaceutical ingredients in particular anatomical locations.

In one aspect, provided herein is a method of forming a polymer in situ in a subject, the method comprising administering to a subject a composition comprising a monomer and an oxygen source, wherein the monomer and the oxygen source contact a catalyst endogenous to the subject and the catalyst polymerizes the monomer, wherein the monomer is dopamine, or salt thereof, the oxygen source is hydrogen peroxide or urea hydrogen peroxide, and the endogenous catalyst is selected from a catalase or a peroxidase.

In one aspect, the disclosure provides a composition comprising dopamine, an oxygen source, and optionally a buffer. In some aspects, the composition further a digestive enzyme, a nutrient blocker, a nutraceutical, a radioprotective agent, an active pharmaceutical ingredient, a diagnostic agent, or a combination thereof.

In another aspect, the disclosure provides a method of treating a disease or disorder comprising administering an effective amount of a composition as described herein to a subject in need thereof.

In one aspect, the disclosure provides a method of preventing a disease or disorder comprising administering an effective amount of a composition as described herein to a subject in need thereof.

In a further aspects, the disclosure also provides kits comprising a composition as described herein and instructions for administering the same.

The details of certain embodiments of the present disclosure are set forth in the Detailed Description of Certain Embodiments, as described below. Other features, objects, and advantages of the present disclosure will be apparent from the Definitions, Examples, and Claims.

DETAILED DESCRIPTION OF THE FIGURES

Figure 1B:
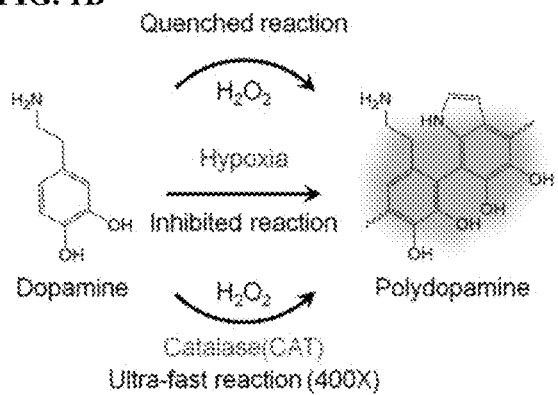
Figure 1C:
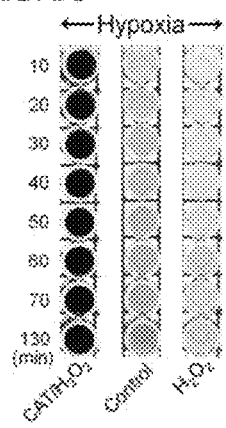
Figure 1D:
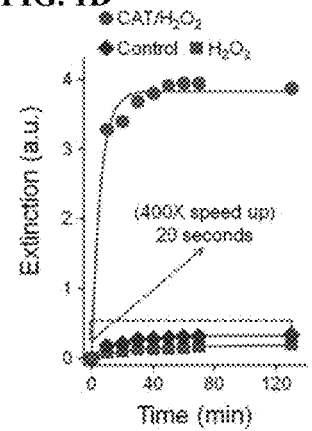
Figure 1E:
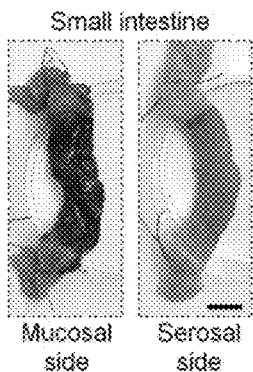
Figure 1F:
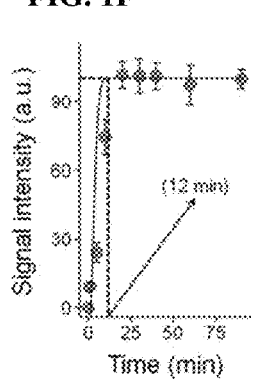
Figure 1G:
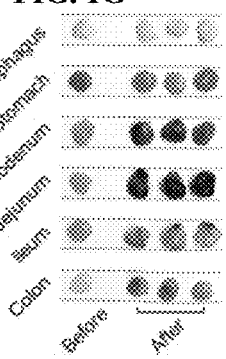
Figure 1H:
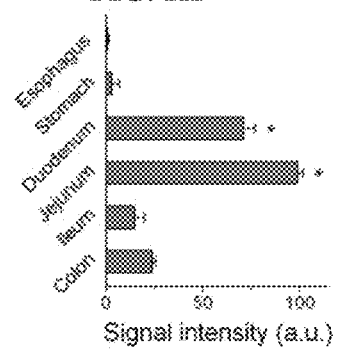

FIGS. 1A-1H. Endogenous enzyme catalyzed polydopamine growth on small intestinal epithelium. FIG. 1A shows a schematic illustration of the tissue-accelerated polymerization of the present disclosure technology. Dopamine monomers in an oral monomer solution rapidly oxidize in the presence of hydrogen peroxide ($H_2O_2$) under endogenous catalase catalysis, and form a polydopamine coating on the small intestinal epithelium. This specific small intestine coating and targeting was achieved due to the uneven distribution of catalase along the digestive tract. FIG. 1B shows a schematic illustration of the catalase-accelerated polydopamine polymerization in a hypoxic environment. In an extremely oxygen deficient environment as depicted above the horizontal arrow, the dopamine (colorless) oxidation (using oxygen as oxidant) and polydopamine (dark-brown color) formation were inhibited, and almost quenched even in the presence of $H_2O_2$. In contrast, catalase can boost oxygen release (using $H_2O_2$ as an oxygen source) and speed up polydopamine polymerization, e.g., by approximately 400 times. Accordingly, as shown under the horizontal arrow, colorless dopamine is rapidly polymerized to polydopamine in the presence of hydrogen peroxide and catalase. TAPPE=tissue-accelerated polymerization on the exterior epithelium. FIG. 1C shows a visual observation of polydopamine polymerization under conditions shown in FIG. 1B at various time points. FIG. 1D shows extinction measured at 700 nm for the samples shown in FIG. 1C. The optical extinction produced in 20 seconds under catalase catalysis was the same as the extinction produced in 2 hours under other conditions. FIG. 1E depicts images showing polydopamine coating on the mucosal and serosal side of the porcine small intestine after an ex vivo coating treatment was applied as disclosed herein, with the scale bar indicating 2 cm. FIG. 1F shows a quantitative evaluation of the in situ ex vivo polymerization kinetics. The polydopamine signal reached completion within 12 minutes. Data are reported as means±SD over three porcine tissue samples. FIG. 1G depicts images showing porcine tissue samples in different parts of the gastrointestinal tract before and after the tissue-accelerated polymerization coating. Samples (6 mm in diameter) were collected at three random sites of polydopamine coated tissue. FIG. 1H shows quantitative measurements of the polydopamine signal intensities of samples shown in FIG. 1G. The intensity differences between the small intestine and other tissue are statistically significant. ****$P<0.05$, one-way analysis of variance (ANOVA) and post hoc Bonferroni. Data are reported as means±SD over three different tissue samples.

FIGS. 2A-2H. Biological mechanisms of tissue-accelerated polymerization. FIG. 2A shows an evaluation of the relationship between tissue catalytic capacity and polydopamine polymerization. Porcine tissue lysates were added individually into the tissue-accelerated polymerization solution, and the extinction of each solution was measured at 700 nm. Both visual assessments (top panel) and quantitative measurements (bottom panel) of the polydopamine solution show catalytic capacity difference when comparing the small intestinal epithelium with other tissues and control (without lysates). *$P<0.05$, one-way ANOVA and post hoc Bonferroni. Data are reported as means±SD over three replicates. FIGS. 2B-2C show verification of the exclusive role of catalase in reactions shown in FIG. 2A by treating the lysates with either a catalase-specific inhibitor (FIG. 2B) or antibody that induces immunoprecipitation (FIG. 2C). The relative catalytic capacity differences between the treated and untreated groups are visually and statistically significant. *$P<0.001$ by two-tailed t-test. Data are reported as means±SD over three different tissue samples. FIGS. 2D-2F show the quantification of catalase expression (gene and protein levels) along the porcine gastrointestinal tract by catalase activity analysis (FIG. 2D), real-time PCR (FIG. 2E), and western blotting (FIG. 2F). Similar distribution profiles were achieved in FIGS. 2D-2F, indicating higher catalase expression level in the small intestinal epithelium compared to other tissues. The differences are statistically significant. *$P<0.05$, one-way ANOVA and post hoc Bonferroni. Data are reported as means±SD over three replicates. FIG. 2G shows the microscopic analysis of polydopamine coated small intestinal epithelium, showing a thin polydopamine layer coated on the exterior villi (indicated by arrows), but nothing on control tissue (without coating). Scale bars, 150 µm. FIG. 2H shows the bright-field imaging of uncoated tissue slices treated by specific peroxisome/catalase staining (left panels) and with the tissue-accelerated polymerization solution (right panels). Dark-brown polydopamine spots were observed inside villus tips and the staining pattern is consistent with the conventional peroxisome/catalase staining. Scale bars, 150 µm.

Figure 3A:
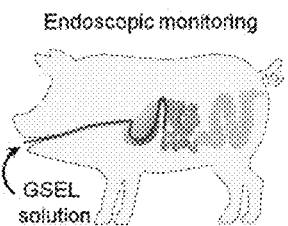
Figure 3B:
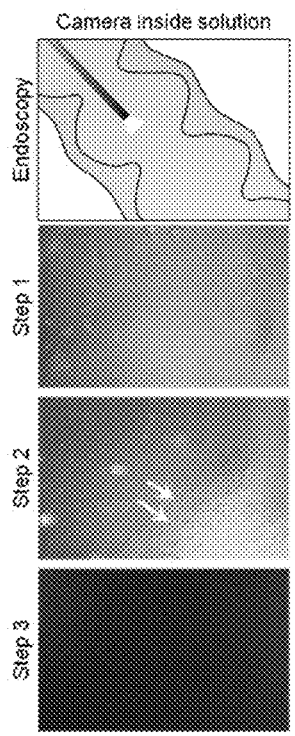
Figure 3C:
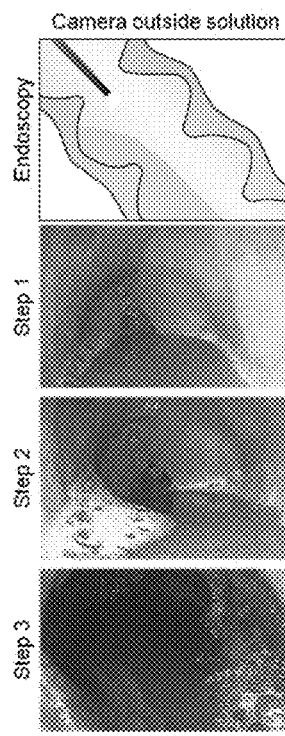
Figure 3D:
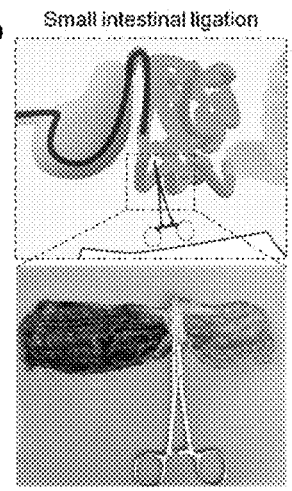
Figure 3E:
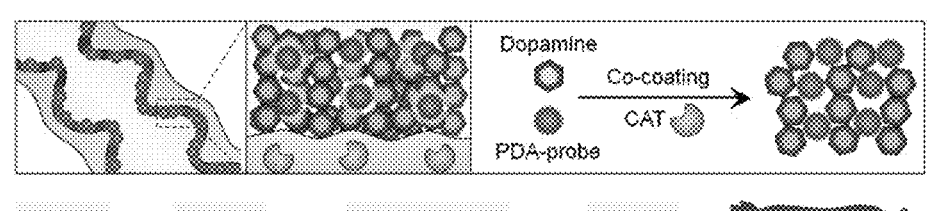
Figures 3F, 3G, 3H:
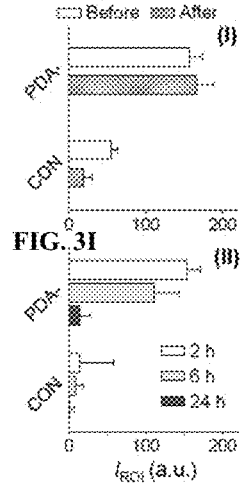
Figure 3I:
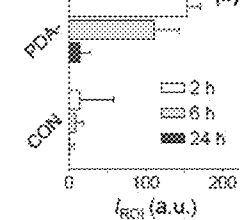

FIGS. 3A-3I. In vivo performance of the tissue-accelerated polymerization coating in pigs. FIGS. 3A-3C show schematics and photographs of in vivo gastrointestinal endoscopic real-time recording of polydopamine formation during the tissue-accelerated polymerization process. Pigs were directly administered the tissue-accelerated polymerization solution to the porcine small intestine through a catheter under endoscopic visual guidance, and the endoscopic camera was placed both inside and outside the solution within the small intestine for observation. FIGS. 3B-3C show endoscopic images (bottom three panels) revealed the steps during the polydopamine coating. Oxygen bubbles were generated at the epithelium-solution interface (indicated by white arrows). FIG. 3D shows a schematic illustration of small intestinal ligation (top panel) and direct polydopamine coating evaluation (bottom panel). The tissue-accelerated polymerization solution filled the intestinal cavity up until the clamp site, unable to pass down to the lower small intestine. The isolated tissue showed different polydopamine coating before and after the clamp site. FIG. 3E shows a schematic illustration of intestinal retention of the polydopamine coating indicated by X-ray imaging of the polydopamine-probes. X-ray images were taken for two tests: (I) short-term stability evaluation (rinsing the coated area) and (II) long-term retention assessment (liquid diet for 24 hours). PDA=polydopamine. FIG. 3F shows X-ray images of polydopamine probes as well as the polydopamine coating layer stably residing in the small intestine before and after rinsing the imaging area, shown in test (I). The stomach and small intestine (SI) areas were separated with white dotted lines. Polydopamine coating is indicated by yellow arrows. FIG. 3G shows X-ray images of intestinal retention of polydopamine coating for the duration of test (II). Conventional probes were nearly undetectable after food exposure. FIG. 3H shows a quantitative signal intensity analysis of coated small intestine areas, region of interests (ROIs), in FIG. 3F. The enhancement and stability of the signals (before and after rinsing) in polydopamine-probes relative to conventional (CON) probes demonstrate efficient probe incorporation and stable polydopamine coating. Data are reported as means±SD over three different measurements. FIG. 3I shows a quantitative signal intensity analysis of the polydopamine coating over time in FIG. 3G. From 2 to 6 hours, there was only a 28% signal intensity difference, indicating the prolonged retention of the polydopamine coating. Data are reported as means±SD over three different measurements.

Figure 4A:
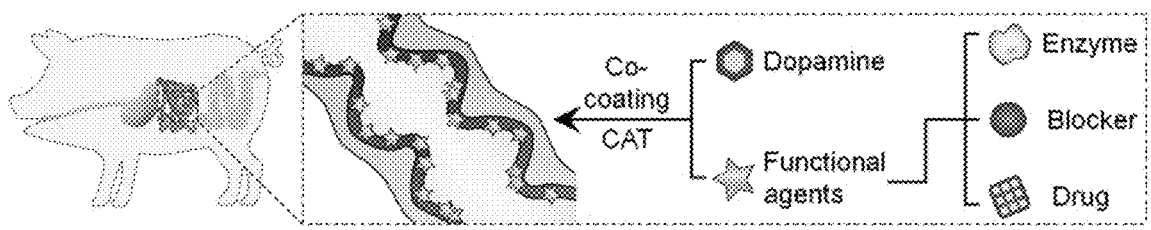
Figure 4B:
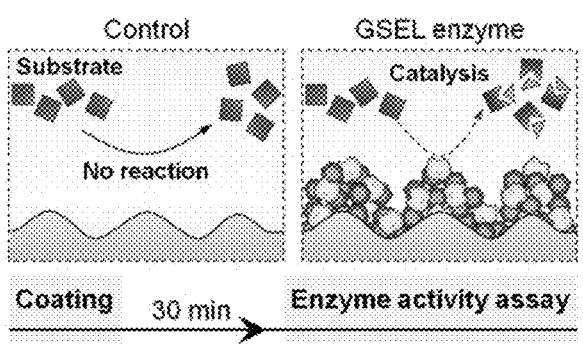
Figure 4C:
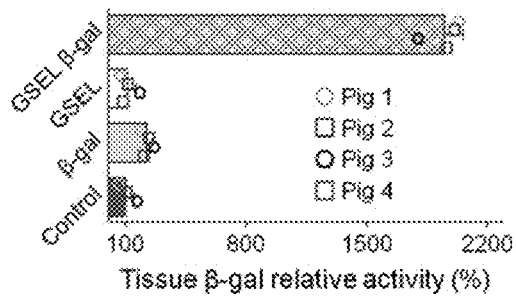
Figure 4D:
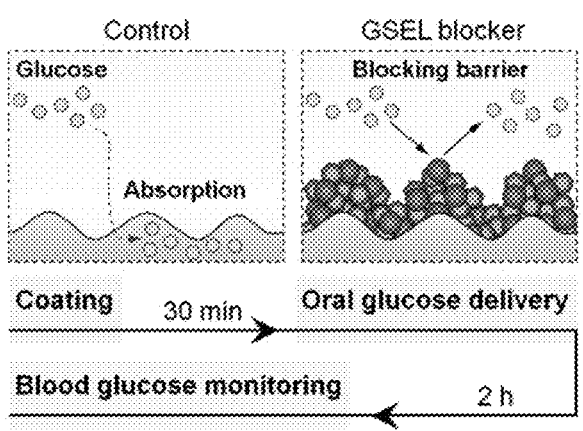
Figure 4E:
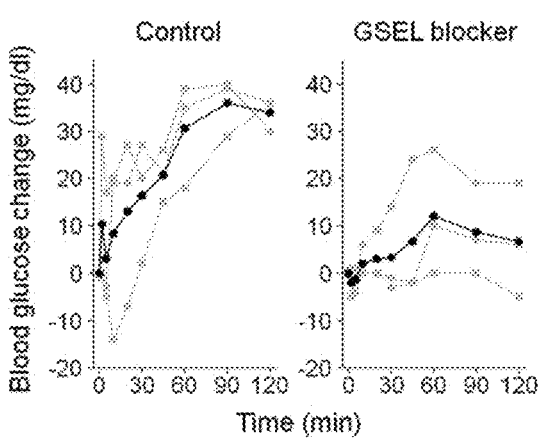
Figure 4F:
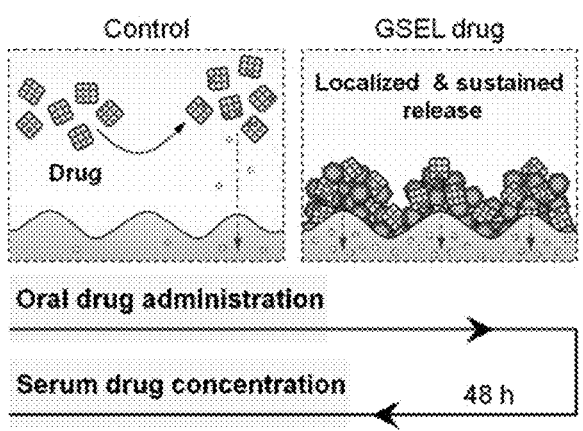
Figure 4G:
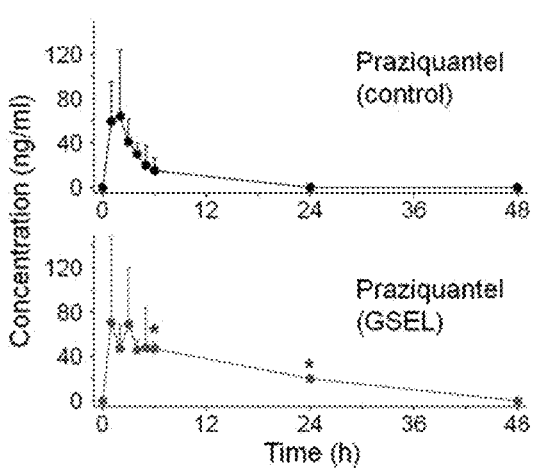

FIGS. 4A-4G. Therapeutic applications enabled by tissue-accelerated polymerization. FIG. 4A shows a schematic illustration of the tissue-accelerated polymerization therapeutic platform. Functional agents, including a digestive enzyme, nutrient blocker, and anthelmintic drug, were incorporated into the platform through co-administering with the tissue-accelerated polymerization solution orally to pigs. FIG. 4B shows a schematic illustration of incorporating digestive enzymes (β-galactosidase, β-gal) into polydopamine coating layer on porcine intestinal epithelium for augmenting the digestion of substrates (lactose). After the in vivo coating, the β-gal activity of the coated epithelium was evaluated. FIG. 4C shows a quantitative comparison of β-gal activity showing increased enzymatic activity in tissue-accelerated polymerization-based β-gal coated tissues compared to negative controls. Data are reported as means±SD over four animals. FIG. 4D shows a schematic illustration of incorporating nano-crosslinkers (blockers) into the tissue-accelerated polymerization coating to enable an impermeable polydopamine coating layer, preventing glucose uptake in the small intestine. After the in vivo coating, oral glucose was administered to the pigs, followed by monitoring blood glucose concentration. FIG. 4E shows a quantitative comparison of blood glucose changes showing reduced blood glucose responses of the pigs with the tissue-accelerated polymerization coating relative to the control (without coating). Data was averaged between animals (each animal represented by a grey line) in each group (shown by the black line). FIG. 4F shows a schematic illustration of coating drug (praziquantel) particles on intestinal epithelium for sustained release of therapeutics in the small intestine. After the oral administration of the praziquantel-tissue-accelerated polymerization solution, serum drug concentrations were analyzed over 48 hours. FIG. 4G shows a quantitative comparison of the pharmacokinetics showing extended retention time of the praziquantel (with the tissue-accelerated polymerization solution) relative to the control (without tissue-accelerated polymerization solution). *indicates p<0.02, two sample t test comparing praziquantel-tissue-accelerated polymerization and control groups at matching time points. Data are reported as means±SD over three animals.

Figure 5A:
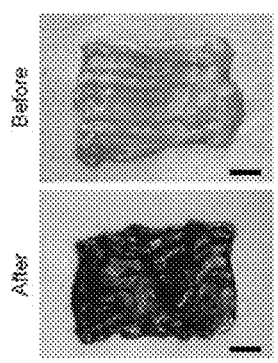
Figure 5B:
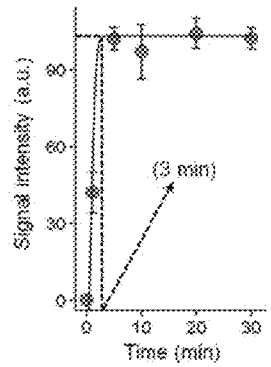
Figure 5C:
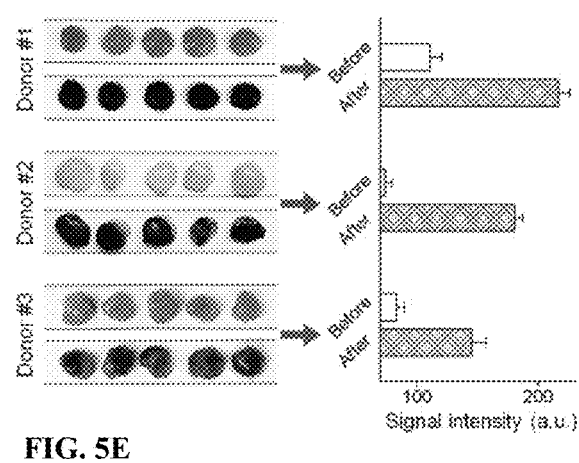
Figure 5D:
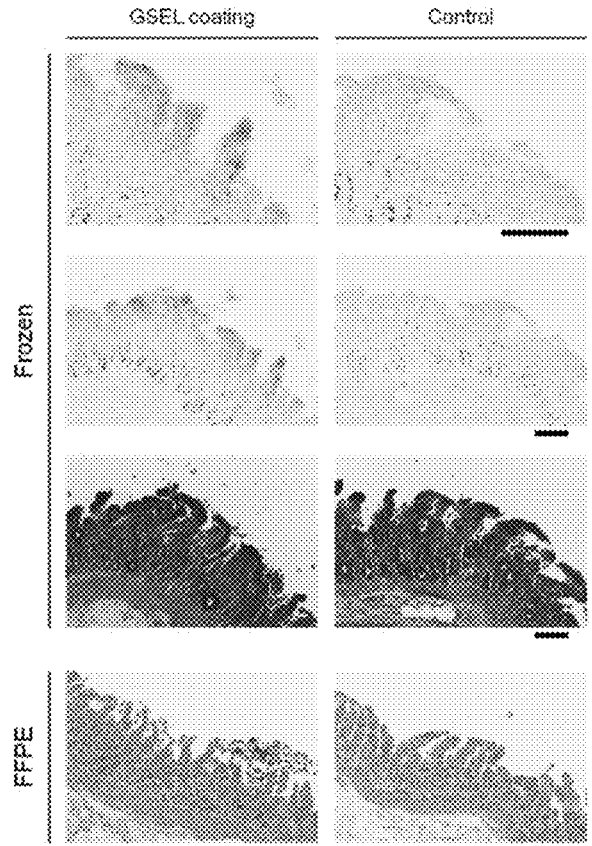
Figure 5E:
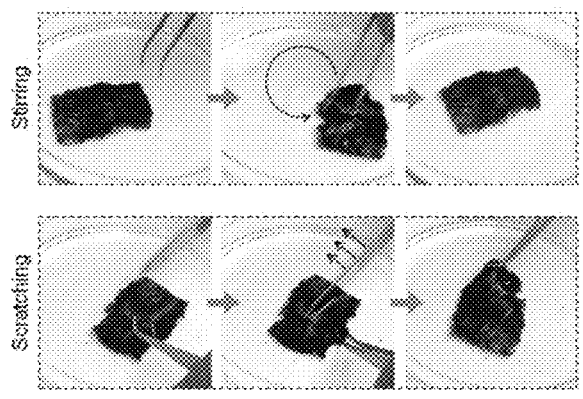
Figure 5F:
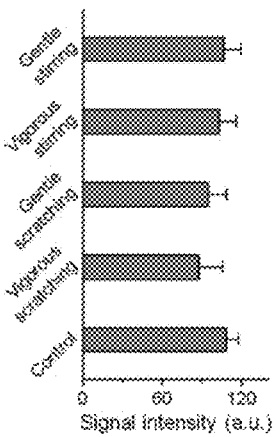
Figure 5G:
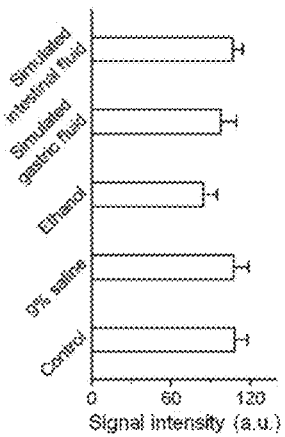

FIGS. 5A-5G. Compatibility of human tissues with tissue-accelerated polymerization. FIG. 5A shows images showing fresh resected tissue specimens from human small intestine before and after ex vivo tissue-accelerated polymerization coating. The dark-brown polydopamine coating was clearly observed on the human small intestinal surface (bottom panel). Scale bar, 1 cm. FIG. 5B depicts coating kinetics showing ultrafast polydopamine signal development in human tissues ex vivo. The polydopamine signal reaches completion within 3 minutes. FIG. 5C shows an evaluation of tissue-accelerated polymerization consistency. Tissue specimens from 3 donors with different ages, races and genders were tested. Five ex vivo assessments were performed on random sites of the human small intestine. Quantitative measurements (right panel) of the polydopamine coating signals of samples (6 mm diameter) before and after coating (left panels) confirmed consistent tissue-accelerated polymerization coating performance. Data are reported as means±SD over five replicates. FIG. 5D shows microscopic and histological analyses of frozen specimens (40 μm thickness) and FFPE specimens (5 μm thickness) collected from polydopamine coated human small intestinal epithelium. A thin polydopamine layer was observed on the exterior villi of coated tissues. Uncoated tissues were used as controls. Histological study (hematoxylin and eosin (H&E) staining) of adjacent frozen tissue slides and FFPE samples showed that the epithelial layers remained intact, with staining patterns similar to controls, demonstrating the absence of tissue toxicity. Scale bars, 150 μm. FIG. 5E depicts representative images showing no obvious polydopamine signal reduction in coated human small intestine after mechanical stirring and scratching. FIG. 5F shows a quantitative ex vivo evaluation of polydopamine signal intensities of coated tissues under a series of physical conditions. The intensity differences among all conditions are not statistically significant (two-tailed t-test). Data are reported as means±SD over three replicates. FIG. 5G shows a quantitative ex vivo evaluation of polydopamine signal intensities of coated tissues under a series of chemical conditions. The intensity differences among all conditions are not statistically significant (two-tailed t-test). Data are reported as means±SD over three replicates.

Figure 6A:
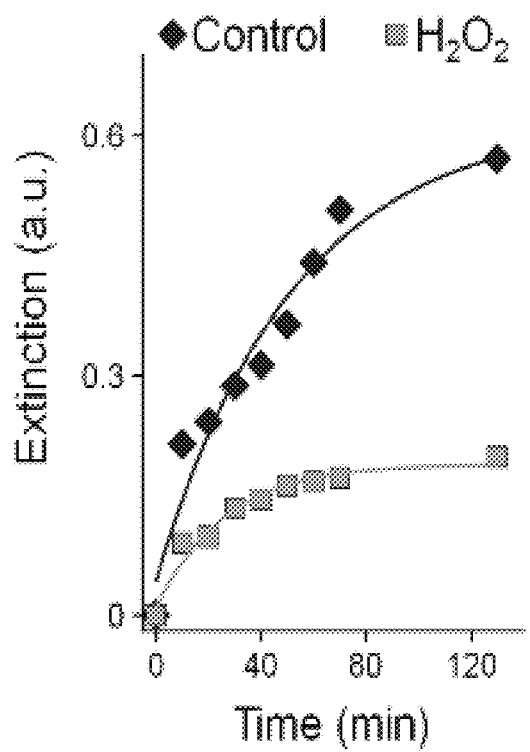
Figure 6B:
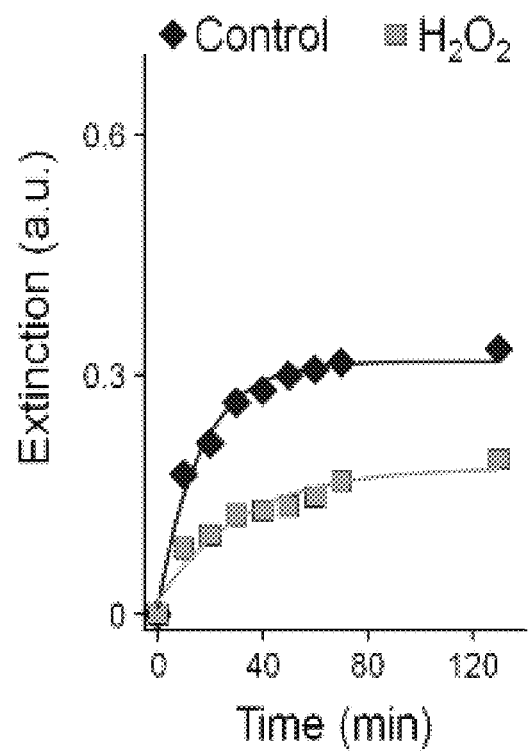

FIGS. 6A-6B. Comparison of polydopamine polymerization kinetics in different reaction conditions. FIG. 6A shows extinction measured at 700 nm for the samples (with and without $H_2O_2$ (control)) undergoing polydopamine polymerization in the air. FIG. 6B shows extinction measured at 700 nm for the samples (with and without $H_2O_2$ (control)) undergoing polydopamine polymerization in extremely low oxygen-level (hypoxic environment). In extremely low oxygen-level, the polydopamine polymerization (without $H_2O_2$) was inhibited by 65% compared to the conventional condition (reaction in the air, without $H_2O_2$). The addition of $H_2O_2$ almost quenched the polydopamine polymerization in the air and in the low oxygen condition.

Figure 7A:
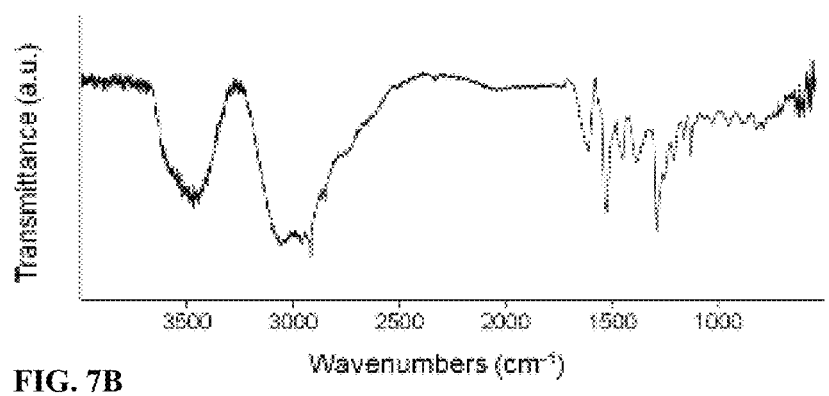
Figure 7B:
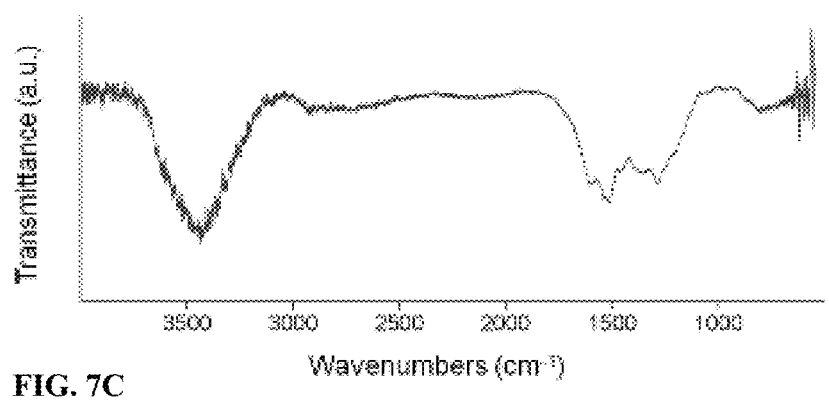
Figure 7C:
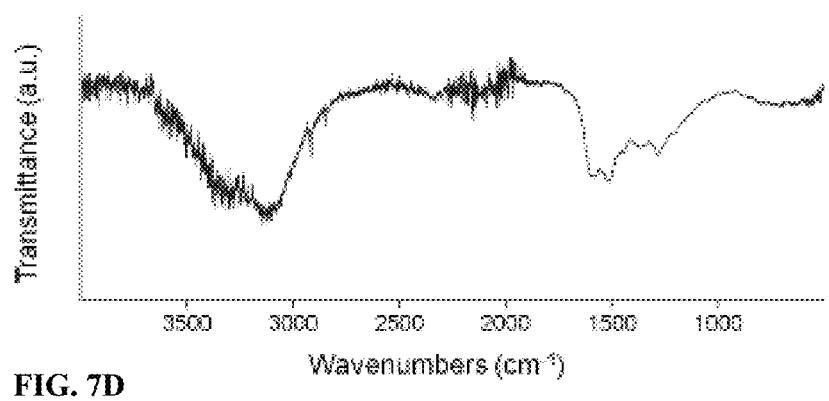
Figure 7D:
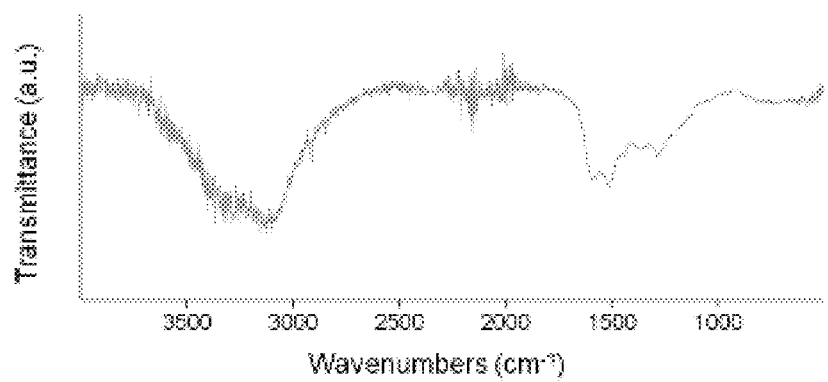

FIGS. 7A-7D. Fourier transform infrared (FTIR) spectra of dopamine, polydopamine standard and polymerization products. FTIR spectra of dopamine (FIG. 7A) and polydopamine (FIG. 7B) prepared under conventional conditions were measured and used as standards. FTIR spectra confirm the polydopamine formation in the polymerization products under catalase (commercially purified) catalysis (FIG. 7C) and catalase (from tissue lysates) catalysis (FIG. 7D). The indole (or indoline) peaks (1515 and 1605 $cm^{-1}$) and the broad peak spanning 3200-3500 $cm^{-1}$ (hydroxyl structures) in catalase catalyzed polymerization products are nearly identical with peaks in the polydopamine standard.

Figure 8A:
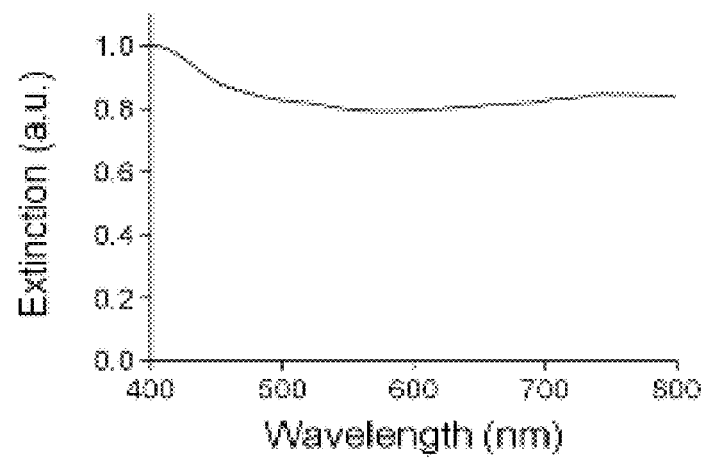
Figure 8B:
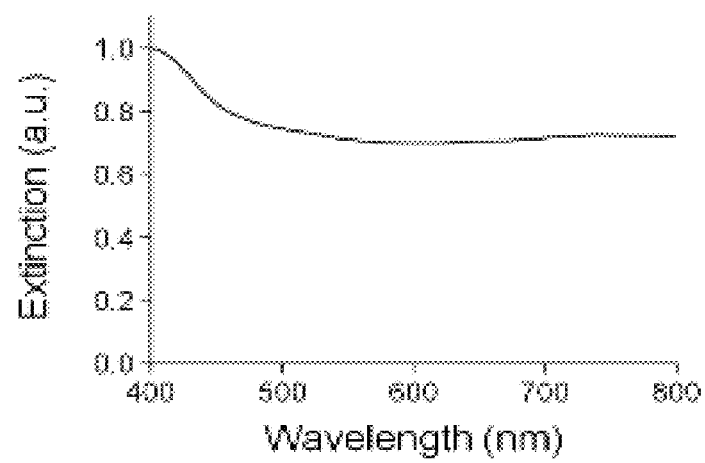
Figure 8C:
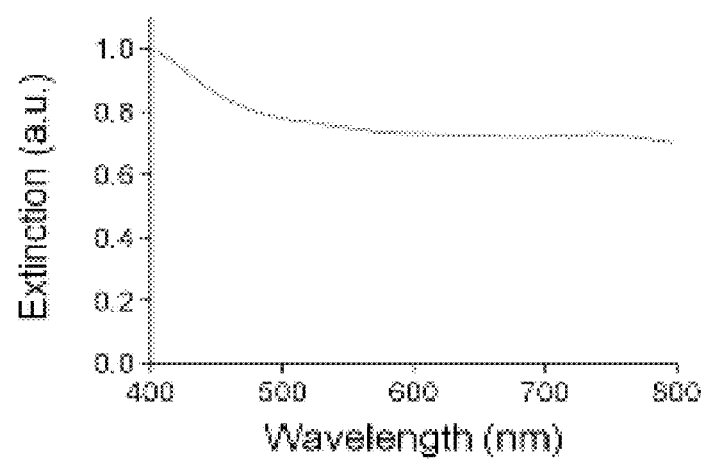

FIGS. 8A-8C. Normalized extinction spectra of polydopamine standard and polymerization products. UV-Vis spectra of polydopamine standard (FIG. 8A), polymerization product under catalase (commercially purified) catalysis (FIG. 8B), and polymerization product under catalase (from tissue lysates) catalysis (FIG. 8C) are nearly identical, confirming the polydopamine formation in FIG. 8B and FIG. 8C.

FIG. 9. Evaluation of the tissue-accelerated polymerization coating using porcine tissue specimens. Mucosa and serosa of the small intestine (schematic illustration, left panel) were exposed to the tissue-accelerated polymerization solution separately, and a dark-brown polydopamine coating was observed only on the mucosal side of the tissue (middle panel), but not on the serosal side of the tissue (right panel). To confirm the coating specificity, two ends of the small intestinal tissue were tied using sutures, and only the sections in between the sutures were exposed to the tissue-accelerated polymerization solution.

Figure 10:
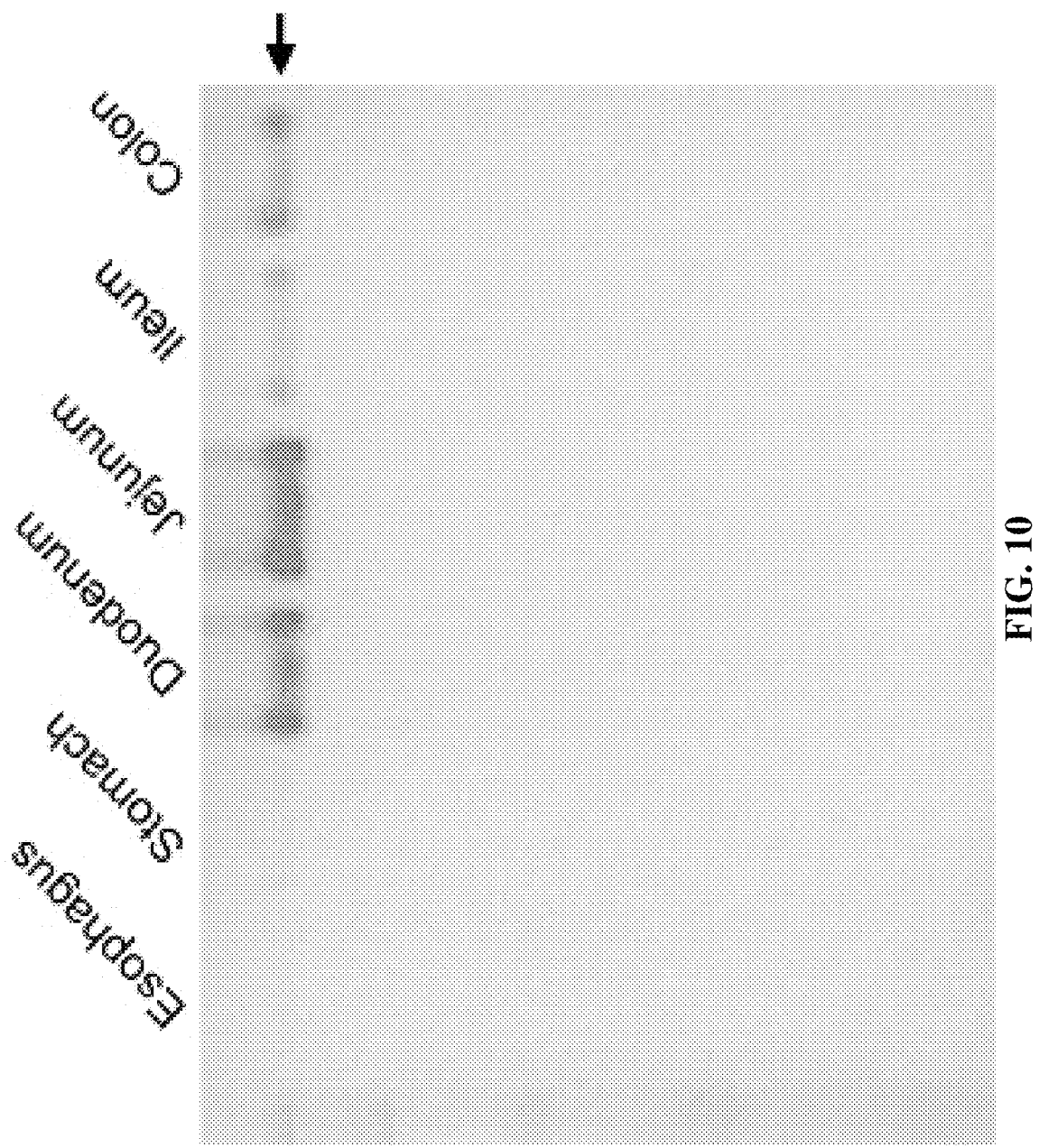

FIG. 10. Catalytic capacity analysis of tissue lysates through native gel electrophoresis. Tissue lysates from different parts of the porcine gastrointestinal tract were loaded on a non-denaturing polyacrylamide gel, electrophoresed to allow protein separation, and stained for catalytic capacity analysis. After staining by using the tissue-accelerated polymerization solution, dark-brown polydopamine signal was visualized on the gel. Only one sharp band (indicated by the arrow) was observed in each lane, supporting catalase's predicted role as the sole enzyme responsible for polydopamine polymerization.

Figure 11B:
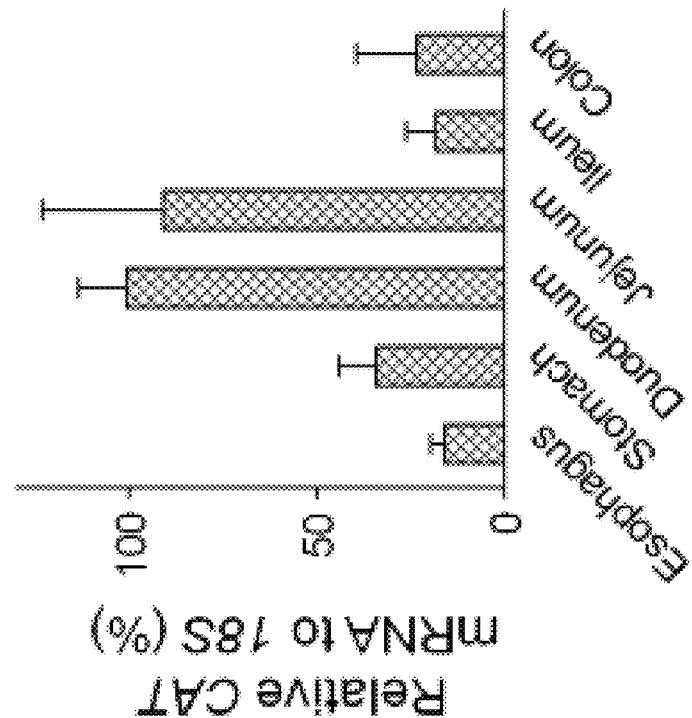
Figure 11A:
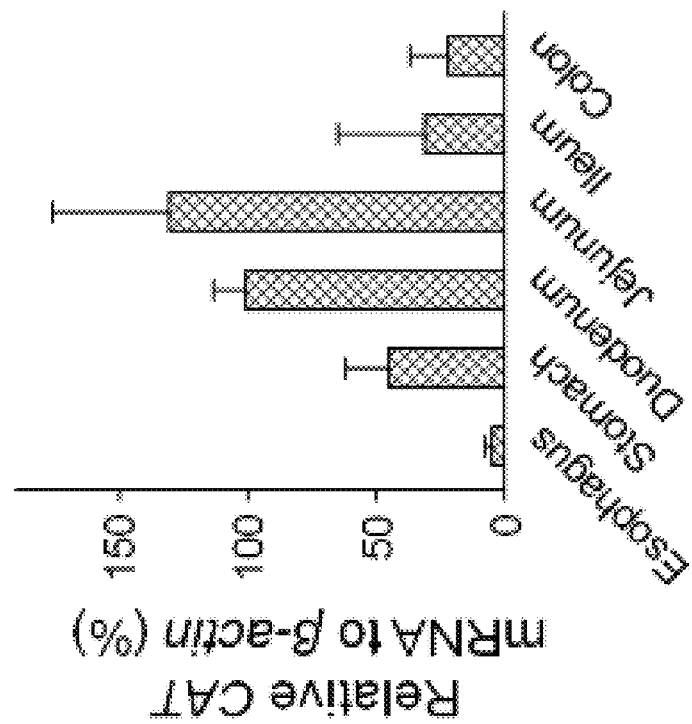
Figure 12A:
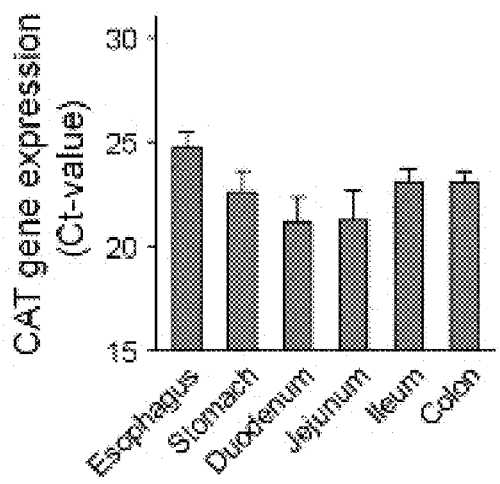
Figure 12B:
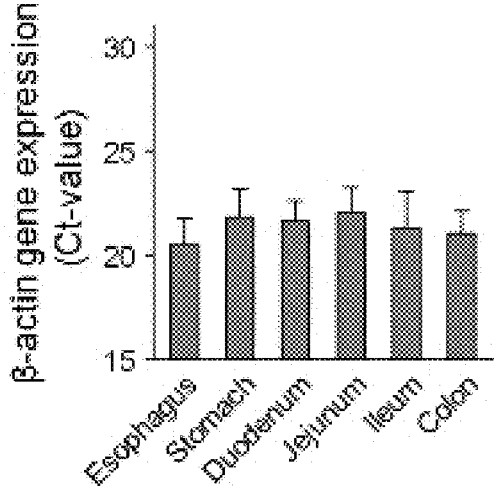
Figure 12C:
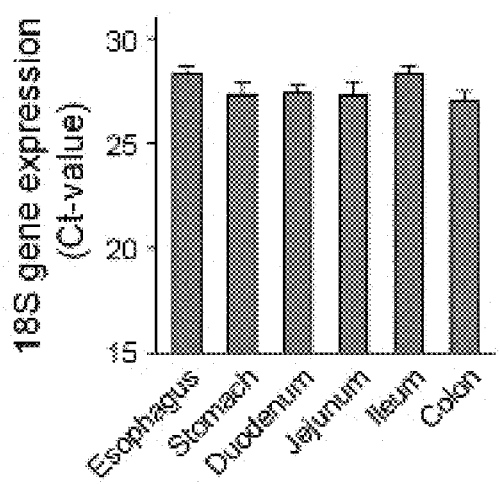
Figure 12D:
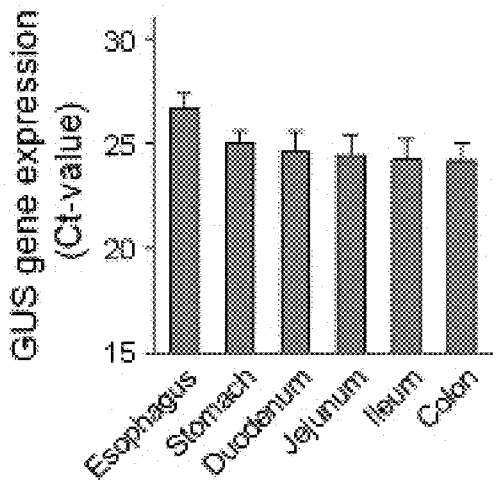
Figure 12E:
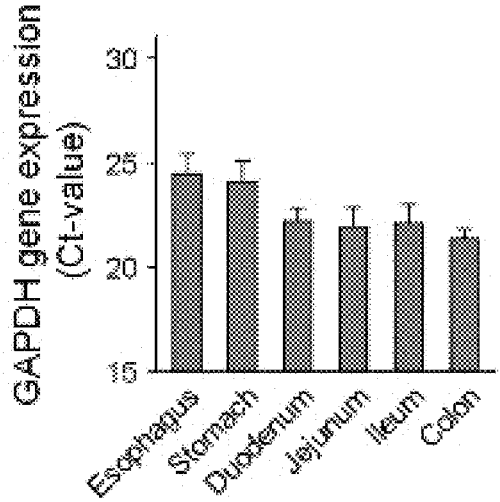

FIGS. 11A-11B. Quantification of catalase mRNA levels in tissue by using real-time PCR. Housekeeping genes, including β-actin (FIG. 11A) and 18S (FIG. 11B), were used as controls for quantifying catalase mRNA levels. Tissue specimens from 4 pigs were tested. The small intestine catalase mRNA expression levels had similar distribution profiles in FIG. 11A and FIG. 11B. Data are reported as means±SD over 4 animals.

FIGS. 12A-12E. Ct-values of for gene expression levels. For mRNA level quantification, catalase (FIG. 12A), β-actin (FIG. 12B), 18S (FIG. 12C), GUS (FIG. 12D), and GAPDH (FIG. 12E) genes were included in the test. Tissue specimens from 4 pigs were tested. Data are reported as means±SD over 4 animals.

FIG. 13. Bright field images of polydopamine coated small intestinal epithelium. Porcine small intestinal tissues were exposed to the tissue-accelerated polymerization solution ex vivo for 3 and 15 minutes, and examined under the bright field microscopy. Polydopamine first deposited on intestinal villus tips (indicated by yellow arrows, top panel), and then coated the whole villi, as well as surrounding area (bottom panel). Scale bars, 500 μm.

Figure 14A:
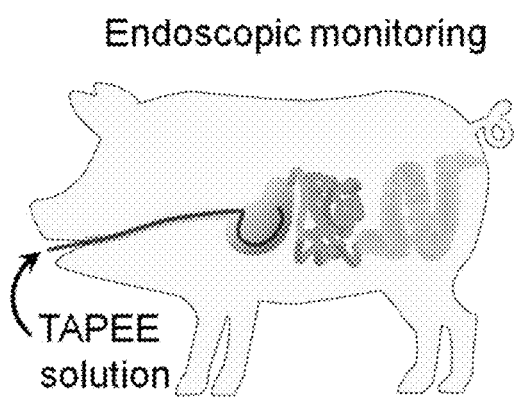
Figure 14C:
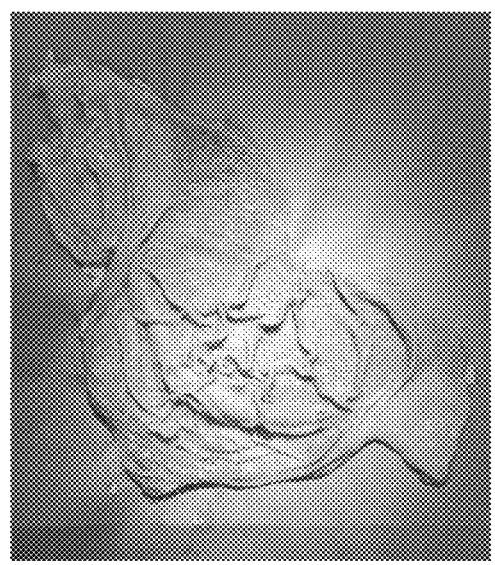
Figure 14B:
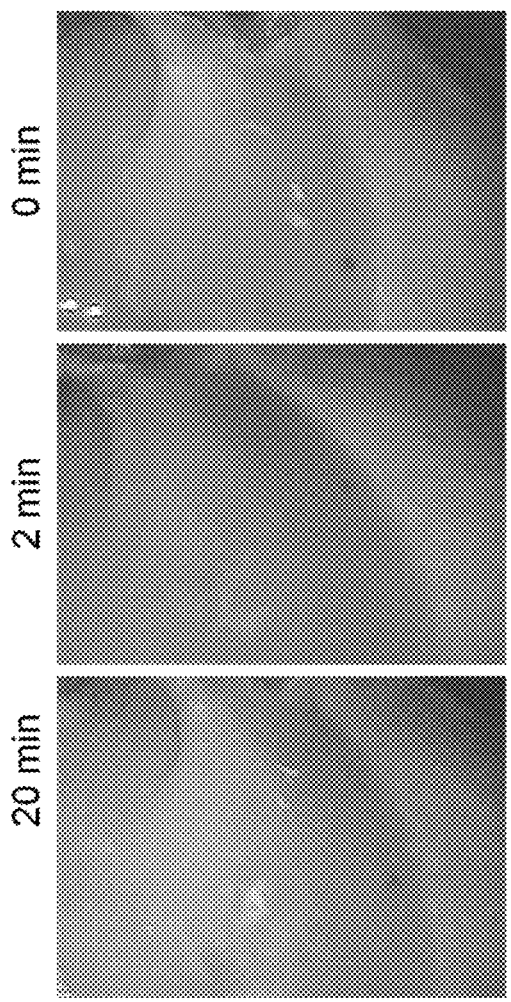

FIGS. 14A-14C. Evaluation of in vivo tissue-accelerated polymerization coating performance in the stomach. FIG. 14A shows a schematic illustration of gastrointestinal endoscopic real-time recording the stomach after oral administration of the tissue-accelerated polymerization solution to the stomach. Pigs were under moderate sedation during the whole process. The endoscopic camera was placed outside the solution for observation, and the images were recorded at the same place over time. FIG. 14B shows endoscopic images revealed that no dark-brown polydopamine was visualized in the stomach. The tissue-accelerated polymerization solution in the stomach remains clear over 20 minutes. FIG. 14C shows an image of the isolated stomach from the animal in FIG. 14B confirming no polydopamine coating on the epithelial surface.

Figure 15A:
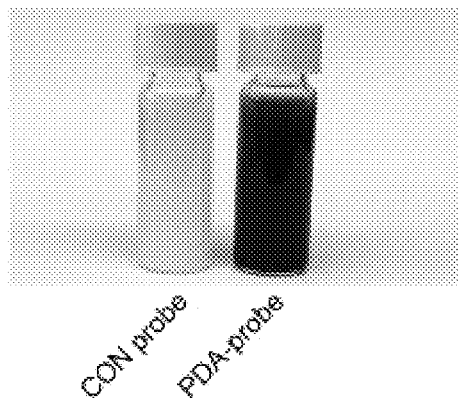
Figure 15B:
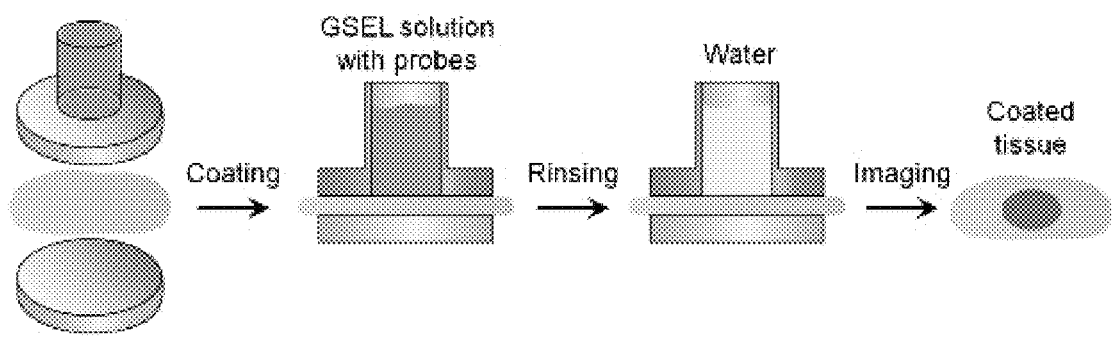
Figure 15C:
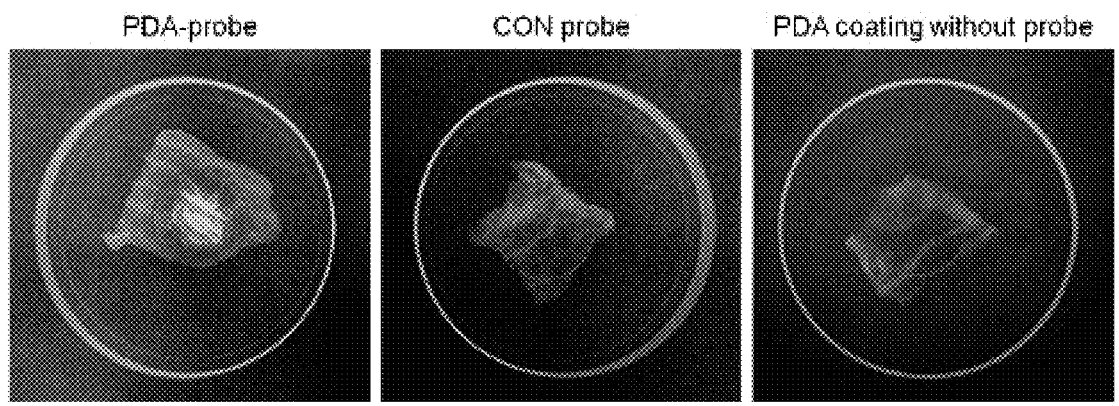

FIGS. 15A-15C. Evaluation of ex vivo polydopamine-probe tissue-coating performance through X-ray imaging. FIG. 15A shows images showing the conventional (CON) probe solution and polydopamine-probe solution. The polydopamine-probe was prepared by encapsulating the conventional probe with a thin layer polydopamine. The dark-brown color of the polydopamine-probe solution comes from chromogenic polydopamine on the probe surface. FIG. 15B shows a schematic illustration of the ex vivo tissue-coating process. The porcine small intestine was placed in the Franz Cell, and the tissue-accelerated polymerization solution (with or without probes) was added into the chamber. After the coating, the coated tissue was rinsed by the water and imaged by the X-ray system. FIG. 15C shows X-ray images of tissues coated by using the tissue-accelerated polymerization solution with polydopamine-probes (left panel), conventional (CON) probes (middle panel), and the tissue-accelerated polymerization solution without probes (right panel). Strong X-ray signals were only observed in the coated area (indicated by red circles) of the polydopamine-probe coated tissue. No obvious X-ray signal was detected in controls where conventional probes or polydopamine alone were applied for coating.

Figure 16A:
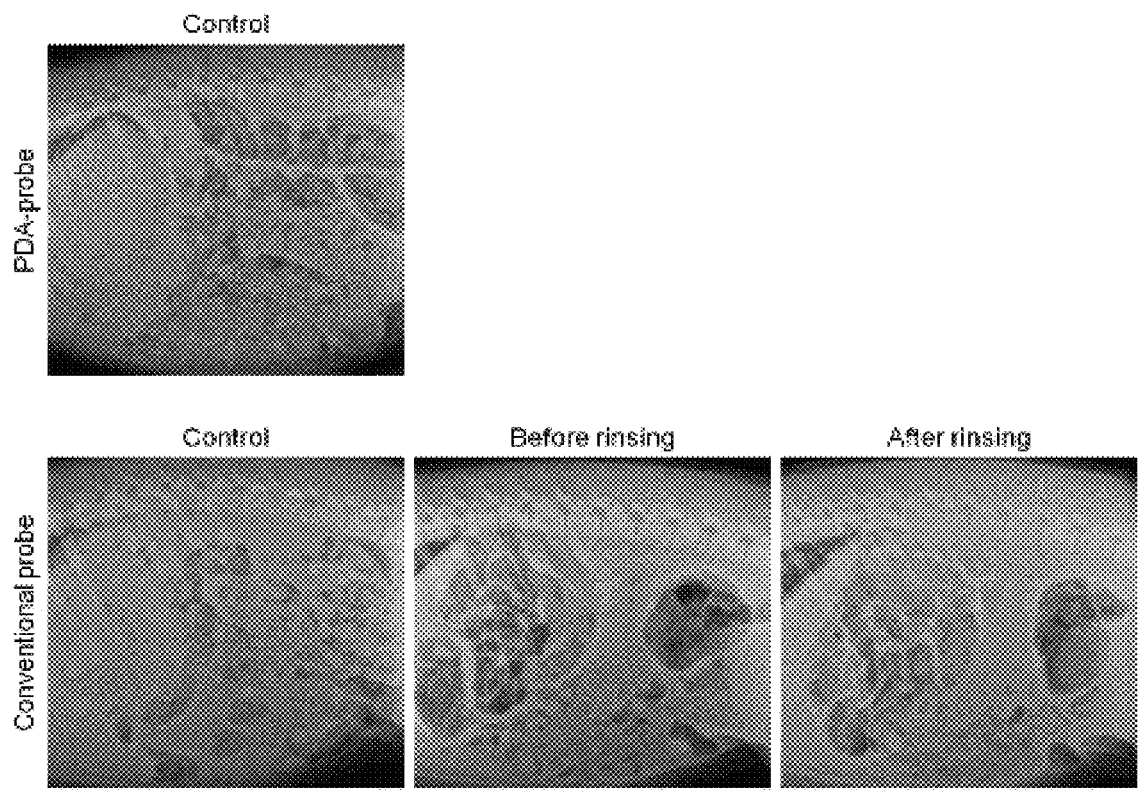
Figure 16B:
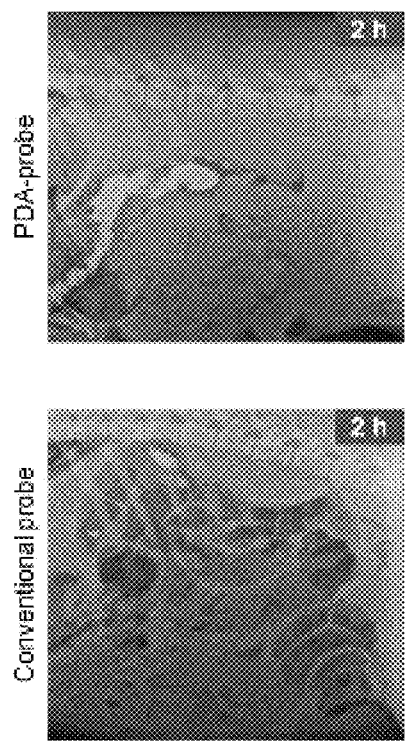

FIGS. 16A-16B. In vivo X-ray imaging of the intestinal retention of the polydopamine coating layer. FIG. 16A shows X-ray images revealing the polydopamine coating stability. Healthy pigs were orally administered the polydopamine-probe suspended tissue-accelerated polymerization solution (top panels) and conventional probes (bottom panels) separately, and imaged by the X-ray system. The solution was directly administered to the small intestine through a catheter under endoscopic visual guidance. The same pigs without administrating probes were imaged and used as controls. Water was used for rinsing the imaging area to test the polydopamine coating stability. FIG. 16B shows X-ray images revealing the intestinal retention of polydopamine over time. A series of X-ray images were periodically taken in the same location at 2, 6 and 24 hours. Animals consistently consumed a liquid diet during imaging, mimicking realistic conditions and testing the stability of the polydopamine coating in the presence of food.

Figure 17A:
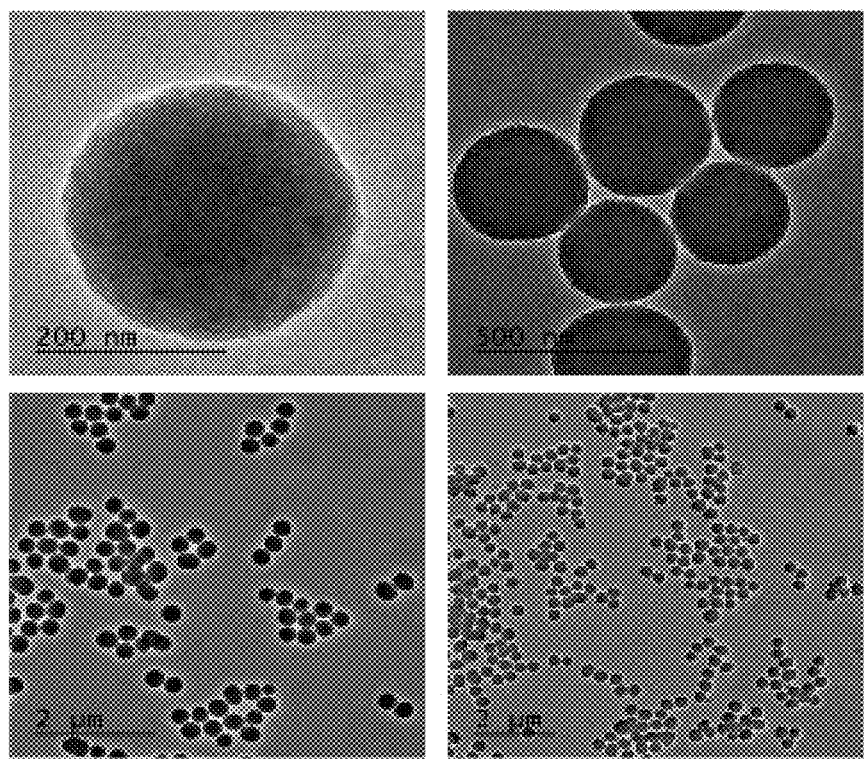
Figure 17B:
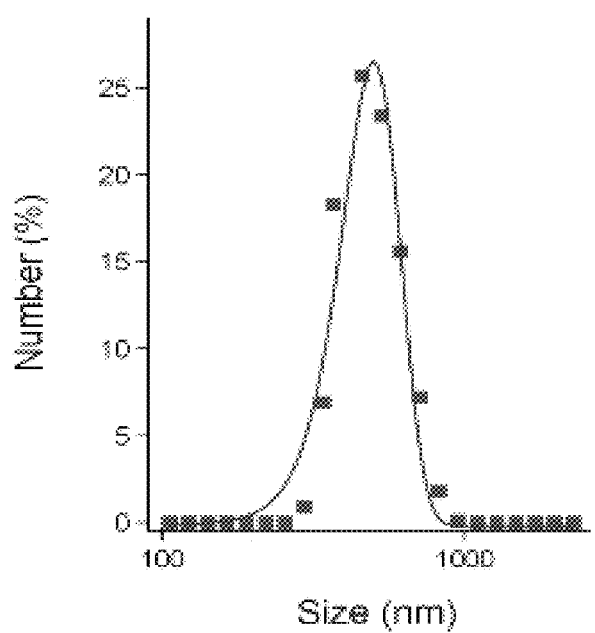

FIGS. 17A-17B. Characterization of nano-crosslinkers. FIG. 17A shows TEM images with different magnifications showing uniform polydopamine nano-crosslinkers. FIG. 17B depicts dynamic light scattering (DLS) analysis showing nano-crosslinkers' hydrodynamic size of 527 nm.

Figure 18A:
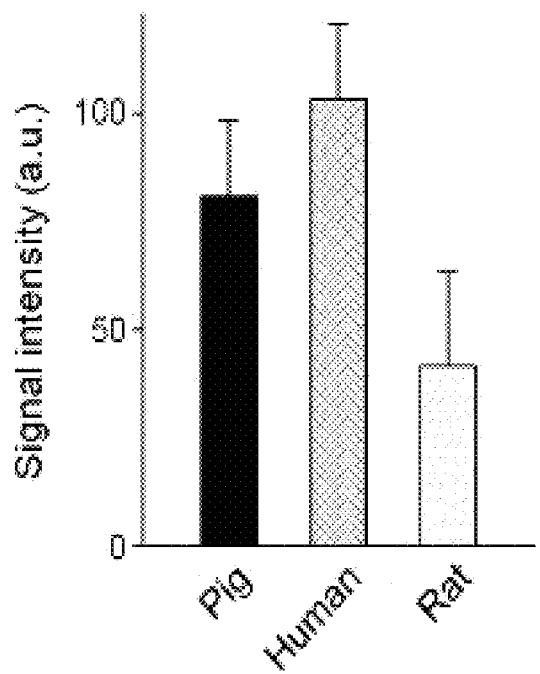
Figure 18B:
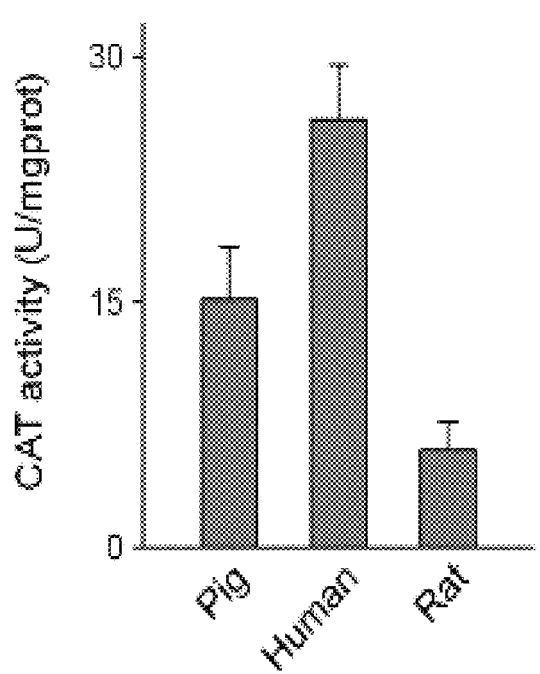

FIGS. 18A-18B. Evaluation of the tissue-accelerated polymerization coating performance across different animal species. Samples (6 mm in diameter) were collected at 3-5 random sites of polydopamine coated tissue, and images of the samples were analyzed for quantification of the polydopamine coating. ImageJ was used to identify regions of interest that included polydopamine coated tissues and excluded 'blank' tissue-free areas. Identical analysis was performed on all samples in each group to obtain an overall average polydopamine signal intensity and assess signal variation. This is an ex vivo study. FIG. 18A shows a quantitative evaluation of the polydopamine coating density on small intestines from pig, human, and rat. Polydopamine signal intensities were measured after the tissue-accelerated polymerization coating, representing the polydopamine coating density. Data are reported as means±SD over three replicates. FIG. 18B shows the quantification of catalase expression by measuring the catalase activity in small intestines from pig, human, and rat. Tissue specimens were collected from same animals in FIG. 18A. Data are reported as means±SD three replicates.

Figure 19:
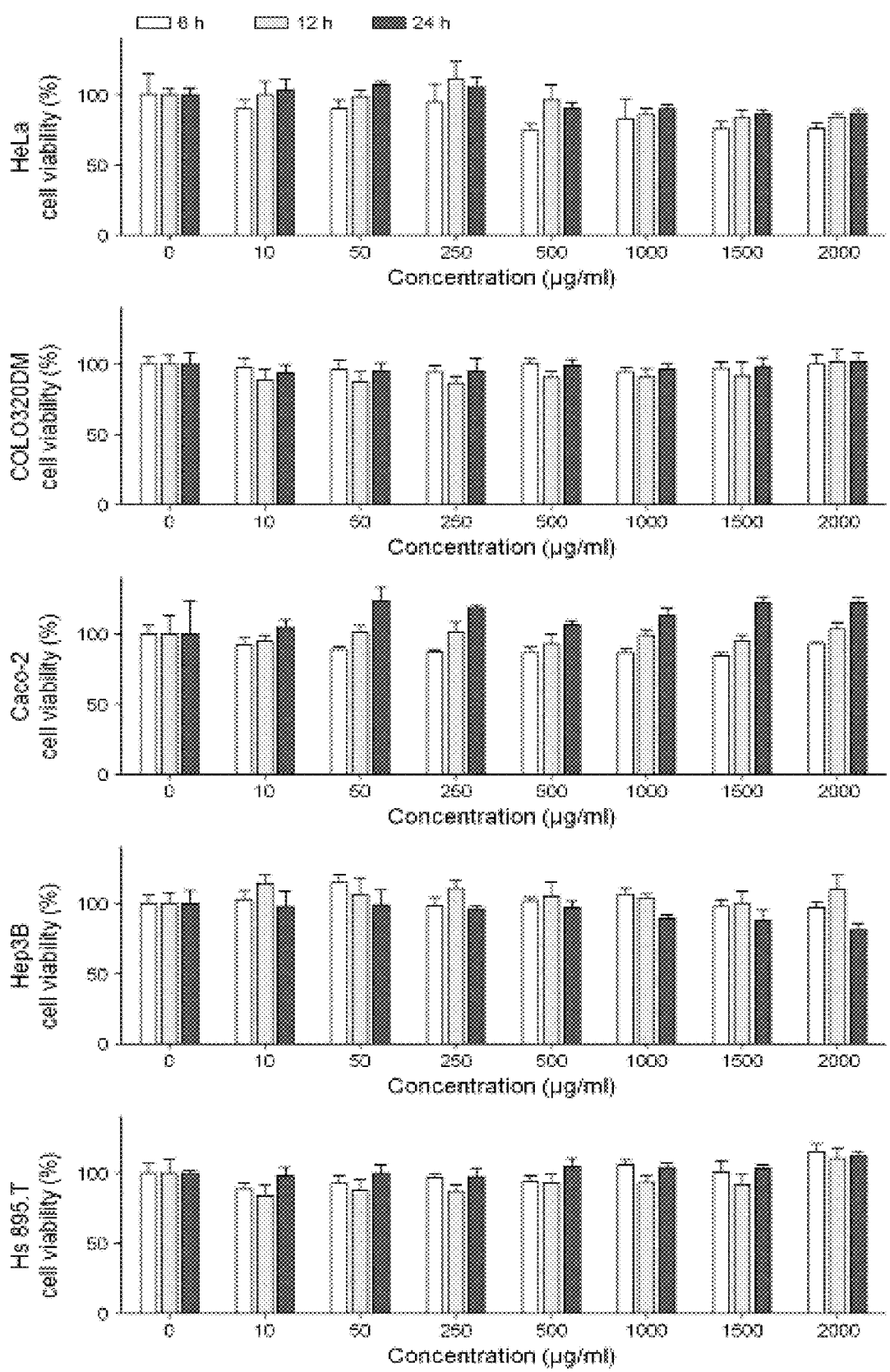

FIG. 19. Dose-dependent cytotoxicity of polydopamine in HeLa, COLO320DM, Caco-2, Hep3B, and HS 895.T cells. Cells were treated with polydopamine at various concentrations, and cytotoxicity was analyzed at different time points. Polydopamine is of low toxicity (>80% viability) in the concentration range of 0-2000 μg ml$^{-1}$ for all cell lines after 24 hour polydopamine exposure.

Figure 20A:
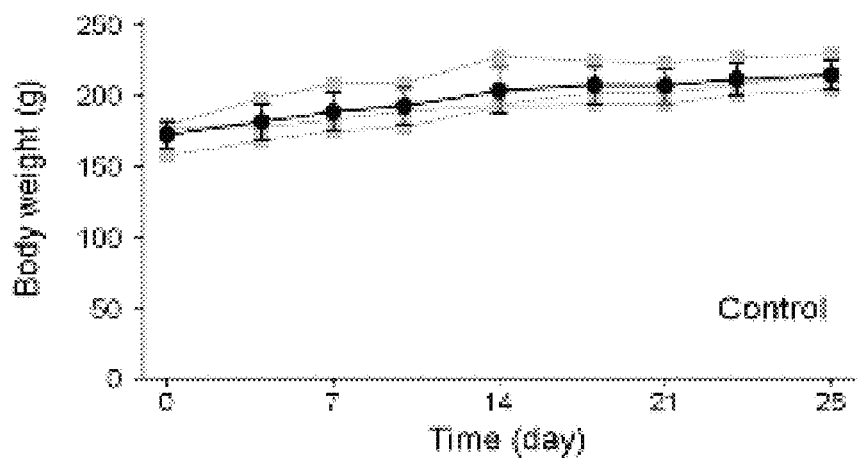
Figure 20B:
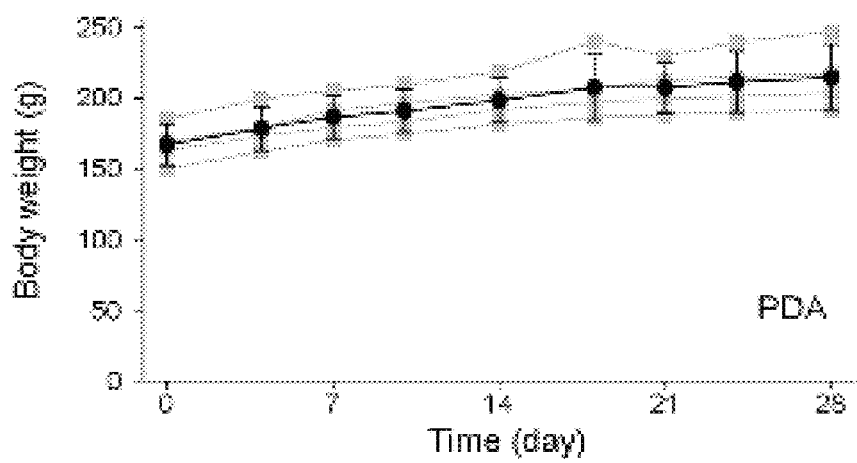
Figure 20C:
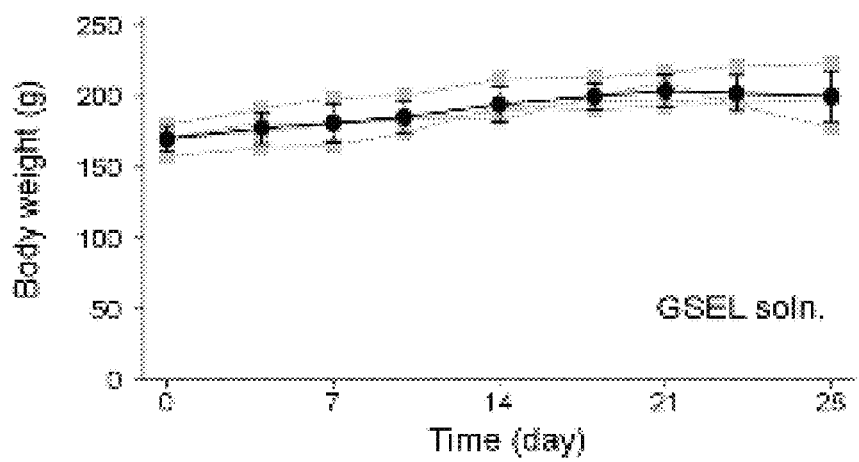

FIGS. 20A-20C. Body weight changes of rats during the 28-day oral toxicity evaluation. Rats were exposed to water (control) (FIG. 20A), as-prepared polydopamine (FIG. 20B), and the tissue-accelerated polymerization solution (FIG. 20C) separately over a period of 4 weeks. No significant differences in body weights were observed between rats exposed to the tissue-accelerated polymerization solution, polydopamine and water. Data was averaged between animals (each animal represented by a grey line) in each group (shown by the black line). Data are reported as means±SD over four animals.

FIG. 21. Hematological measurements of blood from rats after 28-day oral toxicity evaluation. Blood samples were collected from rats exposed to water (control), as-prepared polydopamine, and the tissue-accelerated polymerization solution. No significant differences in the hematological parameters were observed between rats (four replicates) exposed to the tissue-accelerated polymerization solution, polydopamine and water.

FIG. 22. Blood biochemistry tests of blood from rats after 28-day oral toxicity evaluation. Blood samples were collected from rats exposed to water (control), as-prepared polydopamine, and the tissue-accelerated polymerization solution. No significant differences in the blood biochemistry parameters were observed between rats (four replicates) exposed to the tissue-accelerated polymerization solution, polydopamine and water.

Figure 23:
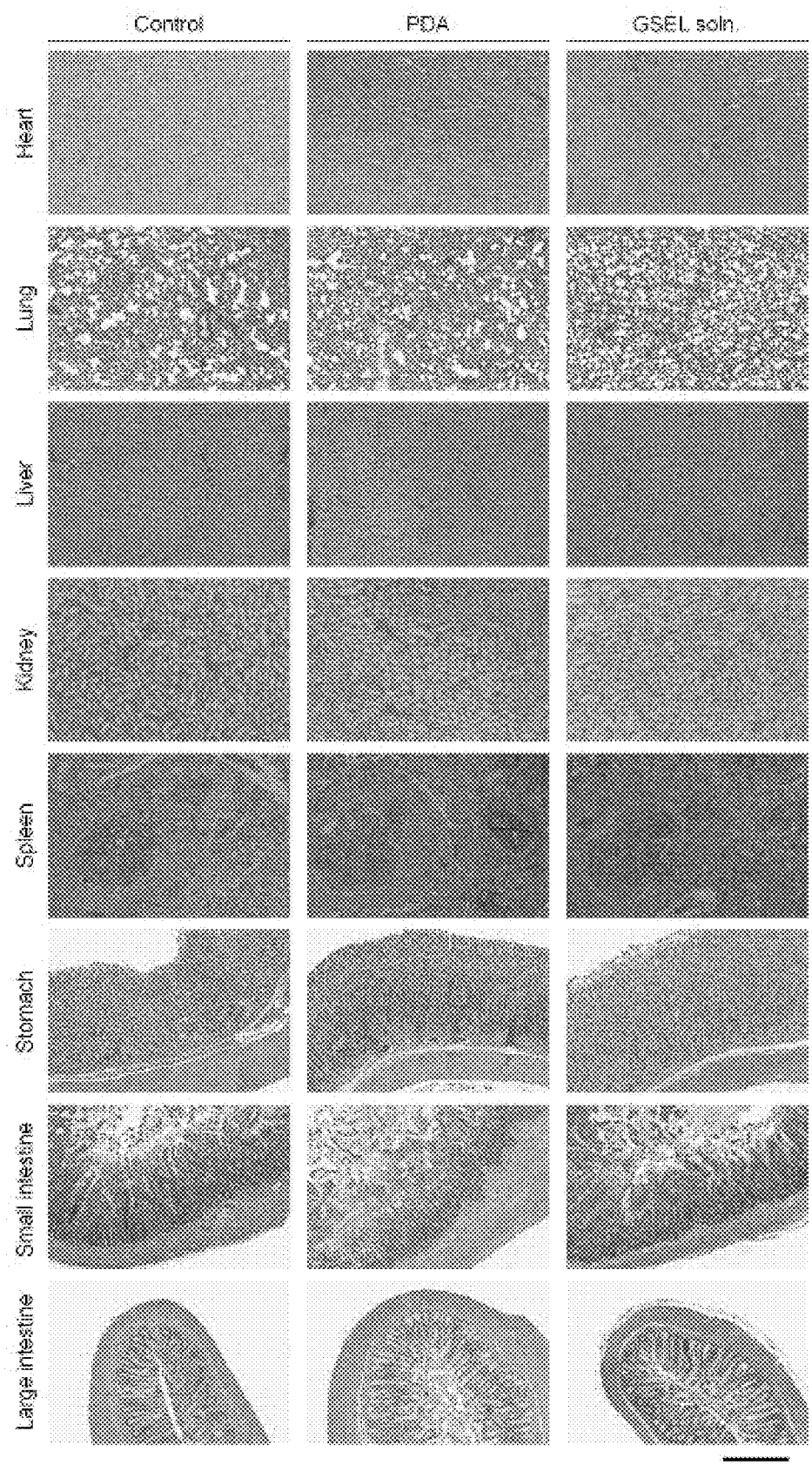

FIG. 23. Histology of the major organs collected from rats after 28-day oral toxicity evaluation. Tissues were collected from rats exposed to water (control), as-prepared polydopamine, and the tissue-accelerated polymerization solution separately. No noticeable organ damage was observed in polydopamine and tissue-accelerated polymerization solution treated rats compared to controls. Scale bar, 300 µm.

Figure 24B:
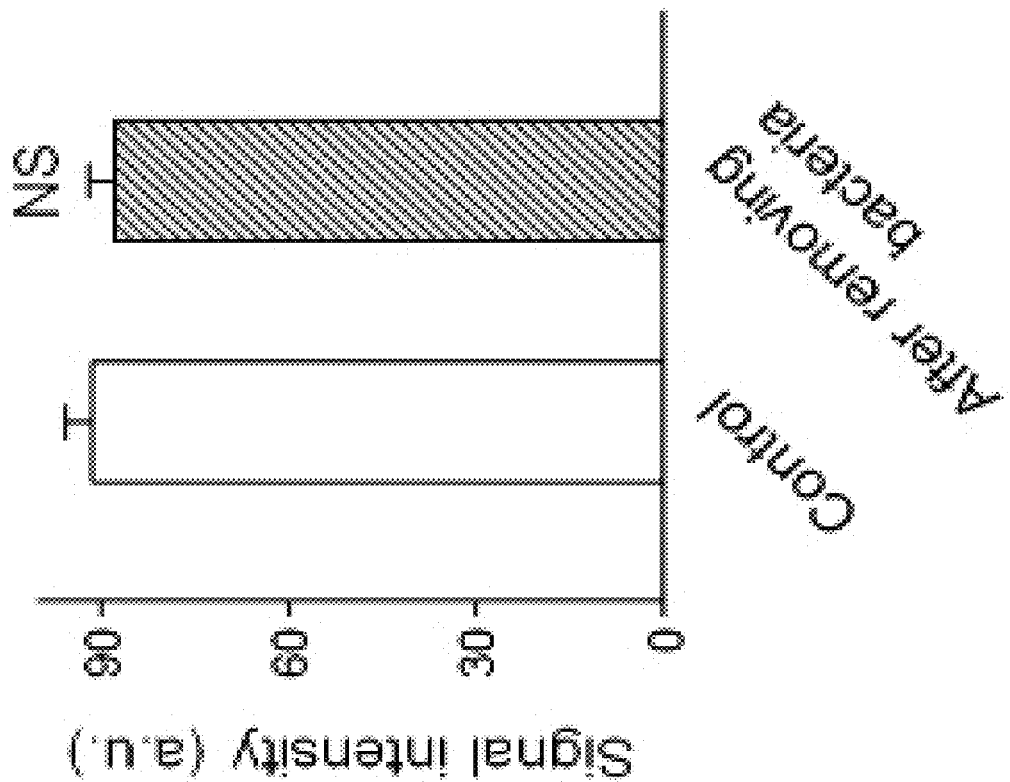
Figure 24A:
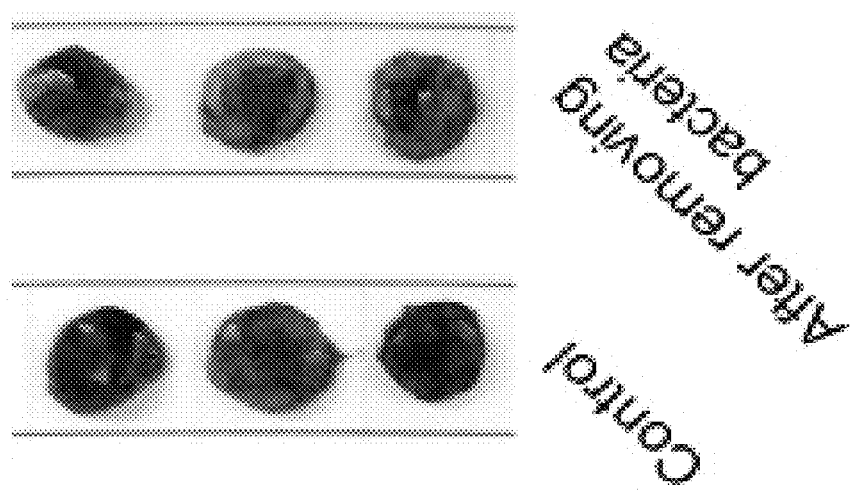

FIGS. 24A-24B. Evaluation of the tissue-accelerated polymerization performance on epithelium after removing bacterial present in the small intestinal mucus. Samples (6 mm in diameter) were collected at 3-5 random sites of polydopamine coated tissue, and images of the samples were analyzed for quantification of the polydopamine coating. ImageJ was used to identify regions of interest that included polydopamine coated tissues and excluded 'blank' tissue-free areas. Identical analysis was performed on all samples in each group to obtain an overall average polydopamine signal intensity and assess signal variation. This is an ex vivo study. FIG. 24A depicts images showing tissue samples (with and without removing bacteria) after the ex vivo tissue-accelerated polymerization. Samples (6 mm in diameter) were collected at three random sites of polydopamine coated tissue. Bacteria was removed from the luminal surface of epithelium by incubation with the antibiotic-antimycotic solution and repeated washing. FIG. 24B shows quantitative measurements of the polydopamine signal intensities of samples shown in FIG. 24A. The intensity differences are not statistically significant. P>0.05 by the two-tailed t-test. Data are reported as means±SD over three different tissue samples.

Figure 25:
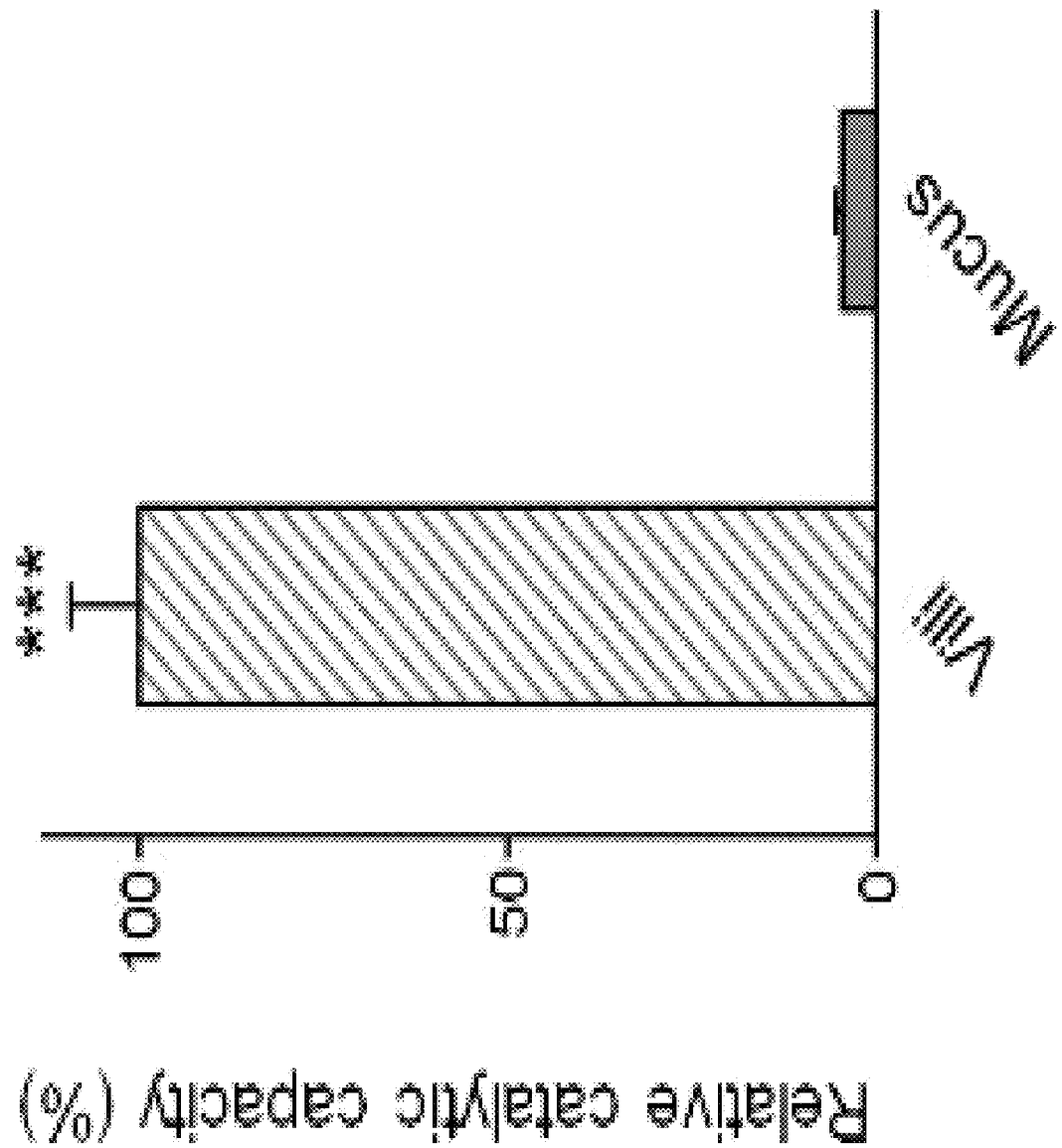

FIG. 25. Comparison of the catalase catalytic capacity between epithelium and mucus (bacteria). Solutions (180 µl) were prepared first and added into 96-well plates, followed by addition of 10 ul tissue lysates (villi or mucus). The reaction mixture was maintained at 37° C. for 20 minutes. Extinction of solutions at 700 nm was measured using a plate reader (Tecan). This is an ex vivo study. The relative catalytic capacity of intestinal villi (without bacteria) is higher than that of bacteria in the mucus. Mucus was collected on top of the epithelium (3 cm$^2$), and epithelial villi was collected from the same tissue area. Samples were diluted to the same volume for measurements. The capacity differences are statistically significant. ***P<0.001 by two-tailed t-test. Data are reported as means±SD over three different replicates.

Figure 26A:
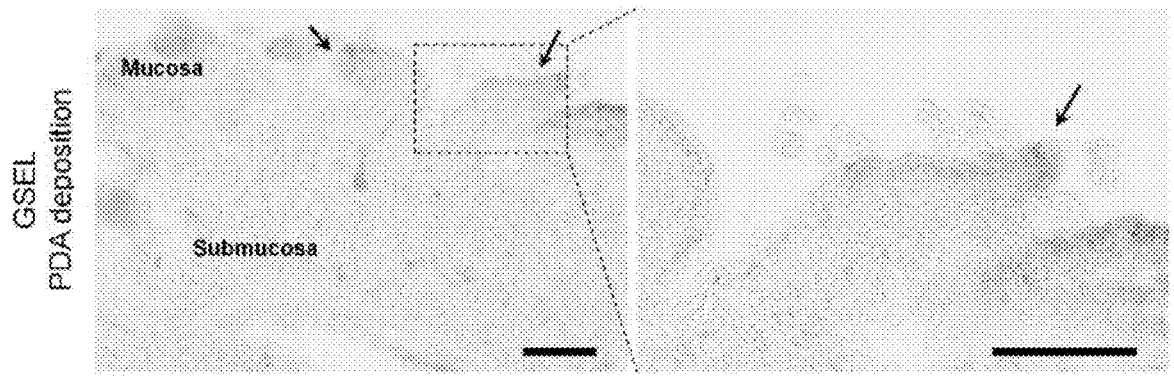
Figure 26B:
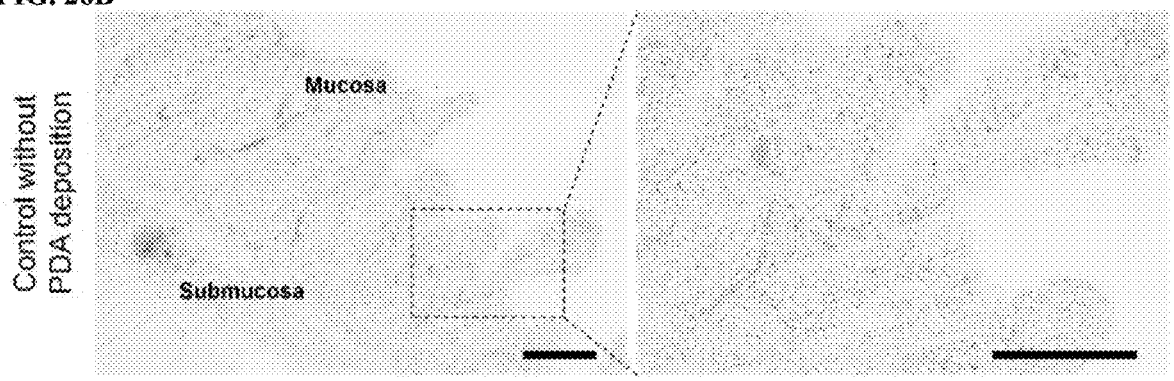
Figure 26C:
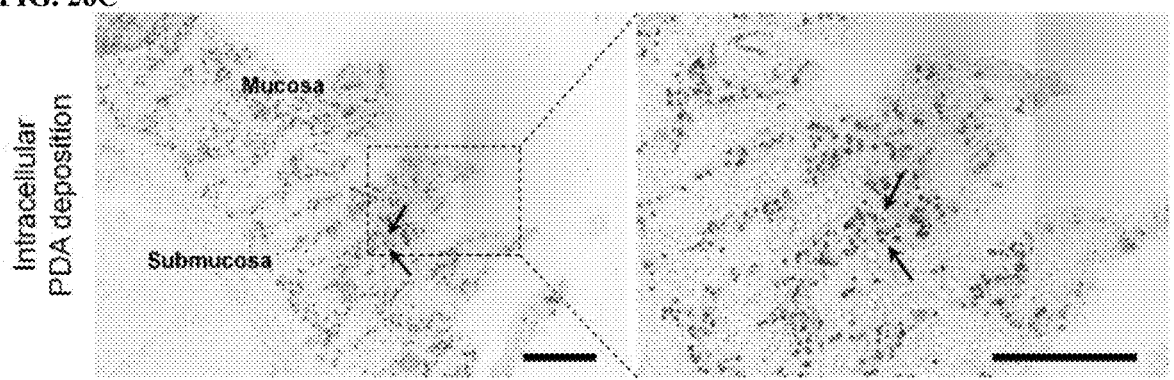

FIGS. 26A-26C. Microscopic analysis of polydopamine epithelial deposition. Tissues (12 cm$^2$) were exposed to the tissue-accelerated polymerization solution (10 ml) for 20 minutes and washed with PBS buffer (1×) 3 times to remove excess polydopamine. Polydopamine coated small intestines were snap-frozen and embedded in optimal cutting temperature (OCT) compound. The fixed tissues were cut into 40-µm-thick sections with a cryostat (Leica Biosystems). This is an ex vivo study. FIG. 26A shows bright-field imaging of tissue-accelerated polymerization coated tissue slices. The dark-brown polydopamine layer only deposited on the luminal surface of the epithelial cells (indicated by arrows), but not inside cells. FIG. 26B shows bright-field imaging of uncoated tissue slices. Light yellow background signals come from the blood vessels. FIG. 26C shows bright-field imaging of intracellular polydopamine deposition on the sectioned control tissue slices, where both dopamine and hydrogen peroxide molecules can diffuse freely and rapidly into the epithelial cells. Dark-brown polydopamine deposition (indicated by arrows) was observed inside the epithelial cells but not on the surface of the cells, and the deposition pattern is strikingly different relative to the tissue-accelerated polymerization coated tissue slices. Scale bars, 150 µm.

Figure 27:
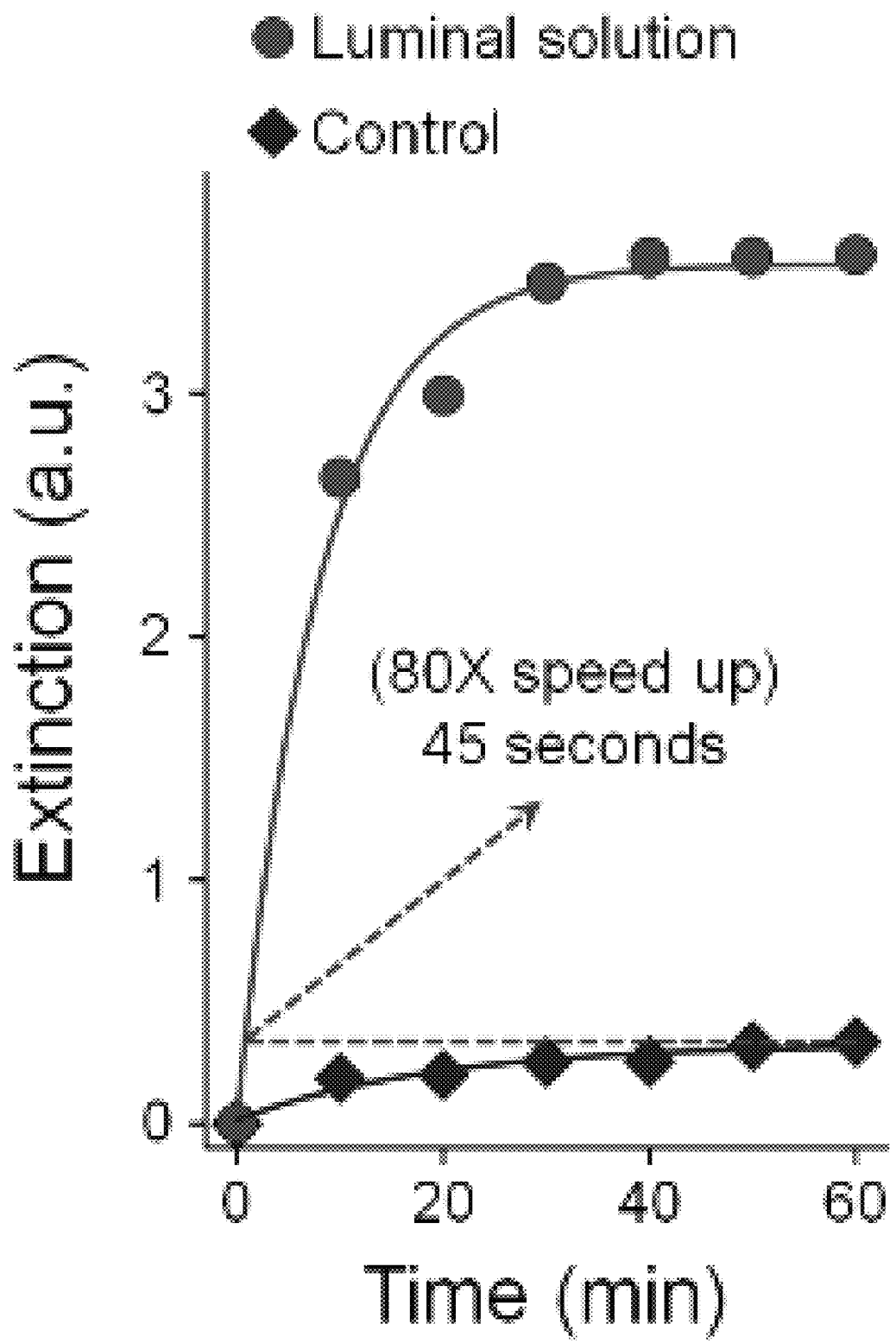

FIG. 27. Polydopamine polymerization kinetics in the luminal solution. The polydopamine polymerization kinetics were evaluated in the luminal solution localized on top of porcine epithelium through ex vivo studies. Extinction was measured at 700 nm for the samples undergoing polydopamine polymerization. The polydopamine polymerization kinetics in the tissue-accelerated polymerization (without epithelium catalysis) were used as the control. The optical extinction produced in 45 seconds under epithelium catalysis was the same as the extinction produced in 1 hour under the control condition.

Figure 28:
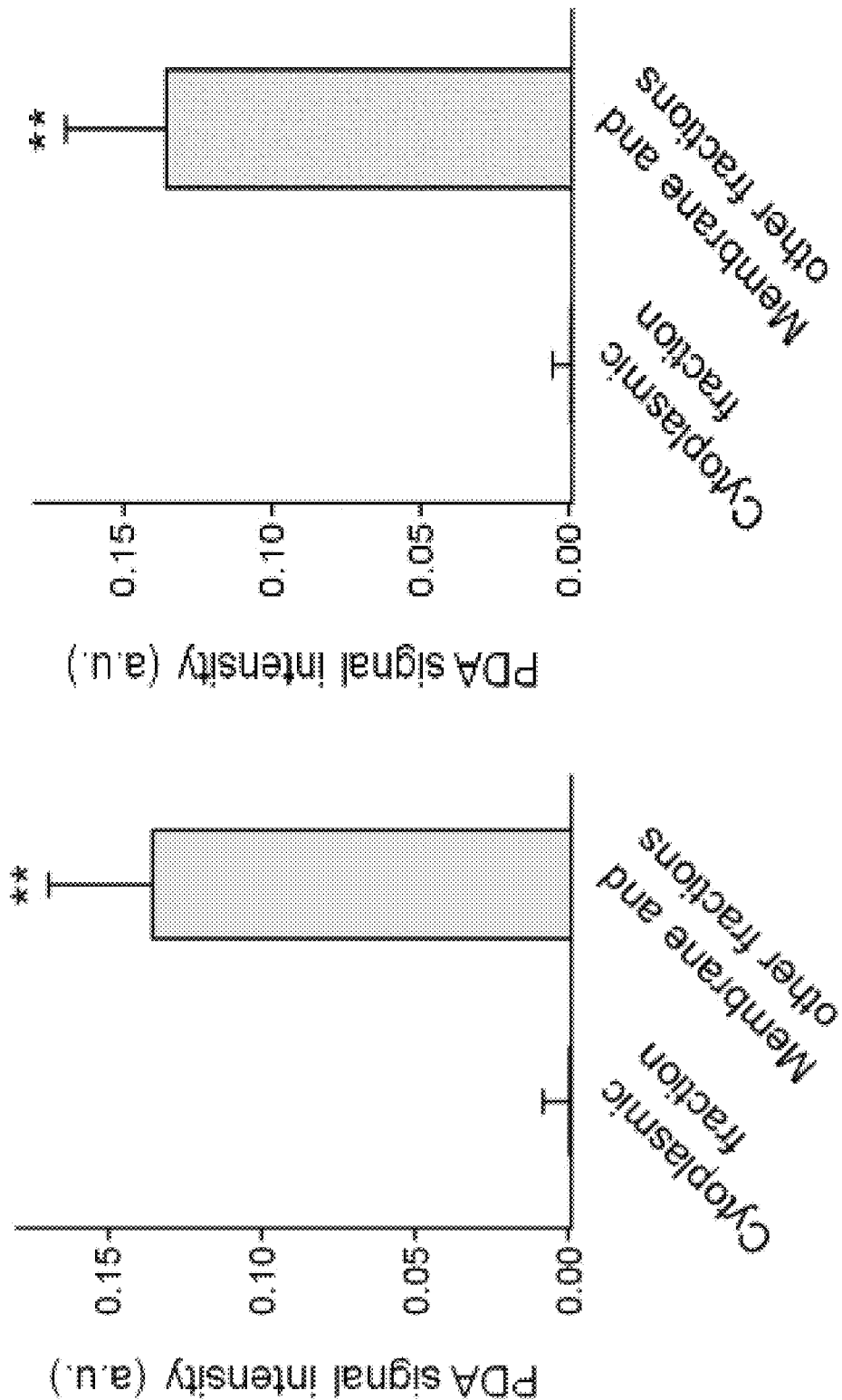

FIG. 28. Evaluation of polydopamine signals in different cellular fractionations. Cell fractionation was performed on tissue-accelerated polymerization coated villi. Villi was stripped off from the luminal surface of small intestinal tissue (opened lengthwise) placed on the ice-cold substrate. Polydopamine signals were evaluated by measuring the extinction of each cellular fraction at 700 nm. No polydopamine signal was detected in the cytoplasmic fraction, but clear polydopamine signal was detected in membrane and other fractions. The intensity differences are statistically significant. **P<0.01 by the two-tailed t-test. Data are reported as means±SD over three replicates.

Figure 29:
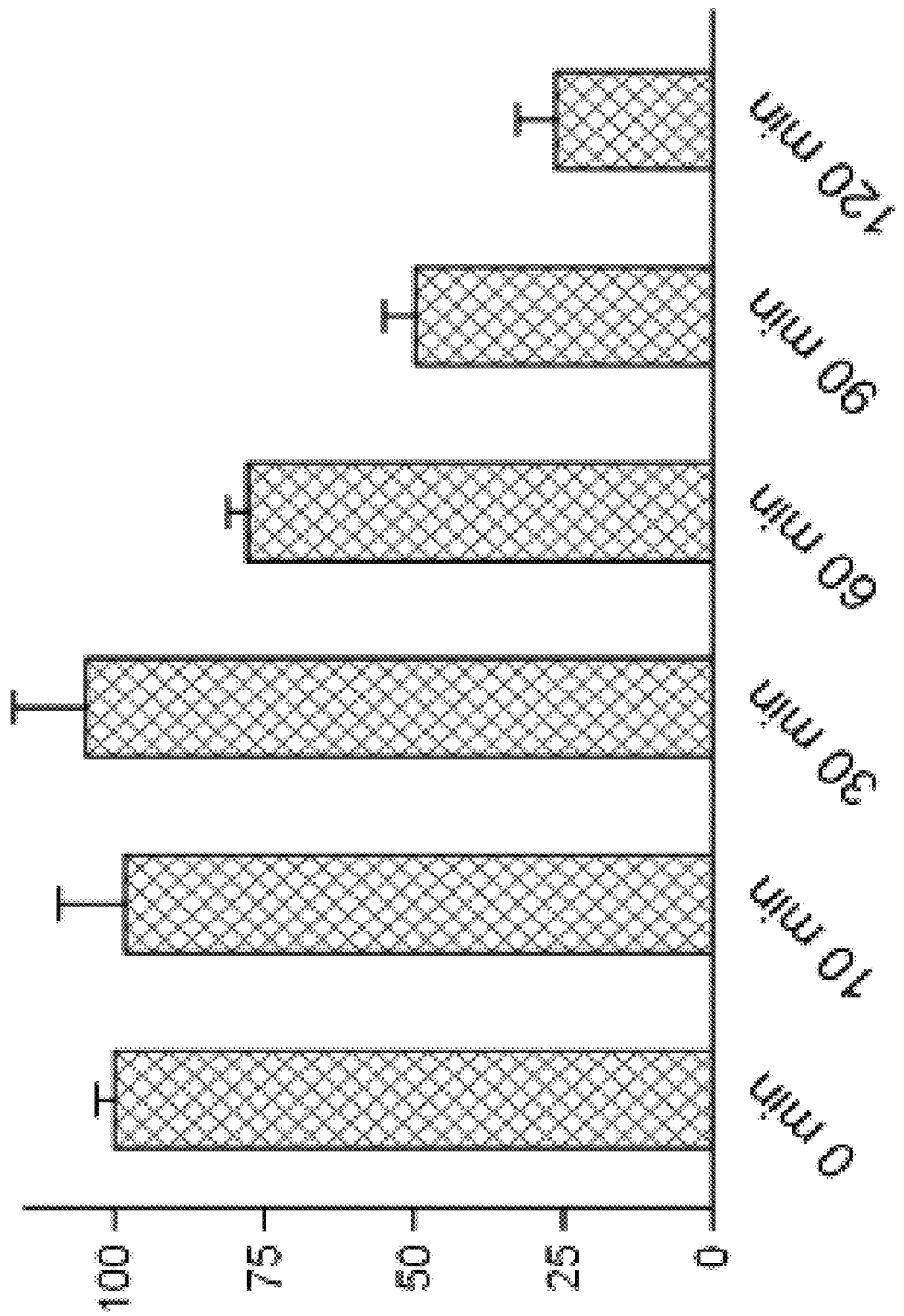

FIG. 29. Evaluation of the stability of the tissue-accelerated polymerization in the stomach. To evaluate the stability, the tissue-accelerated polymerization solution (dopamine (500 mg) and $H_2O_2$ (1 M, 1 mL) were rapidly added into Tris buffer (50 mM, 50 mL) at pH 8.5 and was used fresh) was administered to the pig (in vivo, non-crushing clamp was applied at the pylorus), retrieved from the stomach at different time points, and characterized through ex vivo coating studies. The relative coating performance shows that the retrieved solutions (from 10-30 minutes) showed consistent coating performance, and the relative coating efficiency drops only 30% after 60 minutes, demonstrating that both dopamine and hydrogen peroxide in the tissue-accelerated polymerization were not absorbed or consumed in the stomach in an significant amount. Data are reported as means±SD over three replicates.

Figure 30:
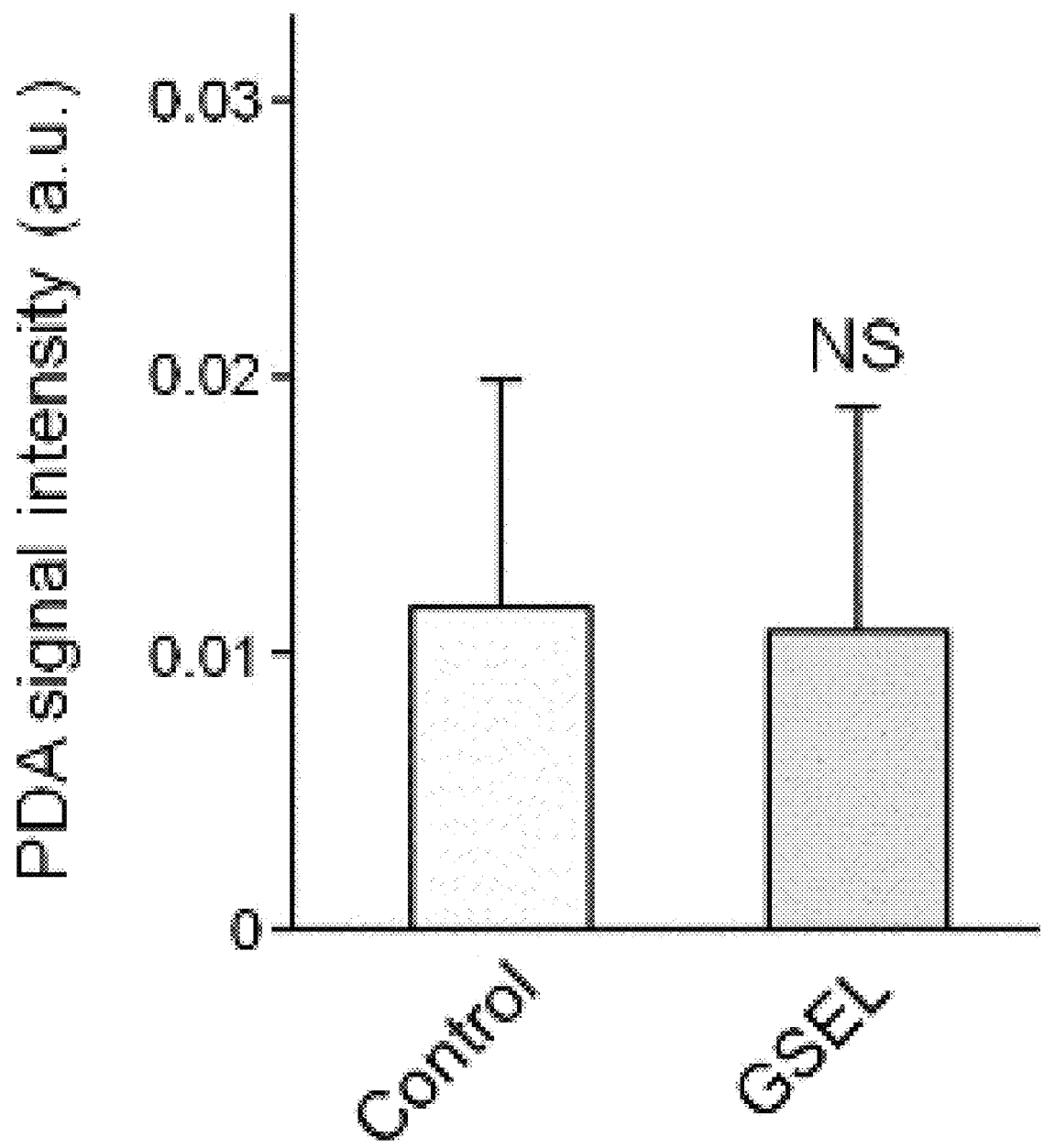

FIG. 30. Evaluation of the polydopamine signal in the submucosa. No detectable increase of polydopamine signal was observed in the porcine submucosa after in vivo tissue-accelerated polymerization. The solution consisted of dopamine (500 mg) and $H_2O_2$ (1 M, 1 mL). Both were rapidly added into Tris buffer (50 mM, 50 mL) at pH 8.5 and was used fresh. Epithelium tissues (without coating) were used as controls. The signal differences are not statistically significant. P>0.05 by the two-tailed t-test. Data are reported as means±SD over three replicates.

Figure 31A:
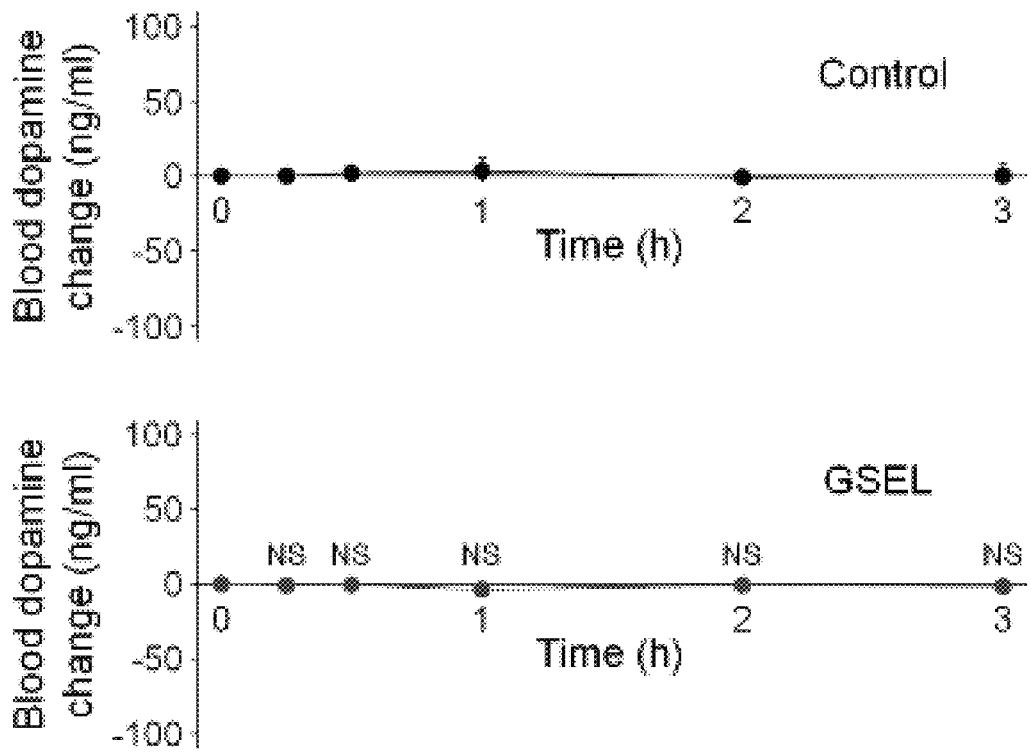
Figure 31B:
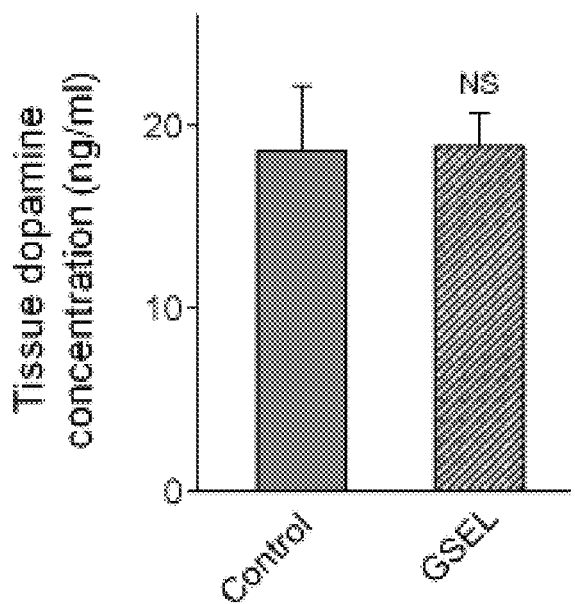
Figure 32A:
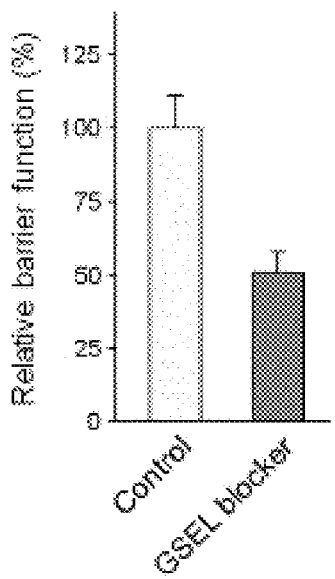
Figure 32B:
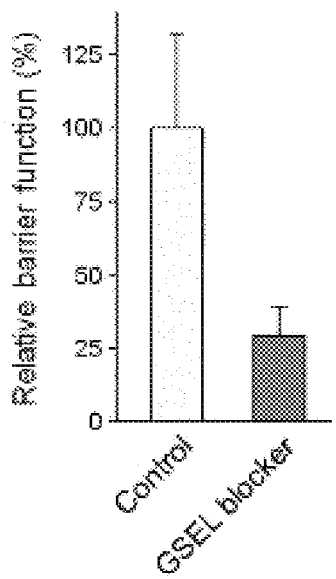
Figure 32C:
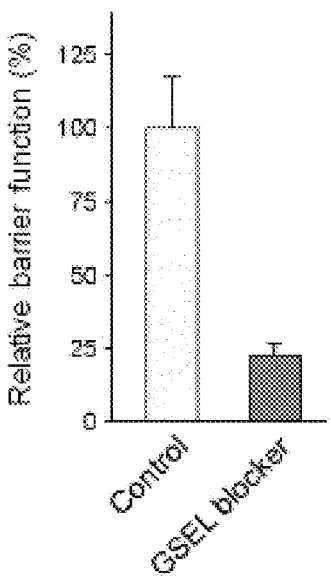
Figure 32D:
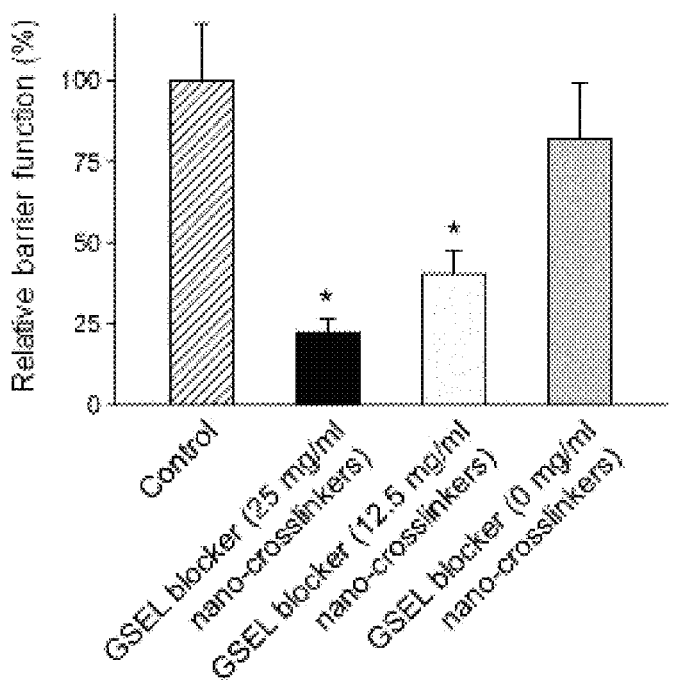

FIGS. 31A-31B. Evaluation of the dopamine concentration in the blood and submucosa through liquid chromatography-tandem mass spectroscopy. FIG. 31A shows that no obvious change of dopamine concentration was observed in the blood after in vivo administration of the tissue-accelerated polymerization solution (dopamine (500 mg) and $H_2O_2$ (1 M, 1 mL) were rapidly added into Tris buffer (50 mM, 50 mL) at pH 8.5 and was used fresh). P>0.05, two sample t test comparing tissue-accelerated polymerization and control groups (without tissue-accelerated polymerization) at matching time points. Data are reported as means±SD over three animals. FIG. 31B shows that no detectable increase of dopamine concentration was observed in the submucosa after administration of the tissue-accelerated polymerization solution (after 3 hours). The concentration differences are FIGS. 32A-32D. Evaluation of blocking efficiency of the tissue-accelerated polymerization layer through ex vivo studies. Tissues were exposed to the solution (Dopamine (500 mg) and $H_2O_2$ (1M, 1 ml) were rapidly added into Tris buffer (50 mM, 50 ml) at pH 8.5. The mixed solution was used fresh), and washed with PBS buffer (1×) 3 times to remove excess polydopamine. polydopamine nano-crosslinkers with different concentrations (25 mg/ml, 12.5 mg/ml, and 0 mg/ml) were suspended in the tissue-accelerated polymerization solution. This is an ex vivo study. FIGS. 32A-32C show relative barrier functions (tissue-penetration) of the tissue-accelerated polymerization layer on $Ca^{2+}$ (FIG. 32A), glutamic acid (FIG. 32B) and glucose (FIG. 32C). All three nutrients showed reduced tissue-penetration, with the three separate experiments showing tissue-accelerated polymerization barrier blocking ~49% of $Ca^{2+}$, ~71% of glutamic acid, and ~78% of glucose. FIG. 32D shows relative barrier functions (glucose tissue-penetration) of the tissue-accelerated polymerization layer (with different crosslinking densities). When fewer nano-crosslinkers were incorporated into the coating layer, glucose had normal tissue-penetration levels, demonstrating that the polydopamine coating layer itself did not affect cellular glucose absorption but the crosslinking density of the coating layer modulated the glucose absorption efficiency. Porcine small intestinal tissues (without coating) were used as controls. .*$P<0.05$ (versus control), one-way analysis of variance (ANOVA) and post hoc Bonferroni. Data are reported as means±SD over three replicates.

Figure 33:
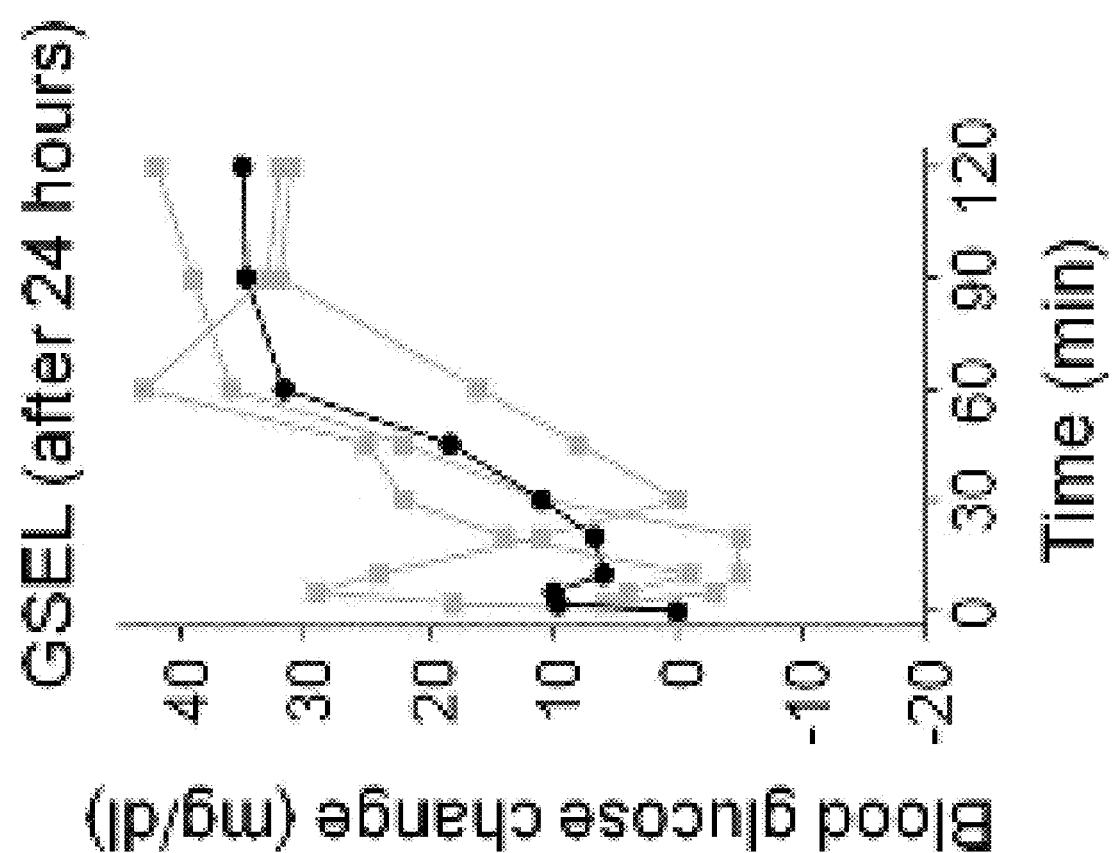

FIG. 33. Evaluation of glucose absorption restoring of tissue-accelerated polymerization animals. Polydopamine nano-crosslinkers (25 mg/ml) were first suspended in the tissue-accelerated polymerization solution. Pigs were orally administered the nano-crosslinker suspended tissue-accelerated polymerization solution (10 ml/kg), and introduced into the small intestine. The solution was directly administered to the small intestine through a catheter under endoscopic visual guidance. This is an ex vivo study. An oral glucose tolerance test was performed 24 hours after pigs received tissue-accelerated polymerization coating. Pigs with the tissue-accelerated polymerization coating recovered normal glucose absorption after 24 hours, demonstrating that the tissue-accelerated polymerization coating layer is transient. Data was averaged between animals (each animal represented by a grey line) in each group (shown by the black line).

Figure 34:
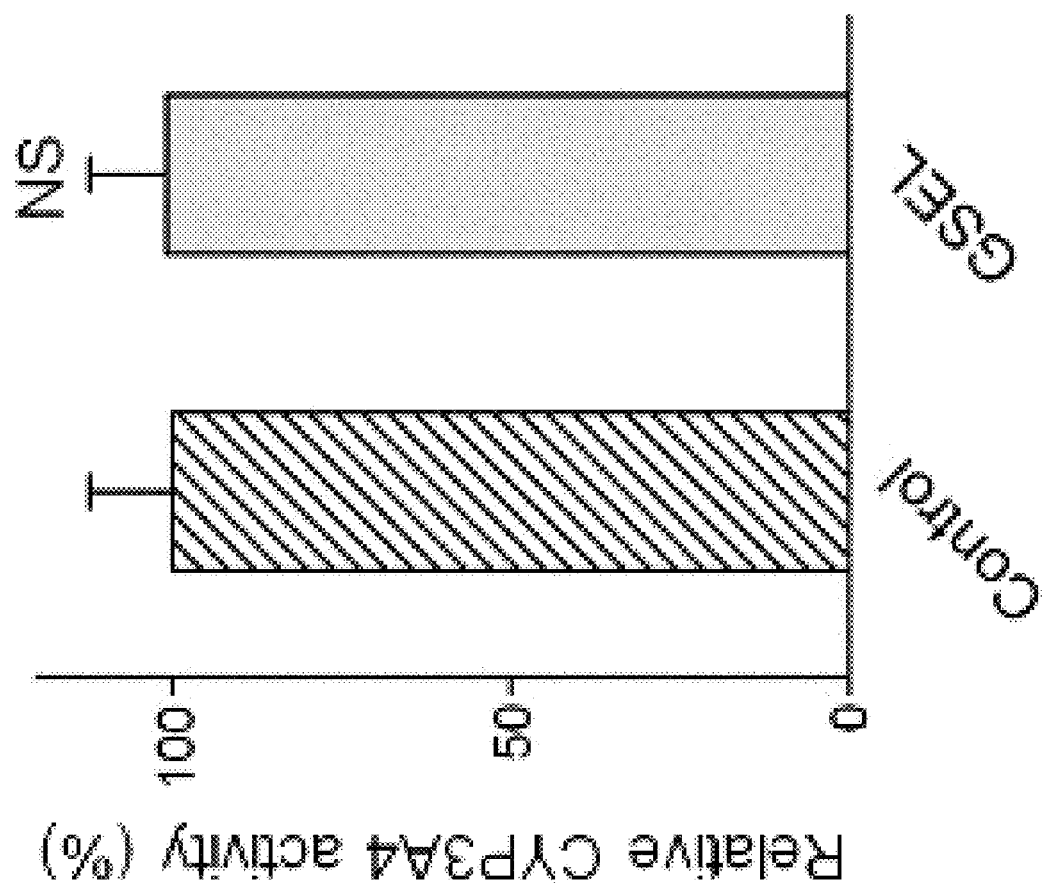

FIG. 34. Evaluation of the CYP450 activity of epithelium with and without the polydopamine coating layer. Tissues (12 $cm^2$) were exposed to the tissue-accelerated polymerization solution (10 ml) for 20 minutes and washed with PBS buffer (1×) 3 times to remove excess polydopamine. This is an ex vivo study. No change of CYP3A4 activity was observed in epithelium after the tissue-accelerated polymerization. Epithelium tissues (without coating) were used as controls. The activity differences are not statistically significant. $P>0.05$ by the two-tailed t-test. Data are reported as means±SD over five replicates.

Figure 35B:
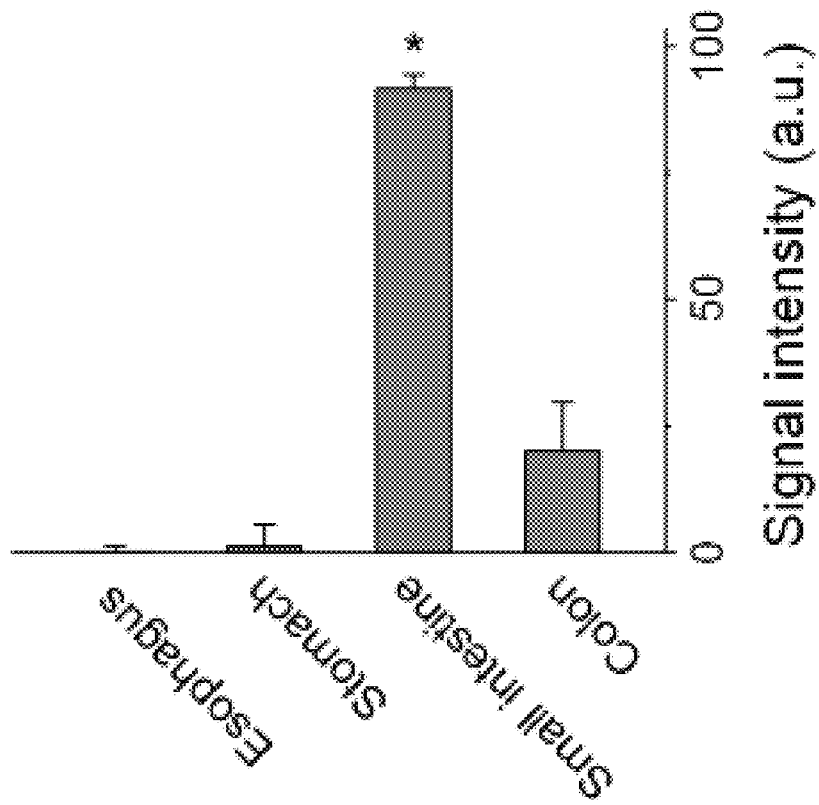
Figure 35A:
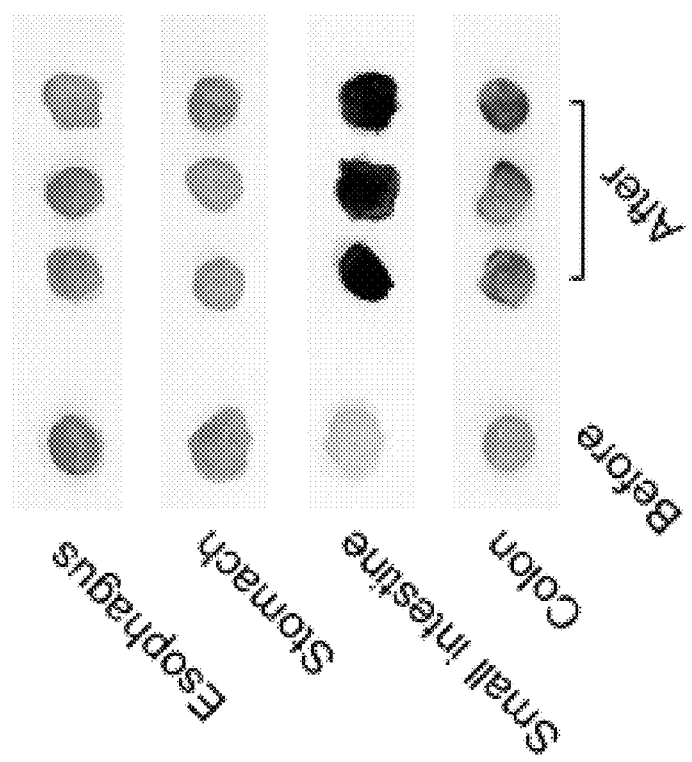

FIGS. 35A-35B. Tissue-accelerated polymerization pattern in the human GI tract. Tissues (12 $cm^2$) were exposed to the tissue-accelerated polymerization solution (10 ml) for 20 minutes and washed with PBS buffer (1×) 3 times to remove excess polydopamine. This is an ex vivo study. FIG. 35A depicts images showing human tissue samples in different parts of the GI tract before and after applying the tissue-accelerated polymerization coating ex vivo. Samples (6 mm in diameter) were collected at three random sites of polydopamine coated tissue. FIG. 35B shows quantitative measurements of the polydopamine signal intensities of samples shown in FIG. 35B. The intensity differences between the small intestine and other tissue are statistically significant. *$P<0.05$, one-way analysis of variance (ANOVA) and post hoc Bonferroni. Data are reported as means±SD over three different tissue samples.

FIGS. 36A-36C. Stability of the surface-based polydopamine coating. Polydopamine coating was applied on the surface of impermeable polycarbonate substrate. Polycarbonate sheets were exposed to the tissue-accelerated polymerization solution (without $H_2O_2$) for 36 hours and washed with water to remove excess polydopamine. The white color polycarbonate (left) turned into a dark-brown color after the polydopamine coating (right). The stability of the polydopamine coating was evaluated in a series of physical conditions). FIGS. 36A-36C show that no obvious polydopamine signal reduction was observed under both gentle and vigorous scratching, and the polydopamine coating was only removed under extremely vigorous scratching with sandpaper. These results demonstrated that the stability of surface-based polydopamine coating is due to strong surface-based adhesion, rather than penetration into the substrate surface.

Figure 37:
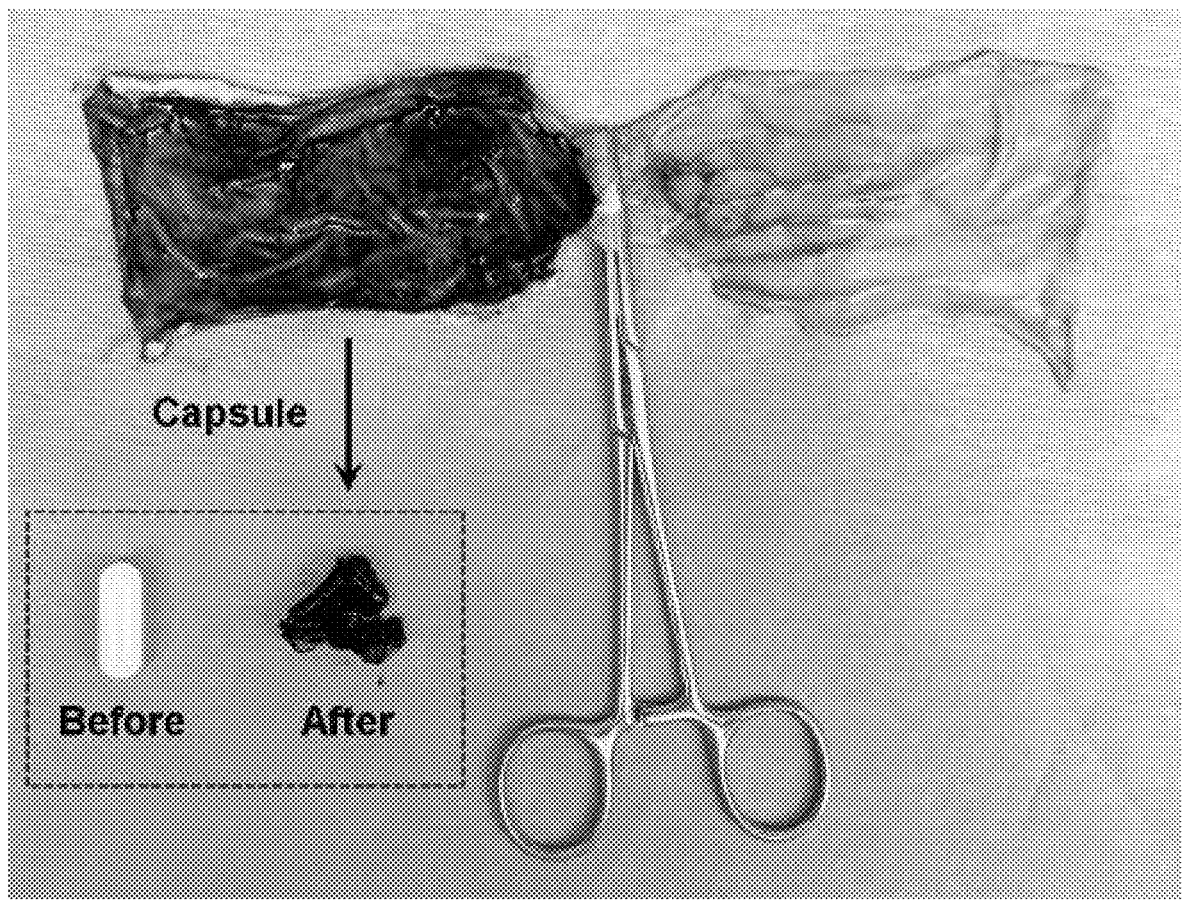

FIG. 37. Translation of the tissue-accelerated polymerization platform into capsules. The isolated porcine small intestinal tissue from in vivo showed different polydopamine coating before and after the clamp site, demonstrating the coating performance of tissue-accelerated polymerization capsules. The capsule consisted of dopamine hydrochloride powder (500 mg), Tris powder (30-300 mg; 300 mg), solid urea $H_2O_2$ powder (10-50 mg; 50 mg). The mixed powder was filled into (size 000) capsule. The capsule was administrated directly into the intestine by surgically opening a hole on the intestine for capsule delivery. Capsules did not pass down to the lower small intestine due to the small intestinal ligation. After releasing tissue-accelerated polymerization ingredients, capsules collapsed, dissolved and broke into smaller pieces.

DEFINITIONS

Unless otherwise required by context, singular terms shall include pluralities, and plural terms shall include the singular.

The language "in some embodiments" and "in certain embodiments" are used interchangeably.

The following definitions are more general terms used throughout the present application:

The singular terms "a," "an," and "the" include plural references unless the context clearly indicates otherwise. Similarly, the word "or" is intended to include "and" unless the context clearly indicates otherwise.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2%, or 1% of a given value or range of values.

When a range of values ("range") is listed, it is intended to encompass each value and sub-range within the range. A range is inclusive of the values at the two ends of the range unless otherwise provided.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "administer," "administering," or "administration" refers to implanting, absorbing, ingesting, injecting, inhaling, or otherwise introducing a composition described herein or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a polymer or composition described herein refers to an amount sufficient to elicit the desired biological response. An effective amount of a polymer or composition described herein may vary depending on such factors as the desired biological endpoint, the pharmacokinetics of the polymer or composition, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound, polymer, or composition described herein in a single dose. In certain embodiments, an effective amount is the combined amounts of a compound, polymer, or composition described herein in multiple doses.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes.

The term "polymer" refers to a compound comprising eleven or more covalently connected repeating units. In certain embodiments, a polymer is naturally occurring. In certain embodiments, a polymer is synthetic (i.e., not naturally occurring).

The term "nanoparticle" refers to a particle having an average (e.g., mean) dimension (e.g., diameter) of between about 1 nanometer (nm) and about 1 micrometer ($\mu$m) (e.g., between about 1 nm and about 300 nm, between about 1 nm and about 100 nm, between about 1 nm and about 30 nm, between about 1 nm and about 10 nm, or between about 1 nm and about 3 nm), inclusive.

As used herein, the term "agent" means a molecule, group of molecules, complex or substance administered to an organism for diagnostic, therapeutic, preventative medical, or veterinary purposes. In certain embodiments, the agent is an active pharmaceutical ingredient agent, a diagnostic agent, or a prophylactic agent). In certain embodiments, the polymers and compositions disclosed herein comprise an agent(s), e.g., a first agent (e.g., at least one (including, e.g., at least two, at least three). In some embodiments, the polymers and compositions can further comprise a second agent. In some embodiments, the agent is an enzyme (e.g., a digestive enzyme), a nutrient blocker (e.g., a crosslinking agent), a diagnostic agent, a nutraceutical, a radioprotective agent, an active pharmaceutical ingredient, or a combination thereof.

As used herein, the term "radioprotective agent" means an agent that protects biological systems exposed to radiation, either naturally or through radiation leakage. In certain embodiments, radioprotective agents protect normal cells from radiation injury in cancer patients undergoing radiotherapy As used herein, the term "diagnostic agent" means an imaging agent or contrast agent. The terms "imaging agent" and "contrast agent" refer to a substance used to enhance the contrast of structures or fluids within the body in medical imaging. It is commonly used to enhance the visibility of blood vessels and the gastrointestinal tract in medical imaging.

As used herein, the term "active pharmaceutical ingredient" includes an agent that is capable of providing a local or systemic biological, physiological, or therapeutic effect in the biological system to which it is applied. For example, an active pharmaceutical ingredient can act to control tumor growth, control infection or inflammation, act as an analgesic, promote anti-cell attachment, and enhance bone growth, among other functions. Other suitable active pharmaceutical ingredients can include anti-viral agents, hormones, antibodies, or therapeutic proteins. Other active pharmaceutical ingredients include prodrugs, which are agents that are not biologically active when administered but, upon administration to a subject are converted to biologically active agents through metabolism or some other mechanism.

An active pharmaceutical ingredient can be a compound, e.g., small organic or inorganic molecules; saccharines;

oligosaccharides; polysaccharides; biological macromolecule, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

Examples of active pharmaceutical ingredients include, but are not limited to, antimicrobial agents, analgesics, antiinflammatory agents, counterirritants, coagulation modifying agents, diuretics, sympathomimetics, anorexics, antacids and other gastrointestinal agents; antiparasitics, antidepressants, anti-hypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, parasympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable active pharmaceutical ingredients include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

DETAILED DESCRIPTION OF CERTAIN EMBODIMENTS

Before the disclosed systems, compositions, methods, uses, and kits are described in more detail, it should be understood that the aspects described herein are not limited to specific embodiments, methods, systems, apparati, or configurations, and as such can, of course, vary. It is also to be understood that the terminology used herein is for the purpose of describing particular aspects only and, unless specifically defined herein, is not intended to be limiting.

In general, polydopamine polymerization is a slow process, of which the reaction rate is limited by low oxygen levels in normal dopamine-oxidation conditions[11]. However, the inventors unexpectedly discovered that defensive oxygen production via endogenous catalase decomposition of hydrogen peroxide (known as the cellular anti-oxidation effect) boosts oxygen release for dopamine oxidation, and dramatically increases the rate of dopamine polymerization. FIG. 1A shows a schematic representation of an embodiment of the present disclosure wherein an oral monomer solution containing dopamine monomers and hydrogen peroxide is administered to a subject. The solution flows uninhibited on the surface of the gastrointestinal mucosa, and the hydrogen peroxide molecules diffuse freely between the epithelial tissue and the dopamine solution. However, dopamine remains in solution due to its slow diffusion and transport. The hydrogen peroxide diffuses into epithelial cells and is rapidly broken down by intracellular catalase into oxygen, which is released out of the cells and mixed with extracellular monomers. These monomers near the epithelial surface are rapidly oxidized into oligomers, and further into polymers, that crosslink with biomolecules exposed outside epithelium, forming a thin, strong polydopamine coating layer on the tissue. Unreacted monomers in the solution and unbound polydopamine are washed away from the epithelium. This type of tissue surface-initiated polymeric coating avoids potential bowel adhesions and obstructions, which are frequently induced by bulk-crosslinking-based sealants or other conventional tissue adhesives[13]. The catalytic polydopamine polymerization primarily occurs in the small intestine, which is due to higher expression levels of catalase in the small intestine relative to other parts of the gastrointestinal tract, including the esophagus, stomach and large intestine. Thus, specific small intestine targeting is spontaneously enabled due to an uneven distribution of natural enzymes along the digestive tract.

The inventors performed a series of investigations related to the compositions, methods, and kits disclosed herein. The inventors used various techniques, including endoscopic examination, intestinal ligation, and X-ray imaging, which consistently showed the robustness of this subject matter, demonstrating features (prolonged but transient intestinal residence) of the in situ formed polymer. In addition, the inventors did not observe any clinical, endoscopic, or radiographic evidence of gastrointestinal perforation, inflammation, or obstruction in connection with the use of the compositions, methods, and kits of the present disclosure. The biocompatibility of certain compositions of the present disclosure was carefully characterized by following guidelines issued by Organization for Economic Co-operation and Development (OECD) and confirming the absence of oral toxicity.

Methods and Uses

In one aspect, the disclosure provides a method of forming a polymer in situ in a subject, the method comprising administering to a subject a composition comprising a monomer and an oxygen source, wherein the monomer and the oxygen source contact a catalyst endogenous to the subject and the catalyst polymerizes the monomer, wherein the monomer is dopamine, or salt thereof, the oxygen source is hydrogen peroxide or urea hydrogen peroxide, and endogenous catalyst is selected from a catalase or a peroxidase.

In some embodiments, the endogenous catalyst is a peroxidase. In certain embodiments, the peroxidase is eosinophil peroxidase, lactoperoxidase, or myeloperoxidase.

In some embodiments, the endogenous catalyst is a catalase. In some embodiments, the catalase is a bacterial catalase. In some embodiments, the catalase is a human catalase.

In some embodiments, the endogenous catalyst is located in the gastrointestinal (GI) tract of the subject. In some embodiments, the endogenous catalyst is located in the upper GI of the subject. In some embodiments, the endogenous catalyst is located in the gut of the subject. In some embodiments, the endogenous catalyst is located in the stomach of the subject.

In some embodiments, the endogenous catalyst is located in a cell. In some embodiments, the endogenous catalyst is located in a blood cell. In some embodiments, the endogenous catalyst is located on a cell. In some embodiments, the endogenous catalyst is located on a blood cell. In some embodiments, the endogenous catalyst is located in a cell. In some embodiments, the endogenous catalyst is secreted by a blood cell. In some embodiments, the endogenous catalyst is located on a cell. In some embodiments, the endogenous catalyst is secreted by a blood cell.

In some embodiments, the composition further comprises an enzyme, a nutrient blocker, a radioprotective agent, a nutraceutical, an active pharmaceutical ingredient, a diagnostic agent, or a combination thereof. In some embodiments, the composition further comprises an enzyme. In some embodiments, the composition further comprises a nutrient blocker. In some embodiments, the composition further comprises a radioprotective agent. In some embodiments, the composition further comprises an active pharmaceutical ingredient. In some embodiments, the composition further comprises a diagnostic agent. In some embodiments, the composition further comprises a combination of two or more of enzymes, nutrient blockers, a nutraceutical, radioprotective agents, active pharmaceutical ingredients, and diagnostic agents.

In some embodiments, the oxygen source is hydrogen peroxide. In some embodiments, the oxygen source is urea hydrogen peroxide.

In some embodiments, at least one of the monomer and the oxygen source is stable in the stomach of the subject. In some embodiments, at least one of the monomer and the oxygen source is stable in the stomach for at least 30 minutes of the subject. In some embodiments, at least one of the monomer and the oxygen source is stable in the stomach for at least 60 minutes of the subject.

In some embodiments, the composition is stable in the stomach of the subject. In some embodiments, the composition is stable in the stomach for at least 30 minutes of the subject. In some embodiments, the composition is stable in the stomach for at least 60 minutes of the subject.

In some embodiments, at least one of the monomer and the oxygen source is stable in that it does not decompose in the stomach of the subject. In some embodiments, at least 95% of at least one of the monomer and the oxygen source remains after the composition passes out of the stomach of the subject. In some embodiments, at least 90% of at least one of the monomer and the oxygen source remains after the composition passes out of the stomach of the subject. In some embodiments, at least 80% of at least one of the monomer and the oxygen source remains after the composition passes out of the stomach of the subject.

In some embodiments, the composition comprises about 0.001 to about 1000 mg/mL dopamine. In some embodiments, the composition comprises about 0.01 to about 100 mg/mL of dopamine. In some embodiments, the composition comprises about 0.01 to about 50 mg/mL of dopamine. In some embodiments, the composition comprises about 1 to about 20 mg/mL of dopamine. In some embodiments, the composition comprises 10 mg/mL of dopamine. In some embodiments, the composition comprises 9.8 mg/mL of dopamine.

In some embodiments, the composition comprises about 0.01 to about 100 mM of the oxygen source. In some embodiments, the composition comprises about 0.1 to about 50 mM of the oxygen source. In some embodiments, the composition comprises about 1 to about 30 mM of the oxygen source. In some embodiments, the composition comprises about 20 mM of the oxygen source.

In some embodiments, the composition comprises a concentration of oxygen source compatible with ingestion by the subject.

In certain embodiments, the composition further comprises a buffer.

In some embodiments, the composition has a pH of about 7 to about 10. In some embodiments, the composition has a pH of about 7 to about 9. In some embodiments, the composition has a pH of about 8.5. In some embodiments, the composition has a pH of about 7.4.

In some embodiments, the composition is administered by a route selected from oral, rectal, injection, sublingual, buccal, vaginal, ocular, otic, inhalation, or cutaneous. In some embodiments, the composition is administered orally. In certain embodiments, the composition is administered by intra-articular injection. In certain embodiments, the composition is administered topically. In certain embodiments, the composition is administered dermally. In certain embodiments, the composition is administered ophthalmically.

In some embodiments, the composition is administered via a scope. In certain embodiments, the composition is administered via an endoscope, arthroscope, cystoscope, colposcope, colonoscope, bronchoscope, ureteroscope, anoscope, esophagoscope, gastroscope, laparoscope, laryngoscope, neuroendoscope, proctoscope, sigmoidoscope, or thoracoscope.

In some embodiments, the composition is a liquid or a solid dosage form.

In some embodiments, the composition is in the form of a solution, a gel, a tablet, a powder, a capsule, eye drops, or a transdermal patch. In some embodiments, the composition is in the form of a solution, a gel, a tablet, or a capsule. In some embodiments, the composition is in the form of a solution. In some embodiments, the composition is in the form of eye drops. In some embodiments, the composition is in the form of a powder. In some embodiments, the composition is in the form of a transdermal patch.

In certain embodiments, the polymer forms in contact with and adheres to a tissue in the subject. In some embodiments, the polymer adheres to a tissue of the subject. In certain embodiments, the tissue is epithelium. In some embodiments, the epithelium is intestinal epithelium.

In some embodiments, the location of polymer formation is based on expression levels of the catalyst. In certain embodiments, the polymer forms substantially on a particular tissue based on high expression levels of catalyst. In some embodiments, the polymer does not substantially form on a particular tissue due to low expression levels of catalyst. In some embodiments, the location of polymer formation is based on expression levels of catalase. In certain embodiments, the polymer forms substantially on a particular tissue based on expression levels of catalase. In some embodiments, the polymer does not substantially form on a particular tissue due to low expression levels of catalase.

In certain embodiments, the tissue is epithelium. In some embodiments, the polymer forms on and adheres to the epithelium of the subject. In some embodiments, the polymer forms in contact with the epithelium of the subject. In some embodiments, the epithelium is intestinal epithelium. In some embodiments, the polymer forms on the small intestine. In certain embodiments, the polymer forms in the lumen of the small intestine. In certain embodiments, the polymer forms on the epithelium of the duodenum of the subject.

In some embodiments, the polymer binds with amine moieties exposed on the luminal surface of the epithelium of the subject. In some embodiments, the polymer crosslinks with amine moieties exposed on the luminal surface of the epithelium of the subject.

In some embodiments, the polymer is rapidly formed. In some embodiments, the polymer is formed in less than about 20 minutes. In some embodiments, the polymer is formed in less than about 15 minutes. In some embodiments, the polymer is formed in less than about 12 minutes. In some embodiments, the polymer is formed in less than about 10 minutes. In some embodiments, the polymer is formed in less than about 5 minutes. In some embodiments, the polymer is formed in less than about 3 minutes. In some embodiments, the polymer is formed in less than about 2 minutes. In some embodiments, the polymer is formed in less than about 1 minute. In some embodiments, the polymer forms almost instantly.

In some embodiments, the rate of polymerization increases by at least 10 times as compared to polymer formation without endogenous catalase. In some embodiments, the rate of polymerization increases by at least 50 times as compared to polymer formation without endogenous catalase. In some embodiments, the rate of polymerization increases by at least 100 times as compared to polymer formation without endogenous catalase. In some embodiments, the rate of polymerization increases by at least 150 times as compared to polymer formation without endogenous catalase. In some embodiments, the rate of polymerization increases by at least 200 times as compared to polymer formation without endogenous catalase.

In some embodiments, the polymer forms on the epithelium of the gastrointestinal tract of the subject. In some embodiments, the polymer forms on the epithelium of the small intestine of the subject.

In some embodiments, the polymer does not form on the epithelium of the gastrointestinal tract outside the small intestine of the subject.

In some embodiments, the polymer forms on the epithelium of one or more of the duodenum, the jejunum, the ileum, the colon, the esophagus, or the stomach of the subject. In some embodiments, the polymer forms on the epithelium of the duodenum of the subject. In some embodiments, the polymer forms on the epithelium of the jejunum of the subject. In some embodiments, the polymer forms on the epithelium of the ileum of the subject In some embodiments, the polymer forms on the epithelium of the colon of the subject.

In some embodiments, the polymer does not substantially form on the epithelium of one or more of the esophagus or stomach of the subject. In some embodiments, substantially no polymer forms on the stomach and the esophagus of the subject. In some embodiments, polymer does not form on the stomach and the esophagus of the subject.

In some embodiments, less is polymer formed on the ileum and the colon of the subject as compared to the duodenum and the jejunum of the subject.

In some embodiments, the polymer forms on the villi of the epithelium of the subject.

In some embodiments, the polymer forms a temporary barrier in vivo. In some embodiments, the polymer forms a transient barrier in vivo.

In some embodiments, the polymer lasts for about 30 minutes. In some embodiments, the polymer lasts for about 1 hour. In some embodiments, the polymer lasts for about 6 hours. In some embodiments, the polymer lasts for about 12 hours. In some embodiments, the polymer lasts for about 24 hours.

In some embodiments, about 20 to about 70% of the transient barrier remains after 12 hours. In some embodiments, about 30 to about 50% of the transient barrier remains after 12 hours. In some embodiments, about 20% of the transient barrier remains after 12 hours. In some embodiments, about 20 to about 70% of the transient barrier remains after 6 hours. In some embodiments, about 30 to about 50% of the transient barrier remains after 6 hours. In some embodiments, about 20% of the transient barrier remains after 6 hours. In some embodiments, about 20 to about 70% of the transient barrier remains after 3 hours. In some embodiments, about 30 to about 50% of the transient barrier remains after 3 hours. In some embodiments, about 20% of the transient barrier remains after 3 hours.

In some embodiments, the polymer is cleared from the subject after about 3 hours. In some embodiments, the polymer is cleared from the subject after about 6 hours. In some embodiments, the polymer is cleared from the subject after about 12 hours. In some embodiments, the polymer is cleared from the subject after about 24 hours. In some embodiments, the polymer is cleared from the subject after about 48 hours.

In some embodiments, the polymer barrier provides for selective molecular transport through the epithelium of the patient.

In some embodiments, the method is a method of modulating diffusion in the subject within the gut. In some embodiments, the method modulates diffusion of one or more of a salt, an ion, water, oxygen, carbon dioxide, carbonate anion, an acid, a base, a carbohydrate, a lipid, a protein, a nucleic acid, a nutrient, or an active pharmaceutical ingredient in the subject.

In some embodiments, polymer modulates absorption of one or more nutrients or active pharmaceutical ingredients within the small intestine.

In some embodiments, polymer substantially impedes absorption of one or more nutrients to the epithelium on which the polymer is formed, to the intestinal wall of the subject, or to the blood stream of the subject.

In some embodiments, the method is a method of delivering an agent to the subject. In some embodiments, the agent is an active pharmaceutical ingredient. In some embodiments, the agent is an enzyme. In some embodiments, the agent is a radioprotective agent. In some embodiments, the agent is delivered to the gut.

In some embodiments, the method enables sustained release of the agent in the subject. In some embodiments, the agent is an active pharmaceutical ingredient. In some embodiments, the agent is an enzyme. In some embodiments, the agent is a radioprotective agent. In some embodiments, the sustained released occurs in the GI tract.

In some embodiments, the method is a method of immobilizing an agent in a subject. In some embodiments, the agent is an active pharmaceutical ingredient. In some embodiments, the agent is an enzyme. In some embodiments, the agent is a radioprotective agent. In some embodiments, the agent is immobilized within the GI tract.

In some embodiments, the method is a method of localized delivery of an agent in a subject. In some embodiments, the agent is an active pharmaceutical ingredient. In some embodiments, the agent is an enzyme. In some embodiments, the agent is a radioprotective agent. In some embodiments, the localized delivery occurs in the GI tract.

In some embodiments, the method is a method of reducing the dosing frequency of the agent. In some embodiments, the agent is an active pharmaceutical ingredient. In some embodiments, the agent is an enzyme. In some embodiments, the agent is a radioprotective agent.

In some embodiments, the method is a method of increasing the half-life of the agent in the subject. In some embodiments, the agent is an active pharmaceutical ingredient. In some embodiments, the agent is an enzyme. In some embodiments, the agent is a radioprotective agent.

In some embodiments, the method is a method of increasing residence time of the agent in the subject. In some embodiments, the agent is an active pharmaceutical ingredient. In some embodiments, the agent is an enzyme. In some embodiments, the agent is a radioprotective agent. In some embodiments, the method is a method of increasing residence time of the agent in the GI tract.

In some embodiments, the method is a method of treating or preventing a disease in a subject. In some embodiments, the method is a method of treating a disease in a subject. In some embodiments, the method is a method of preventing a disease in a subject.

In some embodiments, the method is a method of aiding in tissue recovery and regeneration in the subject at the site of polymerization. In some embodiments, the method is a method of aiding in tissue recovery in the subject at the site of polymerization. In some embodiments, the method is a method of aiding in tissue regeneration in the subject at the site of polymerization.

In some embodiments, the method causes the intestinal lumen of the subject to remain expanded.

In some embodiments, the method is a method of preventing a bowel adhesion in the subject.

In some embodiments, the method is a method of preventing a bowel obstruction in the subject.

In some embodiments, the method is a method of treating bleeding in the subject. In some embodiments, bleeding is in the upper GI tract.

In some embodiments, the polymer and composition further comprises an enzyme. In some embodiments, the enzyme is a digestive enzyme. In some embodiments, the digestive enzyme is lactase, peptidase, sucrase, maltase, amylase, a lipase, or a protease. In some embodiments, the digestive enzyme is β-galactosidase.

In some embodiments, the method is a method of improving digestion efficiency by the subject.

In some embodiments, the method is a method of augmenting digestion of a sugar by the subject. In some embodiments, the method is a method of augmenting digestion of lactose by the subject.

In some embodiments, the method is a method of treating lactose intolerance in the subject.

In some embodiments, the enzyme improves digestion efficiency of a sugar of the subject by about 5 times. In some embodiments, the enzyme improves digestion efficiency of a sugar of the subject by about 10 times. In some embodiments, the enzyme improves digestion efficiency of a sugar of the subject by about 20 times. In some embodiments, the enzyme improves digestion efficiency of lactose of the subject by about 40 times. In some embodiments, the enzyme improves digestion efficiency of a sugar of the subject by about 50 times.

In some embodiments, β-galactosidase improves digestion efficiency of lactose of the subject by about 5 times. In some embodiments, β-galactosidase improves digestion efficiency of lactose of the subject by about 10 times. In some embodiments, β-galactosidase improves digestion efficiency of lactose of the subject by about 20 times. In some embodiments, β-galactosidase improves digestion efficiency of lactose of the subject by about 40 times. In some embodiments, β-galactosidase improves digestion efficiency of lactose of the subject by about 50 times.

In some embodiments, the polymer barrier does not inhibit the intrinsic digestive enzyme activity of the epithelium of the subject.

In some embodiments, the polymer and composition further comprises a nutrient blocker.

In some embodiments, the method is a method of preventing nutrient absorption in the subject.

In some embodiments, the method is a method of modulating or regulating sugar absorption by the subject. In some embodiments, the sugar is selected from glucose, lactose, fructose, maltose, dextrose, galactose, sucrose, and isomaltose. In some embodiments, the method is a method of modulating or regulating glucose absorption by the subject.

In some embodiments, the method prevents absorption for less than about 48 hours. In some embodiments, the method prevents absorption for less than about 24 hours. In some embodiments, the method prevents absorption for less than about 12 hours. In some embodiments, the method prevents absorption for less than about 6 hours. In some embodiments, the method prevents absorption for less than about 3 hours.

In some embodiments, the method is a method of treating obesity in the subject.

In some embodiments, the method is a method of treating hyperinsulinemia in the subject.

In some embodiments, the method is a method of treating diabetes mellitus in the subject. In some embodiments, the diabetes mellitus is type 2 diabetes mellitus.

In some embodiments, the composition further comprises a crosslinking agent.

In some embodiments, the crosslinking agent comprises a nanoparticle. In some embodiments, the crosslinking agent comprises polydopamine. In some embodiments, the crosslinking agent is a nutrient blocker. In some embodiments, the crosslinking agent improves the nutrient blocking ability of the polymer.

In some embodiments, glucose absorption is modulated by tuning the crosslinking density of polymer. In some embodiments, the method reduces glucose absorption by the subject by at least about 50%, at least about 60%, or at least about 70% for a period of 3 hours following administration of the composition. In some embodiments, the method reduces glucose absorption by the subject by at least about 70% for a period of 3 hours following administration of the composition. In some embodiments, the method reduces glucose absorption by the subject by at least about 50%, at least about 60%, or at least about 70% for a period of 2 hours following administration of the composition. In some embodiments, the method reduces glucose absorption by the subject by at least about 50%, at least about 60%, or at least about 70% for a period of 1 hours following administration of the composition.

In some embodiments, the method is a method of regulating or modulating nutrient uptake by the subject.

In some embodiments, the composition further comprises an active pharmaceutical ingredient. In some embodiments, the active pharmaceutical ingredient is an antiparasitic drug. In some embodiments, the active pharmaceutical ingredient is an anthelmintic drug. In some embodiments, the active pharmaceutical ingredient is praziquantel.

In some embodiments, the composition further comprises an active pharmaceutical ingredient. In some embodiments, the active pharmaceutical ingredient is agent treats an infectious disease. In some embodiments, the active pharmaceutical ingredient is an antiparasitic drug. In some embodiments, the active pharmaceutical ingredient is an anthelmintic drug. In some embodiments, the active pharmaceutical agent is an antiparasitic drug. In some embodiments, the active pharmaceutical ingredient is praziquantel. In some embodiments, the active pharmaceutical agent is an antiviral drug. In some embodiments, the active pharmaceutical agent treats influenza. In some embodiments, the active pharmaceutical agent treats type 2 diabetes. In some embodiments, the active pharmaceutical agent treats ocular diseases. In some embodiments, the active pharmaceutical agent treats Crohn's disease. In some embodiments, the active pharmaceutical agent treats osteoarthritis. In some embodiments, the active pharmaceutical agent treats Alzheimer's disease.

In some embodiments, the active pharmaceutical ingredient treats psychiatric disorders, Alzheimer's disease, infection diseases, or transplant rejection. In certain embodiments, the active pharmaceutical ingredient is a contraceptive, a statin, an anti-hypertensive, or an antibiotic.

In some embodiments, the active pharmaceutical ingredient. In some embodiments, the active pharmaceutical ingredient is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon a, interferon y), vaccines, hematopoietic growth factors, monoclonal serotherapy, immuno stimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the active pharmaceutical ingredient is selected from the group including, but not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the active pharmaceutical ingredient is an anti-proliferative agent. In certain embodiments, the active pharmaceutical ingredient is an anti-cancer agent. In certain embodiments, the active pharmaceutical ingredient is an anti-viral agent.

Exemplary active pharmaceutical ingredients include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins, etc. Active pharmaceutical ingredient include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the active pharmaceutical ingredient is an antibiotic. Exemplary antibiotics include, but are not limited to, penicillins (e.g., penicillin, amoxicillin), cephalosporins (e.g., cephalexin), macrolides (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, quinupristin/dalfoprisin (Syndercid™). In certain embodiments, the antibiotic is a ribosome-targeting antibiotic.

In some embodiments, the active pharmaceutical ingredient is retained or encapsulated in the polymer. In some embodiments, the active pharmaceutical ingredient is retained or encapsulated on the polymer.

In some embodiments, the method is a method of prolonging the residence time of an active pharmaceutical ingredient in the subject as compared to the administration of the active pharmaceutical ingredient in the absence of the polymer. In some embodiments, the method is a method of prolonging the residence time of an active pharmaceutical ingredient at the site of polymerization in the subject as compared to the administration of the active pharmaceutical ingredient in the absence of the polymer.

In some embodiments, the method is a method of providing for sustained release of an active pharmaceutical ingredient as compared to the administration of the active pharmaceutical ingredient in the absence of the polymer.

In some embodiments, the method is a method of reducing the dosing frequency of an active pharmaceutical ingredient as compared to the administration of the active pharmaceutical ingredient in the absence of the polymer. In some embodiments, the dosing frequency is once per day. In some embodiments, the dosing frequency is twice per day.

In some embodiments, the method is a method of increasing the half-life of the active pharmaceutical ingredient as compared to the administration of the active pharmaceutical ingredient in the absence of the polymer. In some embodiments, the method increases the half-life of the active pharmaceutical ingredient by at least about 2-fold as compared to the administration of the active pharmaceutical ingredient in the absence of the polymer. In some embodiments, the method increases the half-life of the active pharmaceutical ingredient by at least about 4-fold as compared to the administration of the active pharmaceutical ingredient in the absence of the polymer. In some embodiments, the method increases the half-life of the active pharmaceutical ingredient by at least about 6-fold as compared to the administration of the active pharmaceutical ingredient in the absence of the polymer. In some embodiments, the method increases the half-life of the active pharmaceutical ingredient by at least about 10-fold as compared to the administration of the active pharmaceutical ingredient in the absence of the polymer.

In some embodiments, the method is a method of increasing the AUC of the active pharmaceutical ingredient as compared to the administration of the active pharmaceutical ingredient in the absence of the polymer. In some embodiments, the method increases the AUC by at least about 2-fold as compared to the administration of the active pharmaceutical ingredient in the absence of the polymer. In some embodiments, the method increases the AUC by at least about 3-fold as compared to the administration of the active pharmaceutical ingredient in the absence of the polymer. In some embodiments, the method increases the AUC by at least about 4-fold as compared to the administration of the active pharmaceutical ingredient in the absence of the polymer.

In some embodiments, the method is a method of modulating the $C_{max}$ of the active pharmaceutical ingredient as compared to the administration of the active pharmaceutical ingredient in the absence of the polymer. In certain embodiments, the method of modulating is increasing. In certain embodiments, the method of modulating is decreasing.

In some embodiments, the method is a method of modulating the $T_{max}$ of the active pharmaceutical ingredient as compared to the administration of the active pharmaceutical ingredient in the absence of the polymer. In certain embodiments, the method of modulating is increasing. In certain embodiments, the method of modulating is decreasing.

In some embodiments, the method does not affect drug metabolism once the active pharmaceutical ingredient is absorbed by the small intestine.

In some embodiments, the method is a method of treating schistosomiasis in the subject.

In some embodiments, the composition further comprises a radioprotective agent. In certain embodiments, the radioprotective agent is an antioxidant, a thiol-containing compound, or a nitroxide. In certain embodiments, the radioprotective agent is thalidomide, cysteine, amifostine, palifermin, or 1-carnitine. In certain embodiments, the radioprotective agent is thalidomide.

In some embodiments, the nutraceutical agent is vitamin D or iron.

In some embodiments, the method provides for targeting the small intestine.

In some embodiments, the method is a method of decreasing uptake by the small intestine. In some embodiments, the method is a method of decreasing uptake of one or more nutrients and active pharmaceutical ingredients by the small intestine. In some embodiments, the method is a method of decreasing uptake of one or more nutrients by the small intestine. In some embodiments, the method is a method of decreasing uptake of one or more active pharmaceutical ingredients by the small intestine.

In some embodiments, the method is a method of increasing residence time in the small intestine. In some embodiments, the method is a method of increasing residence time of one or more of nutrients and active pharmaceutical ingredients in the small intestine. In some embodiments, the method is a method of increasing residence time of one or more nutrients in the small intestine. In some embodiments, the method is a method of increasing residence time of one or more active pharmaceutical ingredients in the small intestine.

In some embodiments, the method causes the intestinal lumen to remain expanded.

In some embodiments, the method is a method of treating or preventing a bowel adhesion in the subject. In some embodiments, the method is a method of preventing a bowel adhesion in the subject.

In some embodiments, the method is a method of treating or preventing bowel obstruction in the subject. In some embodiments, the method is a method of preventing bowel obstruction in the subject.

In some embodiments, the method is a method of treating bleeding in the subject. In some embodiments, the method is a method of treating bleeding in the small intestine of the subject. In some embodiments the bleeding is in the upper GI tract. In some embodiments, the bleeding is in the stomach. In some embodiments, the method of treating bleeding is a method of treating hemostasis.

In some embodiments, the polymer modulates absorption within the small intestine. In some embodiments, the polymer modulates absorption of one or more nutrients or active pharmaceutical ingredients, or combinations thereof, within the small intestine. In some embodiments, the polymer modulates absorption of one or more nutrients and active pharmaceutical ingredients within the small intestine. In some embodiments, the polymer modulates absorption of one or more nutrients within the small intestine. In some embodiments, the polymer modulates absorption of one or more active pharmaceutical ingredients within the small intestine.

In some embodiments, the polymer modulates digestion within the small intestine. In some embodiments, the polymer modulates digestion of one or more nutrients within the small intestine.

In certain embodiments, the polymer substantially impedes absorption by the small intestine. In some embodiments, the polymer substantially impedes absorption of one or more nutrients or active pharmaceutical ingredients, or combinations thereof, to the epithelium on which the polymer is formed. In some embodiments, the polymer substantially impedes absorption of one or more nutrients to the epithelium on which the polymer is formed. In some embodiments, the polymer substantially impedes absorption of one or more active pharmaceutical ingredients to the epithelium on which the polymer is formed.

In some embodiments, the polymer substantially impedes absorption of one or more nutrients or active pharmaceutical ingredients, or combinations thereof, to the intestinal wall of the subject. In some embodiments, the polymer substantially impedes absorption of one or more nutrients to the intestinal wall of the subject. In some embodiments, the polymer substantially impedes absorption of one or more active pharmaceutical ingredients to the intestinal wall of the subject.

In some embodiments, the polymer substantially impedes absorption of one or more nutrients or active pharmaceutical ingredients, or combinations thereof, to the blood stream of the subject. In some embodiments, the polymer substantially impedes absorption of one or more nutrients to the blood stream of the subject. In some embodiments, the polymer substantially impedes absorption of one or more active pharmaceutical ingredients to the blood stream of the subject.

In some embodiments, the method is a method of immobilizing an enzyme in a subject.

In some embodiments, the method is a method of delivering an active pharmaceutical ingredient to the subject.

In some embodiments, the method is a method of supplementing the digestion in a subject.

In some embodiments, the polymer induces blood gelation. In certain embodiments, the polymer induces coagulation. In some embodiments, the composition is in the form of a powder. In certain embodiments, the method comprises spraying the powder onto an affected area on or within the subject.

In some embodiments, the polymer is nontoxic. In some embodiments, the composition is nontoxic. In some embodiments, the composition and its components are nontoxic.

In some embodiments, the polymer is stable to physical and chemical forces. In some embodiments, the polymer is stable to one or more of intestinal fluid, intestinal acid, gastric acid, chyme, ethanol, and saline. In some embodiments, the polymer decomposes by less than about 25% upon exposure to one or more of intestinal fluid, intestinal acid, gastric acid, chyme, ethanol, or saline. In some embodiments, the polymer decomposes by less than about 20% upon exposure to one or more of intestinal fluid, intestinal acid, gastric acid, chyme, ethanol, or saline. In some embodiments, the polymer decomposes by less than about 10% upon exposure to one or more of intestinal fluid, intestinal acid, gastric acid, chyme, ethanol, or saline. In some embodiments, the polymer decomposes by less than about 5% upon exposure to one or more of intestinal fluid, intestinal acid, gastric acid, chyme, ethanol, or saline. In some embodiments, the physical forces are selected from one or more of peristalsis and segmentation.

In another aspect, the disclosure provides a method of treating a disease or disorder comprising administering an effective amount of a composition as described herein to a subject in need thereof.

Further provided by the disclosure is a method of preventing a disease or disorder comprising administering an effective amount of a composition as described herein to a subject in need thereof.

In some embodiments, the disease or disorder is a metabolic disorder, an ocular disease, a systemic disease, a digestive disorder, an infectious disease, cancer, bleeding, an ulcer, a bowel obstruction, mesenteric ischemia, obesity, a psychiatric disorder, Alzheimer's disease, or transplant rejection. In some embodiments, the disease or disorder is a metabolic disorder, a systemic disease, a digestive disorder, an infectious disease, cancer, bleeding, an ulcer, a bowel obstruction, mesenteric ischemia, obesity, a psychiatric disorder, Alzheimer's disease, or transplant rejection.

In some embodiments, the disease is cancer. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma);

Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g. ,bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In some embodiments, the metabolic disorder is hyperinsulinemia.

In some embodiments, the digestive disease is Crohn's disease, ulcerative colitis, malabsorption, inflammatory bowel disease, irritable bowel syndrome, lactose intolerance, or Celiac disease. n some embodiments, the disease is Crohn's disease.

In some embodiments, the disease is a psychiatric disorder.

In some embodiments, the disease is Alzheimer's disease.

In some embodiments, the disorder is transplant rejection.

In some embodiments, the systemic disease is an autoimmune disease. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

In some embodiments, the systemic disease is mastocytosis, chronic fatigue syndrome, systemic vasculitis, sarcoidosis, hypothyroidism, diabetes, fibromyalgia, adrenal insufficiency, celiac disease, ulcerative colitis, Crohn's disease, hypertension, metabolic syndrome, AIDS, Graves' disease, systemic lupus erythematosus, arthritis, atherosclerosis, sickle cell disease, myasthenia gravis, systemic sclerosis, inflammatory disease, or sinusitis.

In some embodiments, the disease is an inflammatory disease. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation. In some embodiments, the disease is an inflammatory joint disease. In some embodiments, the disease is arthritis. In certain embodiments, the disease is osteoarthritis. In some embodiments, the disease is rheumatoid arthritis.

In some embodiments, the disease is obesity, hyperinsulinemia, or diabetes. In some embodiments, the disease is obesity. In some embodiments, the disease is hyperinsulinemia. In some embodiments, the disease is diabetes. In some embodiments, the disease is type 2 diabetes.

In some embodiments, the disease is an infectious disease. In some embodiments, the disease is a bacterial, viral, fungal, or parasitic infection. In some embodiments, the disease is a parasitic disease. In some embodiments, the disease is giardiasis, ascariasis, or a tape worm infection. In some embodiments, the disease is schistosomiasis. In some embodiments, the disease is a viral infection. In some embodiments, the disease is influenza.

In some embodiments, the disease is lactose intolerance.

In some embodiments, the disorder is a bowel obstruction. In some embodiments, the disorder is a bowel adhesion. In certain embodiments, the methods and compositions described herein prevent re-adhesion and/or re-obstruction of the bowel.

In certain embodiments, the methods and compositions provided herein are contraceptives.

In certain embodiments, the disease is trauma.

In some embodiments, the disclosure provides for the use of a composition to form a polymer in vivo comprising administering to a subject a composition comprising a monomer and an oxygen source, wherein the monomer and the oxygen source contact a catalyst endogenous to the subject in vivo and the catalyst polymerizes the monomer in situ, wherein the monomer is dopamine, or salt thereof.

In another aspect, the disclosure provides for the use of a composition to form a polymer in vivo comprising administering to a subject a composition comprising a monomer and an oxygen source, wherein the monomer and the oxygen source contact a catalyst endogenous to the subject in vivo and the catalyst polymerizes the monomer in situ, and wherein the monomer is dopamine, or salt thereof, the oxygen source is hydrogen peroxide or urea hydrogen peroxide, and endogenous catalyst is selected from a catalase or a peroxidase.

In one aspect, the disclosure provides for the use of an effective amount of a composition as described herein to treat a disease or disorder in a subject in need thereof.

In a further aspect, the disclosure provides for the use of an effective amount of a composition as described herein to prevent a disease or disorder in a subject in need thereof.

Compositions

In certain aspects, further provided herein are compositions comprising dopamine, an oxygen source, and optionally a buffer.

In some embodiments, the composition comprises about 0.001 to about 1000 mg/mL dopamine, about 0.01 to about 100 mM of the oxygen source, and optionally, a buffer.

In some embodiments, the composition comprises about 0.001 to about 1000 mg/mL of dopamine. In some embodiments, the composition comprises about 0.001 to about 500 mg/mL of dopamine. In some embodiments, the composition comprises about 0.01 to about 100 mg/mL of dopamine. In some embodiments, the composition comprises about 1 to about 20 mg/mL of dopamine. In some embodiments, the composition comprises about 10 mg/mL of dopamine. In some embodiments, the composition comprises about 9.8 mg/mL of dopamine.

In some embodiments, the composition comprises about 0.01 to about 100 mM of the oxygen source. In some embodiments, the composition comprises about 0.1 to about 50 mM of the oxygen source. In some embodiments, the composition comprises about 1 to about 30 mM of the oxygen source. In some embodiments, the composition comprises about 20 mM of the oxygen source. In some embodiments, the composition comprises a concentration of oxygen source compatible with ingestion by the subject.

In some embodiments, the composition has a pH of about 7 to about 10. In some embodiments, the composition has a pH of about 7 to about 9. In some embodiments, the composition has a pH of about 8.5. In some embodiments, the composition has a pH of about 7.4.

In some embodiments, the composition comprises about 10 mg/mL of dopamine, about 20 mM hydrogen peroxide or urea hydrogen peroxide, and optionally, a buffer. In some embodiments, the composition comprises about 9.8 mg/mL of dopamine, about 20 mM hydrogen peroxide or urea hydrogen peroxide, and optionally, a buffer.

In some embodiments, the buffer comprises phosphate, acetate, citrate, N-[tris(hydroxymethyl)methyl]glycine), (tris(hydroxymethyl)aminomethane), or (2-(bis(2-hydroxyethyl)amino)acetic acid). In some embodiments, the buffer comprises tris(hydroxymethyl)aminomethane.

In some embodiments, the composition further comprises a digestive enzyme, a nutrient blocker, a radioprotective agent, a nutraceutical, an active pharmaceutical ingredient, a diagnostic agent, or a combination thereof.

In some embodiments, the composition is a liquid or solid dosage form. In some embodiments, the composition is in the form of a solution, a gel, a tablet, or a capsule.

Kits

Also encompassed by the disclosure are kits (e.g., pharmaceutical packs). The kits provided may comprise a composition described herein and a container (e.g., a vial, ampule, bottle, syringe, and/or dispenser package, or other suitable container).

The disclosure also provides kits. In one aspect, the disclosure provides a kit comprising: a composition as described herein, and instructions for administering the composition to a subject. In some embodiments, the composition comprises: dopamine; hydrogen peroxide or urea hydrogen peroxide; a buffer; and optionally, an enzyme, a nutrient blocker, a radioprotective agent, a nutraceutical, an active pharmaceutical ingredient, a diagnostic agent, or a combination thereof. In some embodiments, the buffer is tris(hydroxymethyl)aminomethane. In certain embodiments, the kit further comprises an endoscope, arthroscope, cystoscope, colposcope, colonoscope, bronchoscope, ureteroscope, anoscope, esophagoscope, gastroscope, laparoscope, laryngoscope, neuroendoscope, proctoscope, sigmoidoscope, or thoracoscope. In certain embodiments, the composition is in the form of a capsule.

In some embodiments, provided kits may optionally further include a second container comprising a pharmaceutical excipient for dilution or suspension of a composition described herein. In some embodiments, the composition described herein provided in the first container and the second container are combined to form one unit dosage form.

Thus, in one aspect, provided are kits including a first container comprising a composition described herein. In certain embodiments, the kits are useful for treating a disease in a subject in need thereof. In certain embodiments, the kits are useful for preventing a disease in a subject in need thereof. In certain embodiments, the kits are useful for reducing the risk of developing a disease in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease in a subject in need thereof. In certain embodiments, the kits and instructions provide for preventing a disease (in a subject in need thereof. In certain embodiments, the kits and instructions provide for reducing the risk of developing a disease in a subject in need thereof. A kit described herein may include one or more additional agents described herein as a separate composition.

Administration

The methods and uses described herein comprise administering to a subject an effective amount of a composition comprising a monomer and an oxygen source (i.e., to form a polymer in situ (e.g., in order to treat or prevent a disease).

In some embodiments, the composition is administered orally. In some embodiments, the composition is a liquid or a solid dosage form. In some embodiments, the composition is in the form of a solution, a gel, a tablet, or a capsule.

In certain embodiments, the effective amount is a therapeutically effective amount. In certain embodiments, the effective amount is an amount effective for treating an infectious disease in a subject in need thereof. In certain embodiments, the effective amount is an amount effective for preventing an infectious disease in a subject in need thereof. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating a hematological disease in a subject in need thereof. In certain embodiments, the effective amount is an amount effective for preventing a hematological disease in a subject in need thereof. In certain embodiments, the effective amount is an amount effective for treating a neurological disease in a subject in need thereof. In certain embodiments, the effective amount is an amount effective for preventing a neurological disease in a subject in need thereof. In certain embodiments, the effective amount is an amount effective for treating a in a painful condition subject in need thereof. In certain embodiments, the effective amount is an amount effective for preventing a painful condition in a subject in need thereof. In certain embodiments, the effective amount is an amount effective for treating a psychiatric disorder in a subject in need thereof. In certain embodiments, the effective amount is an amount effective for preventing a psychiatric disorder in a subject in need thereof. In certain embodiments, the effective amount is an amount effective for treating a metabolic disorder in a subject in need thereof. In certain embodiments, the effective amount is an amount effective for preventing a metabolic disorder in a subject in need thereof. In certain embodiments, the effective amount is an amount effective for reducing the risk of developing a disease (e.g., infectious disease, proliferative disease, hematological disease, neurological disease, painful condition, psychiatric disorder, or metabolic disorder) in a subject in need thereof. In certain embodiments, the effective amount is an amount effective for inhibiting the activity (e.g., aberrant activity, such as increased activity) of an organism in a subject or cell.

In certain embodiments, the subject is an animal. The animal may be of either sex and may be at any stage of development. In certain embodiments, the subject described herein is a human. In some embodiments, the subject is an adult human. In certain embodiments, the subject is a child. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

Compositions can be prepared, packaged, and/or sold in bulk, as a single unit dose, and/or as a plurality of single unit doses. A "unit dose" is a discrete amount of the composition comprising a predetermined amount of the agent or active ingredient. The amount of the agent or active ingredient is generally equal to the dosage of the agent or active ingredient which would be administered to a subject and/or a convenient fraction of such a dosage, such as one-half or one-third of such a dosage.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Compositions provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific agent or active ingredient employed; the specific composition employed; the age, body weight, general health, sex, and diet of the subject; the time of administration, route of administration, and rate of excretion of the specific agent or active ingredient employed; the duration of the treatment; drugs used in combination or coincidental with the specific agent or active ingredient employed; and like factors well known in the medical arts.

The compositions provided herein can be administered by any route, including enteral (e.g., oral), parenteral, intravenous, intramuscular, intra-arterial, intramedullary, intrathecal, subcutaneous, intraventricular, transdermal, interdermal, rectal, ophthalmic, intravaginal, intraperitoneal, topical, mucosal, nasal, bucal, sublingual; by intratracheal instillation, bronchial instillation, and/or inhalation; and/or as an oral spray, nasal spray, and/or aerosol. Also, contemplated routes are direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In some embodiments, the route of administration is topical (to skin, eye, ear, mouth, or affected site).

The exact amount of agent or agent or active ingredient required to achieve an effective amount will vary from subject to subject, depending, for example, on species, age, and general condition of a subject, severity of the side effects or disorder, identity of the particular agent or active ingredient, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent or active ingredient described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

A composition, as described herein, can be administered in combination with one or more additional pharmaceutical agents (e.g., therapeutically and/or prophylactically active agents). The compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of an organism in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects.

The composition can be administered concurrently with, prior to, or subsequent to one or more additional pharmaceutical agents, which may be useful as, e.g., combination therapies.

EXAMPLES

In order that the invention described herein may be more fully understood, the following examples are set forth. The examples described in this application are offered to illustrate the compounds, compositions, and methods provided herein and are not to be construed in any way as limiting their scope.

ABBREVIATIONS

PDA: polydopamine
CAT: catalase
GSEL: gastrointestinal synthetic epithelial lining
PBS: phosphate-buffered saline
TBS: Tris-buffered saline
TBST: Tris-buffered saline with TritonX 100
IgG: immunoglobulin G
mRNA: messenger ribonucleic acid
cDNA: complementary deoxyribonucleic acid
FTIR: Fourier transform infrared
Chemicals And Materials Dopamine hydrochloride (1225204), simulated gastric fluid (18818), urea $H_2O_2$ (289132), catalase (C3556 & C1345), Triton X-100 (T8787), 3-amino-1,2,4-triazole (A8056), RIPA buffer (R0278), protease inhibitor cocktail (P8340), phosphatase inhibitor cocktail 3 (P0044), Trizma base, o-nitrophenol-β-D-galactoside (N1127), β-Galactosidase (1356698), glucose (G8270), and lactose (17814) were purchased from Sigma-Aldrich. Formalin (10%, phosphate buffered) (SF100), Tissue-Plus O.C.T (23-730-571), BD GasPak EZ gas generating systems incubation containers (B260002) and SouthernBiotech Fluoromount-G slide mounting medium (OB100) were purchased from Fisher Scientific. Pierce BCA protein assay (23225), Pierce DAB substrate (34002), Pierce 16% formaldehyde (w/v) (28908), rabbit anti-goat immunoglobulin G (IgG) (H+L) secondary antibody-HRP (31402), goat anti-rabbit IgG (H+L) secondary antibody-HRP (65-6120), Vybrant MTT cell viability assay (V13154), Dynabeads M-280 (tosyl activated) (14203), SeeBlue Plus2 pre-stained protein standard (LC5925), SuperSignal West Femto Maximum Sensitivity substrate (34094), Pierce ECL western blotting substrate (32109), NuPAGE 4-12% Bis-Tris protein gels (NP0321BOX), NE-PER nuclear and cytoplasmic extraction kit (78835), Mem-PER plus membrane protein extraction kit (89842), antibiotic-antimycotic (100X) (15240062), SuperScript IV reverse transcriptase (18090050), PCR Master Mix, and all primers were purchased from ThermoFisher. Total RNA isolation kit was purchased from ZYMO RESEARCH. Precision Plus Protein dual color standard (#1610374) was purchased from Bio-Rad. Barium sulfate (13989) was purchased from Alfa Aesar. Simulated intestinal fluid was purchased from VWR. CYP3A4 activity assay kit (ab211076), calcium assay kit (ab102505), glutamate assay kit (ab138883), anti-catalase and anti-β-actin antibodies were purchased from Abcam. Catalase (CAT) assay kit (E-BC-K031) was purchased from Elabscience. Praziquantel was purchased from Ark Pharm. Sieves (150 and 300 μm mesh sizes) were purchased from McMaster-Carr. Glo-Tip spray catheter (G24892) was purchased from COOK Medical. All other chemicals and bio-chemicals (unless specified) were purchased from Sigma-Aldrich and used without further purification.

Methods

General. The in vivo tissue-accelerated polymerization coating performance was evaluated in the GI tract in a large animal (pig) model through multiple techniques including endoscopic examination, intestinal ligation, and X-ray imaging. Yorkshire pigs (45-55 kg) were chosen as the model, given their anatomic and genomic similarities to the human digestive system. The biocompatibility was characterized according to OECD guidelines. All animal experiments were approved by and performed in accordance with the Committee on Animal Care at Massachusetts Institute of Technology[19,28]. Group and sample size for each experiment are indicated in each figure description. Independent experiments for each sample were performed on different animals. All rats were randomly divided into different experimental groups, but there was no pre-established randomization plan for in vivo pig studies, because pigs were only available on demand.

Tissue-accelerated polymerization solution preparation. Dopamine hydrochloride powder (500 mg) was dissolved rapidly in Tris buffer (50 mM, 50 ml) at pH 8.5, followed by quick addition of $H_2O_2$ (1M, 1 ml). The mixed Tris-buffered tissue-accelerated polymerization solution was used fresh. The mixed solution was used fresh throughout all experiments unless otherwise noted and is referred to as the tissue-accelerated polymerization solution, or the like, and gastrointestinal synthetic epithelial lining (GSEL). Solid urea $H_2O_2$ (as a replacement of $H_2O_2$ solution) was used to prepare the tissue-accelerated polymerization capsules. Capsules were prepared with dopamine hydrochloride powder (500 mg), Tris powder (30-300 mg; e.g., 300 mg), and solid urea $H_2O_2$ powder (10-50 mg; e.g., 50 mg). The mixed powder was filled into (size 000) capsule. (see FIG. 37).

In vitro evaluation of catalase catalyzed polydopamine polymerization. Tissue-accelerated polymerization solution (200 μl) were prepared first and added into 96-well plates, followed by addition of catalase (1 mg/mL, 5 μl in 1× phosphate-buffered saline (PBS) buffer). All solutions were placed in containers (BD GasPak EZ) with a low partial pressure of oxygen. The reaction mixture was kept at 37° C. for 10-130 minutes. Extinction of solutions at 700 nm was measured using an Infinite M200 plate reader (Tecan). The results were compared with those obtained from solutions without addition of catalase and $H_2O_2$, and those obtained from reactions in conventional conditions (in the air). See FIGS. 1C to 1D and 6A to 6B.

Polydopamine characterization using FTIR and UV-Vis spectroscopy. Polydopamine standard was prepared by polymerization of the dopamine solution (10 mg/mL) in the conventional condition (in the air) for 24 hours (H. Lee, S. M. Dellatore, W. M. Miller, P. B. Messersmith, Mussel-inspired surface chemistry for multifunctional coatings., Science 318, 426-30 (2007)). For catalase catalyzed polydopamine, catalase (1 mg/mL) was placed in a dialysis device (5 ml), which was merged into the tissue-accelerated polymerization solution (100 ml) for 24 hours. After reaction, the polydopamine solutions were measured by FTIR (Nicolet) and UV-Vis spectroscopy (Varian Cary 100). See FIGS. 7A to 7D and 8A to 8C.

Ex vivo evaluation of the tissue-accelerated polymerization coating performance. Porcine tissues were acquired from the Blood Farm Slaughterhouse (West Groton, USA). Pigs were euthanized, and fresh tissue was resected and stored on ice. Human tissue specimens were acquired from 4 donors (National Disease Research Interchange, NDRI, USA) with different age, race and gender. Tissues (12 $cm^2$) were exposed to the tissue-accelerated polymerization solution (10 mL) and washed with PBS buffer (1×) 3 times to remove excess polydopamine. Samples (6 mm in diameter) were collected at 3-5 random sites of polydopamine coated tissue, and images of the samples were analyzed for quantification of the polydopamine coating. ImageJ was used to identify regions of interest that included polydopamine coated tissues and excluded 'blank' tissue-free areas. Identical analysis was performed on all samples in each group to obtain an overall average polydopamine signal intensity and assess signal variation. Tissues were exposed to the antibiotic-antimycotic solution (10×, Gibco) and washed with PBS buffer (1×) 3 times to remove bacteria in mucus. Villi was stripped off from the luminal surface of small intestinal tissue (opened lengthwise) placed on the ice-cold substrate. Cell fractionation was performed on villi by using cytoplasmic and membrane extraction kits (NE-PER, Mem-PER) based on the protocol from kits. The CYP3A4 activity was measured by the CYP3A4 activity assay (Abcam) based on the assay protocol. See FIGS. 1E to 1H, 5A to 5G, 9, 13, 15, 24, 25, 27, 28, 32, 34, and 35.

Tissue lysate preparation. Epithelial tissues of the porcine gastrointestinal tract were dissected on ice. The outer mucus layers were removed by aspiration, and then the rinsed tissues [(with 1× phosphate-buffered saline (PBS)] were frozen by liquid nitrogen. Tissues (10 mg) were incubated in the ice-cold lysis buffer (600 μl, RIPA buffer mixed with protease and phosphatase inhibitor cocktail, Sigma-Aldrich) and homogenized to form tissue lysates. The total protein concentrations of tissue lysates were measured by using the bicinchoninic acid (BCA) assay.

Catalytic capacity analysis of tissue lysates. A native gel-based catalytic activity assay was performed. Proteins in tissue lysates were resolved on a 7.5% non-denaturing polyacrylamide gel, and the gel was stained by the gastrointestinal synthetic epithelial linings (tissue-accelerated polymerization) solution (50 ml) for 10 minutes. After staining, the gel was washed 3 times with PBS buffer (1×) and imaged. FIGS. 2A and 10.

In vitro inhibition of catalase activity. 3-amino-1,2,4-triazole was used as the inhibitor. Tissue lysates (10 mg/ml, 100 μl) were incubated in the inhibitor solution (20 mM) for 6 hours at 4° C. See FIG. 2B.

Immunoprecipitation of catalase in tissue lysates. Catalase antibody was first conjugated on tosyl-activated magnetic beads (Dynabeads M-280) based on the Dynabeads protocol. The conjugated beads (60 mg) were further added into tissue lysate solutions (10 mg/ml, 100 µl), incubated for 2 hours to capture catalase in the solutions, and placed on the magnet for 2 minutes to remove beads. See FIG. 2C.

Evaluation of catalase expression in tissues. Fresh porcine tissues were collected for real-time PCR and western blotting. Total RNA was isolated and reverse transcribed into cDNA with standard protocol. The mRNA expression was measured using LightCycler 480 II system (Roche). Catalase mRNA expression level was normalized to housekeeping genes (β-actin, 18S, GUS, and GAPDH) and expressed as the percentage of negative control. For western blotting, tissue lysates were resolved on SDS-PAGE gel with standard protocol. Anti-catalase (1:500 diluted in Tris-buffered saline with TritonX 100 (TBST) buffer) and anti-β-actin (1:1000 diluted in TBST buffer) were used as primary antibodies. Secondary antibodies (1:2000 diluted in TBST buffer) were used for specific detection. Catalase signals were developed using SuperSignal™ West Femto Maximum Sensitivity substrate, and β-actin signals were developed using Pierce™ ECL western blotting substrate. The western blots were imaged on ChemiDoc™ XRS+ system (Bio-Rad) and analyzed with Image Lab 3.0. See FIGS. 2D to 2F, 10, 11, and 12.

Microscopic analysis of polydopamine coated tissues. Polydopamine coated small intestines were snap-frozen and embedded in optimal cutting temperature (O.C.T) Compound. The fixed tissues were cut into 40-µm-thick sections with a cryostat (Leica Biosystems). Specific peroxisome/catalase staining was performed as previously reported (M. Connock, W. Pover, Catalase particles in the epithelial cells of the guinea-pig small intestine, Histochem. J. 2, 371-380 (1970)). The uncoated tissue sections were stained with the 3,3'-diaminobenzidine (DAB) substrate or tissue-accelerated polymerization solution (1 mL) for 10 minutes. The slides were scanned by Aperio digital pathology slide scanner (Leica Biosystems) and analyzed with Aperio ImageScope (Leica Biosystems). See FIG. 2G to 2H, 5D, and 26.

In vivo evaluation of the tissue-accelerated polymerization coating performance. All animal experiments were approved by and performed in accordance with the Committee on Animal Care at Massachusetts Institute of Technology. A large animal model, 45-55 kg Yorkshire pigs (Tufts, Medford USA), was chosen to test the in vivo performance of the tissue-accelerated polymerization coating. Pigs were fed daily in the morning and in the evening with a diet consisting of pellets (laboratory mini-pig grower diet 5081), in addition to a midday snack consisting of various fruits and vegetables. The pellets consisted of ground oats, alfalfa meal, wheat middlings, soybean meal, dried beet pulp, salts, and other micronutrient supplements. Before orally administering the tissue-accelerated polymerization solution, the pigs were sedated with Telazol (tiletamine/zolazepam) (5 mg kg$^{-1}$ IM), xylazine (2 mg kg$^{-1}$ IM), and atropine (0.05 mg kg$^{-1}$ IM), intubated, and maintained with isoflurane (1 to 3% through inhalation). Also, the gastric fluid was removed from the stomach before administration of the Tris-buffered tissue-accelerated polymerization solution (pH 8.5). The tissue-accelerated polymerization solution (1 ml kg$^{-1}$) was orally administered to the intestine or stomach via a catheter under endoscopic visual guidance. Gastrointestinal endoscopy videography was used for real-time recording of polydopamine formation after delivery of the tissue-accelerated polymerization solution, and the endoscopic camera was placed both inside and outside the tissue-accelerated polymerization solution. To directly evaluate the polydopamine coating, a laparotomy was performed on pigs. A non-crushing clamp was applied at the small intestine before administration of the tissue-accelerated polymerization solution into the intestine. Tissue-accelerated polymerization solution filled the intestinal cavity up until the clamp site, unable to pass down to the lower small intestine. After 20 minutes of administration, pigs were euthanized and the tissue nearby the clamp was isolated, washed, and opened up. All animals were euthanized prior to tissue harvest. Macroscopic images of tissues were taken to evaluate the polydopamine coating performance. Blood pressure and heart rate of pigs were monitored during the procedures by using the Cardell Touch® multi-parameter monitor (Midmark). Additionally, no clinical or endoscopic evidence of gastrointestinal perforation, inflammation or obstruction was observed during the study. FIGS. 3, 4, 14, 16, 29, 30, 31, 33, and 37.

Polydopamine-probe preparation. Barium sulfate particles (20 g) were added into Tris buffer (50 mM, 1000 mL at pH 8.5), followed by quick addition of dopamine (10 g). The reaction mixture was kept at room temperature with stirring (600 rpm) for 3 hours. The as-synthesized polydopamine-probes were purified with centrifugation (4000 rpm×10 min). The purified polydopamine-probes were re-dispersed in 100 ml of water and sonicated. The purified polydopamine probes were lyophilized for 3 days and stored at −20° C. Before administration, polydopamine probes were resuspended in the tissue-accelerated polymerization solution and the polydopamine-probe-tissue-accelerated polymerization solution was used fresh. See FIGS. 3E and 15.

In vivo evaluation of intestinal retention of the polydopamine coating through X-ray imaging. Pigs were sedated, intubated, and maintained with isoflurane as described above. The gastric fluid was removed from the stomach before administration. Polydopamine-probes (20 mg$^{-1}$ mL$^{-1}$) were first suspended in the tissue-accelerated polymerization solution. Pigs were orally administered the polydopamine-probe suspended tissue-accelerated polymerization solution (3 ml kg$^{-1}$), and introduced into the small intestine. Conventional radio-opaque probe (unmodified barium sulfate particles) suspended aqueous solution at the same concentration was administered as the control. Radiographs were performed to monitor the intestinal retention of the probes and polydopamine coating. For short-term stability evaluation, X-ray images were taken before and after rinsing the coated area with 500 ml of water. For long-term retention assessment, a series of X-ray images were periodically taken at designated time points in the same location, during which pigs consistently consumed a liquid diet. Additionally, pigs were assessed clinically and radiographically for evidence of gastrointestinal perforation and obstruction (e.g., inappetence, abdominal distension, lack of stool, or vomiting). No clinical or radiographic evidence of gastrointestinal perforation and obstruction was observed during the study. See FIGS. 3E to 3I, and 16.

In vivo coating exogenous β-galactosidase on intestinal epithelium. Pigs were sedated, intubated, and maintained with isoflurane as described above. The gastric fluid was removed from the stomach before administration. A laparotomy was performed on pigs to open up the small intestine. A chamber was placed on top of the intestinal epithelium, followed by addition of the tissue-accelerated polymerization solution (3 ml) with suspended β-galactosidase (5 µg$^{-1}$ mL$^{-1}$). Three control chambers containing solutions with and without the agents (β-galactosidase and tissue-accelerated polymerization solution) were also placed in the same pig. After 20 minutes of coating, epithelium inside the chamber was washed 3 times with water, and the β-gal activity of the tissue was evaluated by using o-nitrophenol-β-D-galactoside (ONPG) as substrate. See FIGS. 4A to 4C.

Polydopamine nano-crosslinker preparation and characterization. Ammonium hydroxide (10 ml, 28-30% w/w) was diluted into 650 ml ethanol-water (4:9 ratio v/v) mixed solution. The mixed solution was stirred under at 30° C. for 1 hour, followed by addition of 50 ml dopamine solution (50 mg$^{-1}$ mL$^{-1}$ in water). The reaction mixture was kept at 30° C. for 24 hours. The as-synthesized polydopamine nano-crosslinkers were purified with centrifugation (6000 rpm×15 min). The purified polydopamine nano-crosslinkers were re-dispersed in 500 ml of water and sonicated. The dry size and hydrodynamic size were measured with a transmission electron microscope (TEM, JEOL 2100F, JEOL Ltd) and a Zetasizer Nano ZS90 instrument (Malvern Panalytical), respectively. See FIGS. 4D to 4E and 17A to 17B.

Ex vivo evaluation of blocking efficiency of the tissue-accelerated polymerization. Tissues were exposed to the tissue-accelerated polymerization and washed with PBS buffer (1×) 3 times to remove excess polydopamine. Polydopamine nano-crosslinkers with different concentrations (25 mg$^{-1}$ mL$^{-1}$, 12.5 mg$^{-1}$ mL$^{-1}$, and 0 mg$^{-1}$ mL$^{-1}$) were suspended in the tissue-accelerated polymerization. The coated tissues were placed in the Franz Cell, 100 mM nutrients (CaCl$_2$, glutamic acid and glucose) were added separately into the chamber (occluded with Parafilm), and the samples were taken from the receptor compartment (with stir bars) for measurements after 3 hours. See FIGS. 32A to 32D.

In vivo evolution of the impermeable polydopamine coating for preventing glucose uptake. Pigs (fasted overnight) were sedated, intubated, and maintained with isoflurane as described above. The gastric fluid was removed from the stomach before administration. Polydopamine nano-crosslinkers (25 mg$^{-1}$ mL$^{-1}$) were first suspended in the tissue-accelerated polymerization solution. Pigs were orally administered the nano-crosslinker suspended tissue-accelerated polymerization composition (10 ml kg$^{-1}$), and introduced into the small intestine. The solution was directly administered to the small intestine through a catheter under endoscopic visual guidance. For controls, 500 ml of water solution was administered in the same way. Standard oral glucose tolerance test (OGTT) tests were performed on pigs after 20 minutes of solution administration (Y. Lee, T. E. Deelman, K. Chen, D. S. Y. Lin, A. Tavakkoli, J. M. Karp, Therapeutic luminal coating of the intestine, Nat. Mater. 17, 834-842 (2018); E. Manell, P. Hedenqvist, A. Svensson, M. Jensen-Waern, E. Xu, Ed. Establishment of a refined oral glucose tolerance test in pigs, and assessment of insulin, glucagon and glucagon-like peptide-1 responses, PLoS One 11, e0148896 (2016)). Pigs were orally administered the aqueous glucose solution (3 ml kg$^{-1}$, 500 mg$^{-1}$ mL$^{-1}$), and introduced into the small intestine. Blood samples were collected from a central venous line at designated time points, and immediately tested for glucose levels using an OneTouch Ultra® glucose monitor (LifeScan Inc). Each data point (blood glucose change) was plotted with time, and area under the curve was calculated for quantitative evaluation. See FIGS. 4A, 4D to 4E, and 33.

Praziquantel-tissue-accelerated polymerization preparation. Praziquantel particles were encapsulated in polydopamine, allowing the reactive groups (e.g. catechol and amine groups) on the polydopamine surface to enable chemical crosslinking and incorporation of praziquantel particles into the polydopamine coating layer. Additionally, the hydrophilic polydopamine layer on the particle surface dramatically improves the stability and dispersion property of hydrophobic drug particles. Praziquantel particles (powder) (8 g) were sieved (150-300 μm mesh size) and added into Tris buffer (50 mM, 400 ml at pH 8.5), followed by quick addition of dopamine (4 g) (J. Park, T. F. Brust, H. J. Lee, S. C. Lee, V. J. Watts, Y. Yeo, Polydopamine-based simple and versatile surface modification of polymeric nano drug carriers, ACS Nano 8, 3347-3356 (2014)). The reaction mixture was kept at room temperature and stirred (600 rpm) for 3 hours. The as-synthesized praziquantel particles were purified with centrifugation (4000 rpm×10 min). The purified praziquantel particles were lyophilized for 3 days and stored at −20° C. Before administration, praziquantel particles were resuspended in the tissue-accelerated polymerization solution and the praziquantel-tissue-accelerated polymerization was used fresh. See FIGS. 4A, 4F and 4G.

Praziquantel concentration assessment. High-Performance Liquid Chromatography An Agilent 1260 Infinity II HPLC system (Agilent Technologies, Inc.) equipped with Model 1260 quaternary pump, Model 1260 Hip ALS autosampler, Model 1290 thermostat, Model 1260 TCC control module, and Model 1260 diode array detector was utilized. Data processing and analysis was performed using OpenLab CDS® software (Agilent Technologies, Inc.). For praziquantel, chromatographic isocratic separation was carried out on an Agilent Zorbax Eclipse XDB C$^{-1}$8 4.6×150 mm analytical column with 5 μm particles, maintained at 40° C. The optimized mobile phase consisted of MilliQ grade water and acetonitrile at a flow rate of 1 ml min$^{-1}$ over a 5 minutes run time. Separation was achieved using a gradient elution profile starting at 50% water and 50% acetonitrile at minute 0 which ended at 30% water and 70% acetonitrile at 3 minutes. The injection volume was 5 μl, and the selected ultraviolet (UV) detection wavelength was 217 nm. See FIGS. 4F and 4G.

In vivo evolution of pharmacokinetics of the praziquantel-tissue-accelerated polymerization. Pigs were sedated, intubated, and maintained with isoflurane as described above. The gastric fluid was removed from the stomach before administration. Praziquantel-tissue-accelerated polymerization (20 mg$^{-1}$ mL$^{-1}$, 1 ml kg$^{-1}$) was delivered into the small intestine. Praziquantel without the tissue-accelerated polymerization was used as the control. Blood samples were collected from a marginal ear vein at designated time points. Serum samples were separated from blood by centrifugation (1800 G×10 min at 4° C.) and were stored at −80° C. for further analysis. See FIGS. 4F and 4G.

Serum praziquantel concentration assessment. Praziquantel concentrations in serum from in vivo experiments were analyzed using Ultra-Performance Liquid Chromatography-Tandem Mass Spectrometry (UPLC-MS/MS). Analysis was performed on a Waters ACQUITY UPLC-I-Class System aligned with a Waters Xevo TQ-S mass spectrometer (Waters Corporation, Milford Mass.). Liquid chromatographic separation was performed on an Acquity UPLC BEH C18 (50 mm×2.1 mm, 1.7-μm particle size) column at 50° C. The mobile phase consisted of aqueous 0.1% formic acid, 10 mM ammonium formate solution (Mobile Phase A) and acetonitrile: 10 mM ammonium formate, 0.1% formic acid solution (95:5 v/v) (Mobile Phase B). The mobile phase had a continuous flow rate of 0.6 ml/min using a time and solvent gradient composition. For the analysis of praziquantel, the initial composition, 80% Mobile Phase A, was held for 0.50 minutes, following which the composition was changed linearly to 0% Mobile Phase A over the next 2.00 minutes.

The composition of 0% Mobile Phase A and 100% Mobile Phase B was held constant until 3.50 minutes. The composition returned to 80% Mobile Phase A at 3.51 minutes and was held at this composition until completion of the run, ending at 5.00 minutes, where it remained for column equilibration. The total run time was 5.00 minutes. The mass to charge transitions (m/z) used to quantitate praziquantel were 313.22>203.09 and 313.22>83.01 for quantitation and confirmation respectively. As an internal standard, mebendazole, 296.06>264.03 and 296.06>76.99 m/z transitions were used for quantitation and confirmation respectively. Sample introduction and ionization was by electrospray ionization (ESI) in the positive ionization mode. Waters MassLynx 4.1 software was used for data acquisition and analysis. Stock solutions of praziquantel were prepared in methanol at a concentration of 500 µg/ml. A twelve-point calibration curve was prepared in analyte-free, blank serum ranging from 1.25-5000 ng/ml. 100 µl of each serum sample was spiked with 200 µl of 250 ng/ml mebendazole in acetonitrile to elicit protein precipitation. Samples were vortexed, sonicated for 10 minutes, and centrifuged for 10 minutes at 13,000 rpm. 200 µl of supernatant was pipetted into a 96-well plate containing 200 µl of water. Finally, 1.00 µl was injected onto the UPLC-ESI-MS system for analysis. See FIGS. 4F and 4G.

Serum and tissue dopamine concentration assessment. Dopamine concentrations in serum and tissue from in vivo experiments were analyzed using Ultra-Performance Liquid Chromatography-Tandem Mass Spectrometry (UPLC-MS/MS). Analysis was performed on a Waters ACQUITY UPLC-I-Class System aligned with a Waters Xevo TQ-S mass spectrometer (Waters Corporation, Milford Mass.). Liquid chromatographic separation was performed on an Acquity UPLC BEH C18 (50 mm×2.1 mm, 1.7-µm particle size) column at 50° C. The mobile phase consisted of aqueous 0.1% formic acid, 10 mM ammonium formate solution (Mobile Phase A) and acetonitrile: 10 mM ammonium formate, 0.1% formic acid solution (95:5 v/v) (Mobile Phase B). The mobile phase had a continuous flow rate of 0.45 ml/min using a time and solvent gradient composition. Sample introduction and ionization was by electrospray ionization (ESI) in the positive ionization mode. Waters MassLynx 4.1 software was used for data acquisition and analysis. Stock solutions were prepared in methanol at a concentration of 500 µg/ml. A twelve-point calibration curve was prepared in analyte-free, blank porcine serum ranging from 1.25-10000 ng/ml. 100 µl of each serum sample was spiked with 100 µl of 500 ng/ml methyldopamine (internal standard) in acetonitrile to elicit protein precipitation. 200 ul of 5 mg/ml fluorescamine in acetonitrile was then added to each sample as a derivatization agent for both dopamine and methyldopamine to aid in detection. Samples were vortexed, sonicated for 10 minutes, and centrifuged for 10 minutes at 13,000 rpm. 300 µl of supernatant was incubated at 37° C. for 60 minutes. 200 ul of incubated solution was then added to 200 ul of water in a 96-well plate. Finally, 10 µl was injected onto the UPLC-ESI-MS system for analysis. See FIG. 31.

Tissue samples were divided into pieces of about 300 mg. 3% bovine serum albumin in PBS buffer was added at a 2:1 volume to mass ratio. Samples were homogenized at 4° C. 100 µl of each homogenate was spiked with 100 µl of 500 ng/ml methyldopamine in acetonitrile and 200 ul of 5 mg/ml fluorescamine in acetonitrile for derivatization. 1.00 ml of ethyl acetate was added to homogenized samples as well for extraction. Samples were vortexed, sonicated for 10 minutes, and centrifuged for 10 minutes at 13,000 rpm. Following centrifugation, 300 µl of the supernatant was incubated at 37° C. for 60 minutes. Samples were allowed to evaporate overnight. The evaporated samples were reconstituted with 300 µl acetonitrile and centrifuged for 5 minutes at 6,000 rpm. 200 µl of the supernatant was pipetted into a 96-well plate containing 200 µl of water. Finally, 10 µl was injected onto the UPLC-ESI-MS system for the analysis. See FIG. 31.

For the analysis of dopamine fluorescamine, the initial composition, 95% Mobile Phase A, was held for 0.75 minutes. Following which, the composition was changed linearly to 5% Mobile Phase A and 95% Mobile Phase B until 1.00 minute. The composition was held constant at 95% Mobile Phase B until 3.00 minutes. At 3.25 minutes the composition returned to 95% Mobile Phase A, where it remained for column equilibration for the duration of the run, ending at 4.00 minutes. The mass to charge transitions (m/z) used to quantitate dopamine were 414.223>137.125 and 414.223>119.115 for quantitation and confirmation respectively. For internal standard, methyldopamine fluorescamine, 472.223>139.139 and 472.223>278.094 m/z transitions were used for quantitation and confirmation respectively. See FIGS. 31A and 31B.

Cytotoxicity assay. Vybrant MTT cell proliferation assay was used to test the cytotoxicity of polydopamine (PDA) in living cells. As-prepared polydopamine was added into the cell culture medium with various concentrations (0, 10, 50, 250, 500, 1000, 1500 and 2000 µg/ml). Cytotoxicity was tested on multiple cell lines: HeLa (ATCC), COLO320DM (ATCC), Caco-2 (ATCC), Hep3B (ATCC), and HS 895.T (ATCC), by seeding them each in a 96-well plate at a density of 10,000 cells, and keeping them in culture for 24 hours before replacing the medium with 100 µl polydopamine solution. The cells were incubated at 37° C. for various amounts of time (6, 12, 24 hours) in cell culture incubator. The cells were washed 3 times with PBS buffer, followed by addition of the MTT solution (10 µl) and cell culture medium (100 µl) to each well and incubation for 4 hours at 37° C. After 4 hours, 100 µl SDS-HCl solution was added to each well for another 4 hours incubation (at 37° C.). Absorbance at 570 nm was recorded on a 96-well plate reader (Tecan Infinite M200). See FIG. 19.

Oral toxicity test. Three groups (4 animals in each group) of rats (Sprague Dawley, 150-200 g, Charles River Labs) were exposed to water (5 ml kg$^{-1}$) , as-prepared polydopamine (15 mg mL$^{-1}$, 5 ml kg$^{-1}$), and tissue-accelerated polymerization solution (5 ml kg$^{-1}$) separately over a period of 4 weeks by following guidelines issued by OECD with minor modifications (OECD, Test no. 407: repeated dose 28-day oral toxicity study in rodents OECD Guidel. Test. Chem. Sect. 4, OECD Publ. Paris , 1-10 (2008)). The solution was directly administered to rats through gavage needles, but not endoscopic catheters. Body weights were measured every day for 28 days. Blood samples were collected at day 27 for hematological and blood biochemistry measurements, and food was withheld for 24 hours. At day 28, all 12 rats were euthanized and a necropsy was performed. Samples of heart, lung, liver, kidney, spleen, stomach, small intestine, and large intestine were collected for histological analyses. See FIGS. 20, 21, 22, and 23.

Histological analyses of tissues. Tissues were first fixed in PBS buffer (1×) with 4% paraformaldehyde for 6 hours and then placed into PBS buffer with 30% sucrose overnight at 4° C. The fixed tissues were embedded in paraffin and cut into 5-µm-thick sections with a cryostat (Leica Biosystems). The sections were stained with hematoxylin and eosin for histopathological analysis. See FIGS. 5D and 23.

Polydopamine coating of impermeable polycarbonate sheets. Polycarbonate sheets were exposed to the tissue-accelerated polymerization solution (without $H_2O_2$) for 36 hours and washed with water to remove excess polydopamine. See FIGS. 36A to 36C.

Statistical analysis. All data were reported as means±SD for n≥3 measurements for each group. Two-sample t tests, one-way ANOVA, and post hoc Bonferroni multiple comparisons test were used to determine the significance.

Overview of Selected Examples

The compositions, methods, and kits described in the present disclosure have been evaluated for therapeutic value in a number of clinical scenarios. Tissue-accelerated polymerization was applied to address lactose intolerance by coating digestive enzymes on the small intestinal epithelium. The results show that β-galactosidase coated on the tissue improves digestion efficiency of lactose by approximately 20 times, indicating the therapeutic utility of the present disclosure in digestive disorders and diseases. Furthermore, the power of the tissue-accelerated polymerization technology was assessed in the regulation of intestinal glucose absorption, an urgent need for patients with type 2 diabetes mellitus. An impermeable coating layer, serving as a glucose-blocking barrier, has been developed to prevent postprandial glucose intake (~70% reduction of glucose responses). The application of tissue-accelerated polymerization was expanded to improve administration efficiency for medications with inconvenient regiments, demonstrating its capability for sustained release of therapeutics. The disclosed method for administration of praziquantel (an anthelmintic drug) achieves long-lasting (over 24 hours) drug levels in systemic circulation (10-fold increase of half-time value), having the potential to revolutionize medication options for patients with schistosomiasis and other regiment-dependent diseases. Together with the outstanding performance of the tissue-accelerated polymerization technology in human tissue specimens, these clinical applications are suitable for in vivo human testing. The tissue-accelerated polymerization technology is applicable in broad technology adoption and application in disease treatment and health management.

EXAMPLE 1

Endogenous Enzyme Catalyzed Polydopamine Growth on Epithelium

To demonstrate the acceleration of polydopamine polymerization by catalase in a hypoxic environment, mimicking the low partial pressure of oxygen in the gastrointestinal tract, polydopamine polymerization rates were quantitatively evaluated in different reaction conditions, in which dopamine was maintained at the same concentration (FIGS. 1B-D and FIGS. 6A-6B). In an extremely oxygen deficient environment, the conventionally slow polydopamine polymerization was inhibited by 65% (FIGS. 6A-6B). The addition of a trace amount of hydrogen peroxide ($H_2O_2$), serving as a strong reducing agent, prevented dopamine oxidation and almost quenched the reaction. As shown in FIG. 1C, the slow color change of the dopamine solution from clear to light gray over two hours indicates minimal polydopamine polymerization, and the clear dopamine-$H_2O_2$ solution indicates negligible polydopamine polymerization. In contrast, the color of the dopamine solution with the addition of both catalase and $H_2O_2$ rapidly turned to a dark-brown color, demonstrating accelerated polydopamine polymerization. In this study, the polymerized products catalyzed by catalase from both commercially purified enzymes and crude tissue lysates were confirmed to be polydopamine by using both Fourier transform infrared (FTIR) and ultraviolet-visible (UV-Vis) spectroscopy (FIGS. 7A-7D and 8A-8C). To further quantify the effect of catalase on polydopamine polymerization rate, a comparison of reaction kinetics was plotted by measuring the optical extinction of solutions at 700 nm, where polydopamine has a light-absorbing feature (FIG. 1D). The signal of the catalase-polydopamine combination rapidly grew and plateaued within 10 minutes of reaction. However, intensities of light extinction in other conditions were relatively low, even after 2 hours, of which the same level of intensity was reached within 20 seconds under catalase catalysis conditions, showing an increase of polymerization rate by approximately 400 times.

Next, whether endogenous catalase can expedite polydopamine polymerization and coating on the small intestine to achieve tissue-accelerated polymerization on the exterior epithelium was assessed. The porcine gastrointestinal tract was chosen as the first model tissue, due to its anatomical and physiological similarities with the human digestive system. Ex vivo tissues were incubated with the tissue-accelerated polymerization solution, containing dopamine as well as hydrogen peroxide, of which concentrations were within safe oral-consumption levels. As shown in FIG. 1E and FIG. 9, when the mucosal side of small intestine was exposed to the tissue-accelerated polymerization solution, a dark-brown polydopamine coating was clearly observed on the epithelial surface, demonstrating that polydopamine was formed in situ and deposited on anchor points of the tissue due to the high reactivity between polydopamine and primary amines in nearby biomolecules[14]. In contrast, almost no polydopamine was found on the serosal side of the tissue after the same incubation, indicating that polydopamine polymerization is an enzyme-dependent reaction (FIG. 1E). These polydopamine coating processes were visualized due to the chromogenic property of polydopamine. To further quantify the polydopamine growth speed, the amount of polydopamine coated on small intestine was analyzed in a series of reaction times. The coating kinetics showed rapid polydopamine signal development, reaching completion within 12 minutes (FIG. 1F), indicating a fast polydopamine coating process. In addition to efficiency, the specificity of tissue-accelerated polymerization was also evaluated by comparing the tissue-accelerated polymerization coating in different parts of the gastrointestinal tract, including the esophagus, stomach, duodenum, jejunum, ileum, and colon. As shown in FIG. 1G, images of the tissue (6 mm in diameter) reveal obvious polydopamine coating on the duodenum and jejunum, relatively less polydopamine coating on ileum and colon, and negligible polydopamine coating on the stomach and esophagus. This coating pattern was additionally demonstrated through quantitative polydopamine signal analysis in FIG. 1H. This extraordinary efficiency and specificity of tissue-accelerated polymerization paves the road for downstream in vivo applications.

EXAMPLE 2

Mechanisms of Tissue-Accelerated Polymerization at Molecular, Cellular and Tissue Levels Prior to exploring applications of the tissue-accelerated polymerization technology, its biological mechanisms was systematically investigated in detail. First, it was tested whether endogenous catalase is the component that determines the catalytic polydopamine polymerization on epithelium. Epithelial tissues of the porcine gastrointestinal tract were dissected and washed, the outer mucus layers were removed by aspiration, and then the rinsed tissues were homogenized to prepare tissue lysates, which were further diluted relative to the total protein concentration. These tissue lysates were added individually into the tissue-accelerated polymerization solution, and the light extinction of each solution was measured following the reaction. As shown in FIG. 2A, signals of the polydopamine solutions with lysates of small intestinal epithelium were higher relative to others, consistent with the tissue-coating results FIG. 1G). In addition, similar trends were observed in a catalytic capacity analysis of these lysates through native gel electrophoresis and polydopamine staining (FIG. 10). Only one sharp band was visualized in each lane, supporting catalase's predicted role as the sole enzyme responsible for polydopamine polymerization. To further confirm the exclusive role of catalase, small intestinal lysates were treated by either the catalase-specific inhibitor to reduce catalase activity, or the catalase antibody coated magnetic bead to remove immunoprecipitated catalase. As shown in FIG. 2B, the catalytic capacity of lysates decreased by around 80% after adding the inhibitor, and decreased by around 90% upon removal of catalase from samples (FIG. 2C), demonstrating that the tissue-accelerated polymerization process is exclusively catalase-dependent. Additionally, it was also confirmed that catalase present due to bacteria in the small intestinal mucus did not affect the tissue-accelerated polymerization coating process (FIGS. 24A-24B and 25) showing that most of the $H_2O_2$ was not degraded or consumed in the intestinal lumen, and the amount of $H_2O_2$ was sufficient to activate oxygen release and polydopamine polymerization. In addition, it was observed that the catalytic polydopamine polymerization primarily occurs in the small intestine, which is due to higher expression of catalase in the small intestine as compared to other segments of the GI tract.

It has been previously shown that mRNA and protein level expression of human catalase is higher in the small intestine than other organs of the digestive tract, such as the esophagus, stomach and large intestine[15], playing a role in the coating specificity of tissue-accelerated polymerization technology. To further confirm this distinguishable catalase expression feature in gastrointestinal epithelium, quantitative evaluation of catalase expression along the porcine gastrointestinal tract was performed by both gene and protein analysis. As shown in FIG. 2D, high levels of catalase activity were detected in the duodenum and jejunum, whereas catalase activity levels in the esophagus, stomach, ileum and colon were relatively low, indicating catalase's strong activity in the small intestine relative to the rest of gastrointestinal tissues. Additionally, the catalase mRNA levels in tissues were measured by using quantitative real-time polymerase chain reaction (PCR). The catalase mRNA expression level in the small intestine was approximately 10 fold higher than that of other epithelial tissues (FIG. 2E and FIGS. 11A-11B), yet there was no such difference of the control gene (housekeeping genes) mRNA levels between the small intestine and other organs (FIGS. 12A-12E). As predicted, the small intestine catalase protein expression levels had similar distribution profiles compared to mRNA expression levels in the gastrointestinal tract (western blot analysis, FIG. 2F).

Then, efforts were undertaken to characterize the interface between the polydopamine layer and epithelium microscopically. The chromogenic polydopamine was visualized not only by the naked eye but also by microscopy[16]. Interestingly, it was found that during the tissue-accelerated polymerization process, polydopamine first deposits on intestinal villus tips, and then coats the whole villi, as well as the surrounding area (FIG. 13). Microscopic analysis showed a thin polydopamine layer tightly coated on the exterior villi (FIG. 2G), but nothing on the control tissue (without tissue-accelerated polymerization treatment). Polydopamine was completely confined on the outer layer of epithelium, the luminal surface, not inside epithelial cells, demonstrating that polydopamine polymerization happens only at the epithelial surface, with dopamine remaining outside of the cells throughout the whole reaction (FIGS. 26A-26C, 27, and 28). Specific peroxisome/catalase staining studies showed that catalase is located inside peroxisomes, which have a high-density distribution in villi, but not in submucosa and other inner layers (FIG. 2H, left panels). Similar studies have confirmed that catalase 'particles' are present in peroxisomes of intestinal epithelial cells[17]. To further confirm that peroxisomal catalase can catalyze polydopamine formation, dopamine was used for staining in place of the typical peroxisome/catalase substrate. As shown in FIG. 2H (right panel), dark-brown polydopamine spots were observed inside epithelial cells and the staining pattern was consistent with the conventional peroxisome/catalase staining, confirming the catalytic capacity of peroxisomal catalase towards polydopamine polymerization in sectioned tissue segments. The peroxisomal polydopamine pattern was not observed in tissue-accelerated polymerization-coated samples (FIG. 2G, left panels) which received tissue-accelerated polymerization luminally and were subsequently sectioned for microscopy without peroxisome/catalase staining.

EXAMPLE 3

Evaluation of Tissue-Accelerated Polymerization-Based Tissue-Coating Performance In Vivo Having illustrated the biological mechanisms of tissue-accelerated polymerization, the in vivo performance of this tissue-coating technology in Yorkshire pigs was tested. It is worth mentioning again that the advantages of using pigs as the large animal model include their extensive homology with the human genome, anatomical similarity to the human gastrointestinal tract, and physiological likeness to the human digestive system[18,19]. Under moderate sedation, pigs were orally administered the tissue-accelerated polymerization solution, introduced into the small intestine through the esophagus under endoscopic monitoring (FIG. 3A). Gastrointestinal endoscopy was used for real-time recording of polydopamine formation after delivery of the tissue-accelerated polymerization solution, and the endoscopic camera was placed both inside and outside the tissue-accelerated polymerization solution (FIG. 3B and 3C). The results of the in vivo observations were in agreement with those of the ex vivo tissue-coating studies. As shown in FIG. 3C, a dark-brown polydopamine layer was observed on the wall of small intestine after 20 minutes of administration, whereas no such polydopamine coating was visualized in the stomach after the same gavage (FIGS. 14A-14C). The tissue-accelerated polymerization solution remained overall stable in the stomach for 30-60 minutes (FIG. 29), confirming the durability of the solution. To be noted, all animals were fasted overnight, and the gastric fluid was removed from the stomach before administration of the Tris-buffered tissue-accelerated polymerization solution (pH 8.5), thus minimizing the possible effect of pH on the stability of the tissue-accelerated polymerization solution and polydopamine polymerization. Additionally, no detectable increase of polydopamine and dopamine signal in the submucosa and blood after the tissue-accelerated polymerization coating was observed, where microscopy (FIGS. 26A-26C), UV-Vis spectroscopy (FIG. 30) and liquid chromatography-tandem mass spectroscopy (FIGS. 31A-31B) were applied for the signal measurements. Furthermore, no significant increase of blood pressure or heart rate was detected in any animals throughout the procedures, demonstrating the lack of dopamine absorption and the supporting the early safety of the tissue-accelerated polymerization technology[40]. Consistent with the schematic illustration of the tissue-accelerated polymerization technology depicted in FIG. 1A, the endoscopic video revealed that the polydopamine coating process contained three main steps. When the clear dopamine-$H_2O_2$ solution was first introduced to the small intestinal lumen, oxygen bubbles formed and the intestinal wall rapidly turned to a light yellow-brown color, indicating the rapid diffusion of hydrogen peroxide and initiation of polydopamine polymerization. Second, increasing amounts of oxygen bubbles were generated at the epithelium-solution interface (camera inside view) and released into the solution (camera outside view), confirming the rapid decomposition of hydrogen peroxide and providing evidence for the mechanism of oxygen release. Third, the interfacial oxygen catalyzed polydopamine polymerization and adhesion to intestinal epithelium, whereas the tissue-accelerated polymerization solution remained in a liquid state and the intestinal lumen remained expanded, alleviating concerns about bowel adhesion and obstructions. The results show that after coating, the solution inside the lumen also turned a dark-brown color, likely due to the diffusion of unbound polydopamine into the solution.

To directly evaluate coating formation, a laparotomy was performed on the pig. A non-crushing clamp was applied at the small intestine before endoscopic administration of the tissue-accelerated polymerization solution into the intestine. As shown in FIG. 3D, the tissue-accelerated polymerization solution filled the intestinal cavity up until the clamp site, unable to pass down to the lower small intestine. The tissue nearby the clamp was isolated, washed, and opened up. Different polydopamine coating results were observed before and after the clamp site. Compared to the control segment after the clamp site, the tissue submerged in the tissue-accelerated polymerization solution showed enhanced polydopamine coating density, confirming the remarkable tissue-coating performance of tissue-accelerated polymerization in vivo.

Next, whether the tissue-accelerated polymerization technology can enable safe and prolonged intestinal retention was investigated. Polydopamine shedding from epithelium was endoscopically visualized after 24 hours, indicating that the coating is transient. However, considering the inconveniences of endoscopic procedures, incompatibilities of frequent sedation, and the uncertainties of the solution remaining in the field of endoscopic imaging, a more ergonomic method is needed to monitor the intestinal retention of polydopamine. X-ray imaging is a convenient and effective tool, commonly used for examination of the digestive tract[19]. To apply X-ray imaging to this study, modified conventional X-ray contrast agents by encapsulating radio-opaque particles in polydopamine were used (FIG. 15A). These polydopamine-probes suspended in the tissue-accelerated polymerization solution were co-coated with polydopamine on intestinal epithelium, and incorporated into the polydopamine coating layer, which was enabled by the chemical crosslinking between reactive polydopamine on the probe surface and dopamine monomers or oligomers in the tissue-accelerated polymerization solution (FIG. 3E)[14]. This co-coating performance was first characterized through ex vivo studies (FIGS. 15B and 15C), where the coated polydopamine-probes were easily visualized through X-ray imaging, and no signal decay was observed after rinsing the epithelial surface with water, demonstrating the stability of polydopamine-probe coating. In contrast, no obvious X-ray signal was detected in control experiments where conventional probes or polydopamine alone were applied for coating. The polydopamine-probes showed their potential use for in vivo imaging of the intestinal retention of the polydopamine coating layer. When the polydopamine-probe suspended tissue-accelerated polymerization solution was administered to healthy pigs, following clinical procedures for the barium meal test, X-ray signal enhancement was observed in the small intestine (FIG. 16A), revealing the shape of the bowel. However, when conventional probes of equal concentration were administered to the pigs, the resulting small intestine X-ray signal was weak in comparison. It is also worth mentioning that, after rinsing the imaging area, signals of conventional probes were barely detectable, while polydopamine-probes were still clearly visualized (FIG. 3G), with a 8.9 fold signal intensity difference between the two types of probes (FIG. 3H), demonstrating the efficient incorporation of polydopamine-probes as well as the stable coating of polydopamine on the tissue. To monitor the intestinal retention of polydopamine over time, a series of X-ray images were periodically taken in the same location (FIG. 3G and FIG.16B). Animals consistently consumed a liquid diet during imaging, mimicking realistic conditions and testing the stability of the polydopamine coating in the presence of food. A quantitative signal intensity analysis was performed on the small intestine and surrounding tissues (FIG. 3I). When conventional probes were administered to the pigs, the X-ray signal in the small intestine was hardly detected after rinsing and exposure to food for 2-24 hours, due to the relatively weak tissue-adhesion causing quick elimination of the probes. However, when polydopamine-probes were administered for imaging, distinct X-ray signals were observed in the small intestine after food exposure for 2 hours, only decreasing 28% at the sixth hour, showing the prolonged intestinal retention of the polydopamine coating. The polydopamine signal reduction is likely due to the fast renewal of the intestinal mucus through goblet cell secretion ~12-24 hours), and frequent turnover of epithelial cells through stem cell proliferation (~1-5 day)[20], where the polymeric coating layer, as well as epithelium underneath the polydopamine, is shed off into lumen. Notably, the intestinal X-ray signal dropped back to the pre-administration level after 24 hours, indicating complete elimination and transient residence of the polydopamine coating layer. This confirmation of the transient properties of the polydopamine coating is indicative of the safety of the tissue-accelerated polymerization technology.

EXAMPLE 4

Tissue-Accelerated Polymerization for Regulation of Enzymatic Digestion

To demonstrate the versatility of the tissue-accelerated polymerization technology, the therapeutic value of the technology in regulation of enzymatic digestion was evaluated (FIG. 4A). Polydopamine is highly reactive with many chemical groups, such as amine, phenol, and sulfhydryl groups, enabling the facile incorporation of functional agents into the polydopamine coating layer[14]. A digestive enzyme was accordingly incorporated into the tissue-accelerated polymerization system.

The tissue-accelerated polymerization technology was utilized to improve digestion efficiency by incorporating digestive enzymes into polydopamine coating layer on small intestinal epithelium (FIG. 4B). According to recent studies, around 70% of the world population has hypolactasia, referring to the low levels or absence of lactase, causing lactose intolerance[21,22]. If the tissue-accelerated polymerization technology was utilized to coat exogenous β-galactosidase on intestinal epithelium, it would augment the digestion of lactose in the small intestine. Restoring function of intestinal brush border enzymes, particularly β-galactosidase, enables treatment for digestive disorders and diseases, improving patient prognosis and quality of life[23,24].

To demonstrate the ability of the tissue-accelerated polymerization technology to improve lactose digestion, the tissue-accelerated polymerization solution with suspended β-galactosidase was used to coat the small intestine of a sedated pig, where a laparotomy was performed to provide access to the small intestinal mucosa. The β-galactosidase activity of the coated epithelium was then evaluated after rinsing. The coating efficiency was confirmed through the analysis of β-galactosidase activity with and without the agents (β-galactosidase and tissue-accelerated polymerization solution). As shown in FIG. 4C, quantitative comparison of β-galactosidase activity indicated an approximately 20-fold increase in digestion efficiency upon the addition of the tissue-accelerated polymerization-based β-galactosidase coating to the porcine small intestine. In contrast, no enhancements of β-galactosidase activity were detected in control groups (without β-galactosidase, without tissue-accelerated polymerization solution or without both), confirming that the β-galactosidase activity increase was due to its pairing with the tissue-accelerated polymerization technology. Additionally, when only the tissue-accelerated polymerization solution was administered, no reduction of digestive enzyme activity was observed compared to uncoated tissues. This consistent baseline enzymatic activity indicates that neither the coating chemistry (the crosslinking between polydopamine and epithetical biomolecules), nor the coated polydopamine itself inhibited the intrinsic digestive enzyme activity of epithelium, demonstrating the permeability of the polydopamine coating in the small intestine to allow molecules to pass through by diffusion. The tissue-accelerated polymerization technology opens a new avenue to augment digestive efficiency in the small intestine and a promising mechanism to treat digestive disorders and diseases.

EXAMPLE 5

Tissue-Accelerated Polymerization for Regulation of Nutrient Absorption

The therapeutic value of the technology in regulation of nutrient absorption was also evaluated (FIG. 4A). Polydopamine is highly reactive with many chemical groups, such as amine, phenol, and sulfhydryl groups, enabling the facile incorporation of functional agents into the polydopamine coating layer[14]. A nutrient blocker was accordingly incorporated into the tissue-accelerated polymerization system to develop an impermeable barrier to regulate nutrient absorption.

Glucose absorption in the small intestine plays a role in the regulation of plasma glucose levels, which are frequently associated with metabolic disorders and systemic diseases, such as obesity, hyperinsulinemia, and diabetes mellitus[25]. To prevent excessive glucose intake in patients with these diseases and disorders, treatments such as gastric bypass surgery, intestinal sleeve placement, surgical adhesives, and gastrointestinal electrical stimulation have been tested[3,7,26,27]. However, these procedures are invasive and target the entire gastrointestinal tract, posing limitations for broad adoption. The tissue-accelerated polymerization technology offers a non-invasive, tissue-targeted method for regulating glucose absorption. The power of tissue-accelerated polymerization technology in isolation from nutrient exposure, especially glucose absorption, in the small intestine was demonstrated.

To provide a barrier to prevent glucose uptake, the small intestinal epithelium was coated with an impermeable polydopamine coating layer using this technology (FIG. 4D). Nano-crosslinkers were added to the tissue-accelerated polymerization solution to produce a highly crosslinked polydopamine coating layer with ultralow permeability. As shown in FIGS. 17A-17B, the additional nano-crosslinkers are about 527 nm in diameter with a uniform size distribution. These hydrophilic nano-crosslinkers suspended in the tissue-accelerated polymerization solution were thereby incorporated into the polydopamine coating layer, which was enabled by the chemical crosslinking between reactive catechol and amine groups exposed on the surface of nano-crosslinkers and dopamine monomers or oligomers in the tissue-accelerated polymerization solution. Thus, the incorporation of crosslinkers increases the number of covalent bonds inside the polydopamine coating, enabling a highly compact polydopamine coating layer with low permeability. To validate the nutrient-regulating function, tissue-accelerated polymerization solution with suspended nano-crosslinkers was endoscopically administered to pigs. Following tissue-accelerated polymerization coating, oral glucose was administered to the pigs, followed by a standard oral glucose tolerance test (OGTT). Blood glucose levels were monitored to quantify the intestinal glucose absorption. As shown in FIG. 4E, control pigs, without the tissue-accelerated polymerization coating, had blood glucose levels increase dramatically after oral glucose administration. However, animals treated with the tissue-accelerated polymerization solution showed reduced blood glucose responses. Quantitative comparison of blood glucose levels for samples from pigs with and without the tissue-accelerated polymerization coating showed an average of 73.3% reduction of glucose levels in the tissue-accelerated polymerization coating over controls, where six individual experiments on six different pigs were performed and analyzed. This reduction in glucose response demonstrated the ability of tissue-accelerated polymerization technology to effectively prevent postprandial glucose intake. Additionally, the tissue-accelerated polymerization barrier showed efficient blocking abilities of different nutrients, and the blocking efficiency was modulated by tuning the crosslinking density of the tissue-accelerated polymerization coating layer (FIGS. 32A-32D). Furthermore, it was confirmed that the glucose absorption barrier is transient, with normal glucose absorption being restored after 24 hours (FIG. 33). These results address the clinical need of non-invasively blocking glucose absorption in the small intestine, proving the feasibility of tissue-accelerated polymerization technology as a therapeutic approach for patients with type 2 diabetes mellitus.

EXAMPLE 6

Tissue-Accelerated Polymerization for Regulation of Drug Release

The therapeutic value of the technology in regulation of drug release was also evaluated (FIG. 4A). Polydopamine is highly reactive with many chemical groups, such as amine, phenol, and sulfhydryl groups, enabling the facile incorporation of functional agents into the polydopamine coating layer[14]. An Anthelmintic drug was accordingly incorporated into the tissue-accelerated polymerization system to evaluate the system as used for oral drug delivery, demonstrating its ability for sustained release of therapeutics in the small intestine.

The development of oral sustained-release drugs is restricted by the rapid transit time of therapeutics in the gastrointestinal tract. Attempts have been made to prolong the gastrointestinal residence of drugs, especially in the small intestine, a more compatible environment for sensitive pharmaceuticals compared to the harsh acidity of the stomach, with little success[19,28]. Praziquantel was chosen as the model drug to test the ability of tissue-accelerated polymerization technology to prolong intestinal residence. Praziquantel is the only anthelmintic drug frequently used to treat schistosomiasis, a major neglected tropical disease caused by parasitic worms, affecting over 200 million people worldwide[29,30]. Praziquantel, with a half-life of 1 to 1.5 hours in humans, is recommended to be taken orally 3 times per day with a 5-hour interval requirement, a difficult regiment to adhere to. An alternate technology capable of prolonging intestinal retention to reduce dosing frequency is urgently needed.

As shown in FIG. 4F, praziquantel particles (powder) were coated on small intestinal epithelium using tissue-accelerated polymerization technology, enabling its prolonged intestinal residence and sustained release. The praziquantel particles (powder) were encapsulated in polydopamine to incorporate the drug into the polydopamine coating layer. Pharmacokinetics studies were carried out for a single oral administration of the praziquantel-tissue-accelerated polymerization solution in pigs to investigate the release kinetics of the praziquantel-tissue-accelerated polymerization solution. After administration, blood samples were collected at 0, 1, 2, 3, 4, 5, 6, 24, and 48 hours, which were further analyzed by liquid chromatography-tandem mass spectroscopy for serum praziquantel concentration. Quantitative comparison of the pharmacokinetics, shown in FIG. 4G, revealed that the retention time of the praziquantel with the tissue-accelerated polymerization solution was extended relative to the conventionally administration. When the praziquantel control (without the tissue-accelerated polymerization solution) was administered conventionally, the drug was rapidly cleared from blood with an elimination phase of 2-6 hours, and no drug was detected at or after 24 hours. However, blood levels of praziquantel administered through the tissue-accelerated polymerization technology sustained for more than 6 hours, with an average concentration of 20.0 ng mL$^{-1}$ still detectable at 24 hours, higher than even the average control drug concentrations (15.1 ng mL$^{-1}$) at 6 hours. Quantitative analysis of pharmacokinetic parameters, including area under the curve (AUC) and half-life, was conducted using a non-compartment pharmacokinetics model. Results from 3 large-animal studies showed a 4-fold increase between the AUC values of the praziquantel (905.8 ng h mL$^{-1}$, with the tissue-accelerated polymerization solution) and praziquantel control (222.4 ng h mL$^{-1}$). Additionally, the half-life of praziquantel increased by 10 fold (from 1.3 hours to 13 hours) when administered using the tissue-accelerated polymerization technology, demonstrating the prolonged intestinal residence of the drug. Notably, praziquantel is primarily metabolized by cytochrome P450 enzymes, specially CYP3A4 present in the small intestine and liver[30,38]. To confirm that the tissue-accelerated polymerization coating did not affect the drug metabolism, the CYP3A4 activity of epithelium with and without the polydopamine coating layer were measured and compared (FIG. 34), and no change in CYP3A4 activity was observed after the tissue-accelerated polymerization coating. The sustained-release of praziquantel through the tissue-accelerated polymerization technology expands the effectiveness of treatment options for schistosomiasis and is also applicable to diseases where regimented adherence is important for efficacy.

EXAMPLE 7

Ultrafast and Stable Coating of Human Tissue Using Tissue-Accelerated Polymerization The tissue-accelerated polymerization technology is applicable in human tissues and suitable for clinical translation. Fresh resected tissue specimens from human small intestine were coated to test for compatibility with the tissue-accelerated polymerization technology. Similar to porcine tissue-coating results (FIG. 1E), polydopamine coating was clearly observed on the human small intestinal surface (FIG. 5A). However, polydopamine signals developed more quickly in human tissues compared to porcine tissues, with coating completion time decreasing from 12 to 3 minutes (FIG. 5B), likely due to higher levels of catalase in the human small intestine. The relationship between small intestinal catalase activity and tissue-accelerated polymerization coating density was analyzed using human, porcine, and murine tissue specimens, resulting in a clear correlation between tissue-accelerated polymerization coating density and enzymatic activity levels (FIGS. 18A-18B). The human and porcine small intestines exhibited 60% more polydopamine development compared to the murine small intestine, due to their strong enzymatic activity. The similar tissue-accelerated polymerization efficiency (between humans and pigs) likely resulted from their genome and proteome similarities. To further demonstrate the robustness of the tissue-accelerated polymerization technology for human tissue coating, tissue specimens from 3 donors were tested with the polydopamine coating. Additionally, five assessments were performed on random sites of the small intestine (from donors with different age, race and gender) to confirm consistent polydopamine coating performance. Additionally, it was confirmed that the human and porcine GI tracts exhibit similar tissue-accelerated polymerization pattern (FIGS. 35A-35B), due to higher expression of catalase in the small intestine of both species as compared to other segments of the GI tract[15]. As shown in FIG. 5C, 30 images of tissue (6 mm in diameter) revealed highly consistent polydopamine coating with signal enhancement. These tissue specimens, coated through the tissue-accelerated polymerization technology, were further examined microscopically. Consistent with the porcine results (FIG. 2G), microscopic and histological analyses of frozen and formalin-fixed paraffin-embedded (FFPE) specimens show a thin layer of the polydopamine coating on the exterior villi of human small intestine (FIG. 5D). After exposure to the tissue-accelerated polymerization solution, the epithelial layers remained intact, with staining patterns similar to the unexposed controls, demonstrating the absence of tissue toxicity.

To further evaluate the biocompatibility of the tissue-accelerated polymerization technology, the cytotoxicity of polydopamine on multiple cell lines was characterized: HeLa, COLO320DM, Caco-2, Hep3B, and HS 895.T (FIG. 19), resulting in no significant cytotoxicity observed after 6-48 hour in vitro incubation. Furthermore, the oral toxicity of the tissue-accelerated polymerization solution was systematically assessed by following guidelines issued by OECD with minor modifications. Accordingly, rats were exposed to the tissue-accelerated polymerization solution over a period of 4 weeks, based on the repeated dose 28-day toxicity study method recommended by Good Laboratory Practice (GLP). During the 28-day exposure period, no significant differences in body weights were observed between rats exposed to the tissue-accelerated polymerization solution and controls (FIGS. 20A-20C). Additional hematological measurements, blood biochemistry tests (FIGS. 21 and 22), and histopathological examinations further confirmed the absence of oral toxicity (FIG. 23), supporting the favorable biocompatibility of the tissue-accelerated polymerization technology, indicative of a minimized risk for forthcoming preclinical and clinical trials.

Human tissue-coating stability is a factor for clinical translation of the tissue-accelerated polymerization technology. The small intestine provides a dynamic environment, where physical forces (peristalsis and segmentation) and chemical exposures (chyme, gastric acid and intestinal fluid) have potential to damage the polydopamine coating (FIG. 36A-36C). To evaluate the stability of the tissue coating, in a series of physical and chemical conditions. As shown in FIG. 5E, no polydopamine signal reduction was observed under mechanical stirring and scratching. Quantitative signal intensity analysis showed that approximately 80% polydopamine still remained strongly attached even after vigorous scratching of the small intestine using the spine of a scalpel (FIG. 5F). In addition, the stability of the polydopamine coating was further confirmed by incubating polydopamine coated human tissue in different solutions for 24 hours. As shown in FIG. 5G, the polydopamine coating layer was highly stable in simulated intestinal and gastric fluid, and other extreme conditions (ethanol and concentrated saline). These results confirm the coating stability of the tissue-accelerated polymerization technology in the human small intestine and demonstrating feasibility for wide applicability.

REFERENCES

1. Anselmo, A. C., Gokarn, Y. & Mitragotri, S. Non-invasive delivery strategies for biologics. Nat. Rev. Drug Discov. 18, 19-40 (2018).
2. Zelikin, A. N., Ehrhardt, C. & Healy, A. M. Materials and methods for delivery of biological drugs. Nat. Chem. 8, 997-1007 (2016).
3. Lee, Y. et al. Therapeutic luminal coating of the intestine. Nat. Mater. 17, 834-842 (2018).
4. Yui, S. et al. Functional engraftment of colon epithelium expanded in vitro from a single adult Lgr5+ stem cell. Nat. Med. 18, 618-623 (2012).
5. Kitano, K. et al. Bioengineering of functional human induced pluripotent stem cell-derived intestinal grafts. Nat. Commun. 8, 765 (2017).
6. Elloumi-Hannachi, I., Yamato, M. & Okano, T. Cell sheet engineering: a unique nanotechnology for scaffold-free tissue reconstruction with clinical applications in regenerative medicine. J. Intern. Med. 267, 54-70 (2010).
7. Mohanaruban, A. et al. PTH-003 Endobarrier®: a safe and effective novel treatment for obesity and type 2 diabetes? in Endoscopy 66, A205.1-A205 (2017).
8. Fishbein, T. M. Intestinal Transplantation. N. Engl. J. Med. 361, 998-1008 (2009).
9. Khademhosseini, A. & Langer, R. A decade of progress in tissue engineering. Nat. Protoc. 11, 1775-1781 (2016).
10. Odenwald, M. A. & Turner, J. R. The intestinal epithelial barrier: a therapeutic target? Nat. Rev. Gastroenterol. Hepatol. 14, 9-21 (2017).
11. Lee, H., Dellatore, S. M., Miller, W. M. & Messersmith, P. B. Mussel-inspired surface chemistry for multifunctional coatings. Science 318, 426-30 (2007).
12. Kirkman, H. N. & Gaetani, G. F. Mammalian catalase: a venerable enzyme with new mysteries. Trends Biochem. Sci. 32, 44-50 (2007).
13. Ofikwu, G. I., Sarhan, M. & Ahmed, L. EVICEL glue-induced small bowel obstruction after laparoscopic gastric bypass. Surg. Laparosc. Endosc. Percutan. Tech. 23, e38-40 (2013).
14. Lee, H., Rho, J. & Messersmith, P. B. Facile Conjugation of Biomolecules onto Surfaces via Mussel Adhesive Protein Inspired Coatings. Adv. Mater. 21, 431-434 (2009).
15. Fagerberg, L. et al. Analysis of the Human Tissue-specific Expression by Genome-wide Integration of Transcriptomics and Antibody-based Proteomics. Mol. Cell. Proteomics 13, 397 (2014).
16. Li, J. et al. Dramatic enhancement of the detection limits of bioassays via ultrafast deposition of polydopamine. Nat. Biomed. Eng. 1, 0082 (2017).
17. Connock, M. & Pover, W. Catalase particles in the epithelial cells of the guinea-pig small intestine. Histochem. J. 2, 371-380 (1970).
18. Traverso, G. & Langer, R. Perspective: Special delivery for the gut. Nature 519, S19-S19 (2015).
19. Bellinger, A. M. et al. Oral, ultra-long-lasting drug delivery: Application toward malaria elimination goals. Sci. Transl. Med. 8, 365ra157 (2016).
20. Barker, N. Adult intestinal stem cells: critical drivers of epithelial homeostasis and regeneration. Nat. Rev. Mol. Cell Biol. 15, 19-33 (2014).
21. Lomer, M. C. E., Parkes, G. C. & Sanderson, J. D. Review article: lactose intolerance in clinical practice—myths and realities. Aliment. Pharmacol. Ther. 27, 93-103 (2007).
22. Storhaug, C. L., Fosse, S. K. & Fadnes, L. T. Country, regional, and global estimates for lactose malabsorption in adults: a systematic review and meta-analysis. Lancet Gastroenterol. Hepatol. 2, 738-746 (2017).
23. Rosado, J. L. et al. Enzyme Replacement Therapy for Primary Adult Lactase Deficiency: Effective Reduction of Lactose Malabsorption and Milk Intolerance by Direct Addition of β-Galactosidase to Milk at Mealtime. Gastroenterology 87, 1072-1082 (1984).
24. Leader, B., Baca, Q. J. & Golan, D. E. Protein therapeutics: a summary and pharmacological classification. Nat. Rev. Drug Discov. 7, 21-39 (2008).
25. American Diabetes Association, A. D. 2. Classification and Diagnosis of Diabetes: Standards of Medical Care in Diabetes-2018. Diabetes Care 41, S13-S27 (2018).
26. Mingrone, G. et al. Bariatric Surgery versus Conventional Medical Therapy for Type 2 Diabetes. N. Engl. J. Med. 366, 1577-1585 (2012).
27. Lin, Z., Forster, J., Sarosiek, I. & McCallum, R. W. Treatment of Diabetic Gastroparesis by High-Frequency Gastric Electrical Stimulation. Diabetes Care 27, 1071-1076 (2004).
28. Liu, J. et al. Triggerable tough hydrogels for gastric resident dosage forms. Nat. Commun. 8, 124 (2017).
29. Doenhoff, M. J., Cioli, D. & Utzinger, J. Praziquantel: mechanisms of action, resistance and new derivatives for schistosomiasis. Curr. Opin. Infect. Dis. 21, 659-667 (2008).

30. Vale, N. et al. Praziquantel for Schistosomiasis: Single-Drug Metabolism Revisited, Mode of Action, and Resistance. Antimicrob. Agents Chemother. 61, e02582-16 (2017).
31. Turner, J. R. Intestinal mucosal barrier function in health and disease. Nat. Rev. Immunol. 9, 799-809 (2009).
32. Peterson, L. W. & Artis, D. Intestinal epithelial cells: regulators of barrier function and immune homeostasis. Nat. Rev. Immunol. 14, 141-153 (2014).
33. U.S. Pat. No. 7,025,791
34. U.S. Pat. No. 8,4145,59
35. U.S. Pat. No. 9,707,070
36. U.S. Pat. No. 7,335,210
37. Heber, D. et al. Endocrine and nutritional management of the post-bariatric surgery patient: An endocrine society clinical practice guideline. J. Clin. Endocrinol. Metab. 95, 4823-4843 (2010).
38. Thelen, K. & Dressman, J. B. Cytochrome P450-mediated metabolism in the human gut wall. J. Pharm. Pharmacol. 61, 541-558 (2009).
39. Holmes, J. C. & Fowler, N. O. Direct cardiac effects of dopamine. Circ. Res. 10, 68-72 (1962).
40. A. Abramson, E. Caffarel-Salvador, V. Soares, D. Minahan, R. Y. Tian, X. Lu, D. Dellal, Y. Gao, S. Kim, J. Wainer, J. Collins, S. Tamang, A. Hayward, T. Yoshitake, H. C. Lee, J. Fujimoto, J. Fels, M. R. Frederiksen, U. Rahbek, N. Roxhed, R. Langer, G. Traverso, A luminal unfolding microneedle injector for oral delivery of macromolecules, Nat. Med. 25, 1512-1518 (2019).
41. A. R. Kirtane, T. Hua, A. Hayward, A. Bajpayee, A. Wahane, A. Lopes, T. Bensel, L. Ma, F. Z. Stanczyk, S. Brooks, D. Gwynne, J. Wainer, J. Collins, S. M. Tamang, R. Langer, G. Traverso, A once-a-month oral contraceptive, Sci. Transl. Med. 11, eaay2602 (2019).
42. A. Y. Abuhelwa, D. J. R. Foster, R. N. Upton, A quantitative review and meta-models of the variability and factors affecting oral drug absorption—part I: gastrointestinal pH, AAPS J. 18, 1309-1321 (2016).
43. B. Laulicht, A. Tripathi, E. Mathiowitz, Diuretic bioactivity optimization of furosemide in rats, Eur. J. Pharm. Biopharm. 79, 314-319 (2011).
44. C. Camaschella, Iron-deficiency anemia, N. Engl. J. Med. 372, 1832-1843 (2015).
45. E. Manell, P. Hedenqvist, A. Svensson, M. Jensen-Waern, E. Xu, Ed. Establishment of a refined oral glucose tolerance test in pigs, and assessment of insulin, glucagon and glucagon-like peptide-1 responses, PLoS One 11, e0148896 (2016).
46. E. Margoliash, A. Margoliash, A study of the inhibition of catalase by 3-amino-1:2:4:-triazole, Biochem. J. 68, 468-475 (1958).
47. F. C. Harris, Pyloric stenosis: hold-up of enteric coated aspirin tablets, Br. J. Surg. 60, 979-981 (1973).
48. F. Ponzio, V. Le Houerou, S. Zafeiratos, C. Gauthier, T. Gamier, L. Jierry, V. Ball, Robust alginate-catechol@polydopamine free-standing membranes obtained from the water/air interface, Langmuir 33,2420-2426 (2017).
49. G. P. Carino, E. Mathiowitz, Oral insulin delivery, Adv. Drug Deliv. Rev. 35,249-257 (1999).
50. H. Rajagopalan, A. C. Cherrington, C. C. Thompson, L. M. Kaplan, F. Rubino, G. Mingrone, P. Becerra, P. Rodriguez, P. Vignolo, J. Caplan, L. Rodriguez, M. P. Galvao Neto, Endoscopic duodenal mucosal resurfacing for the treatment of type 2 diabetes: 6-month interim analysis from the first-in-human proof-of-concept study., Diabetes Care 39,2254-2261 (2016).
51. H. Zhan, T. Jagtiani, J. F. Liang, A new targeted delivery approach by functionalizing drug nanocrystals through polydopamine coating, Eur. J. Pharm. Biopharm. 114, 221-229 (2017).
52. J. Cui, Y. Wang, A. Postma, J. Hao, L. Hosta-Rigau, F. Caruso, Monodisperse polymer capsules: tailoring size, shell thickness, and hydrophobic cargo loading via emulsion templating, Adv. Funct. Mater. 20,1625-1631 (2010).
53. J. Dressman, J. Kramer, Pharmaceutical dissolution testing (Taylor & Francis, 2005).
54. J. Park, T. F. Brust, H. J. Lee, S. C. Lee, V. J. Watts, Y. Yeo, Polydopamine-based simple and versatile surface modification of polymeric nano drug carriers, ACS Nano 8, 3347-3356 (2014).
55. J. Tones, S. Mehandru, J.-F. Colombel, L. Peyrin-Biroulet, Crohn's disease, Lancet 389,1741-1755 (2017).
56. M. Bisaglia, S. Mammi, L. Bubacco, Kinetic and structural analysis of the early oxidation products of dopamine: analysis of the interactions with a-synuclein, J. Biol. Chem. 282,15597-15605 (2007).
57. M. Z. I. Khan, . Prebeg, N. Kurjakovié, A pH-dependent colon targeted oral drug delivery system using methacrylic acid copolymers. I. Manipulation of drug release using Eudragit® L100-55 and Eudragit® S100 combinations, J. Control. Release 58, 215-222 (1999).
58. OECD, Test no. 407: repeated dose 28-day oral toxicity study in rodentsOECD Guidel. Test. Chem. Sect. 4, OECD Publ. Paris , 1-10 (2008).
59. P. H. R. Green, C. Cellier, Celiac disease, N. Engl. J. Med. 357,1731-1743 (2007).
60. P. Kirkegaard, A. B. Christensen, J. Ibsen, V. Hegedus, J. Christiansen, Experimental nonsuture colonic anastomoses, Am. J. Surg. 139, 233-236 (1980).
61. P. Winterwerber, S. Harvey, D. Y. W. Ng, T. Weil, Photocontrolled dopamine polymerization on DNA origami with nanometer resolution, Angew. Chemie Int. Ed. 59, 6144-6149 (2020).
62. S. Babaee, S. Pajovic, A. R. Kirtane, J. Shi, E. Caffarel-Salvador, K. Hess, J. E. Collins, S. Tamang, A. V. Wahane, A. M. Hayward, H. Mazdiyasni, R. Langer, G. Traverso, Temperature-responsive biometamaterials for gastrointestinal applications, Sci. Transl. Med. 11, eaau8581 (2019).
63. S. Hong, Y. Wang, S. Y. Park, H. Lee, Progressive fuzzy cation-assembly of biological catecholamines, Sci. Adv. 4, eaat7457 (2018).
64. S. Thakral, N. K. Thakral, D. K. Majumdar, Eudragit®: a technology evaluation, Expert Opin. Drug Deliv. 10, 131-149 (2013).
65. U.S. Food and Drug Administration, Oral health care drug products for over-the-counter human use; antigingivitis/antiplaque drug products; establishment of a monograph; proposed rules, Fed. Regist. 68, 32232-32287 (2003).
66. V. Ball, D. Del Frari, V. Toniazzo, D. Ruch, Kinetics of polydopamine film deposition as a function of pH and dopamine concentration: Insights in the polydopamine deposition mechanism, J. Colloid Interface Sci. 386, 366-372 (2012).
67. Y. Tokura, S. Harvey, C. Chen, Y. Wu, D. Y. W. Ng, T. Weil, Fabrication of defined polydopamine nanostructures by DNA origami-templated polymerization, Angew. Chemie Int. Ed. 57, 1587-1591 (2018).
68. Candi, E., Schmidt, R. & Melino, G. The cornified envelope: A model of cell death in the skin. Nat. Rev. Mol. Cell Biol. 6, 328-340 (2005).
69. Lambrecht, B. N. & Hammad, H. The airway epithelium in asthma. Nat. Med. 18, 684-692 (2012).

70. Obermeier, B., Daneman, R. & Ransohoff, R. M. Development, maintenance and disruption of the blood-brain barrier. *Nature Medicine* vol. 19 1584-1596 (2013).
71. Zihni, C., Mills, C., Matter, K. & Balda, M. S. Tight junctions: From simple barriers to multifunctional molecular gates. *Nat. Rev. Mol. Cell Biol.* 17, 564-580 (2016).
72. Varga, Z. et al. Endothelial cell infection and endotheliitis in COVID-19. *Lancet* 395, 1417-1418 (2020).
73. Richard, M. et al. Influenza A viruses are transmitted via the air from the nasal respiratory epithelium of ferrets. *Nat. Commun.* 11, 1-11 (2020).
74. Nishida, K. et al. Corneal reconstruction with tissue-engineered cell sheets composed of autologous oral mucosal epithelium. *N. Engl. J. Med.* 351, 1187-1196 (2004).
75. Gallico, G. G., O'Connor, N. E., Compton, C. C., Kehinde, O. & Green, H. Permanent coverage of large burn wounds with autologous cultured human epithelium. *N. Engl. J. Med.* 311, 448-451 (1984).
76. Sweeney, M. D., Sagare, A. P. & Zlokovic, B. V. Blood-brain barrier breakdown in Alzheimer disease and other neurodegenerative disorders. *Nat. Rev. Neurol.* 14, 133-150 (2018).
77. Sun, Y. et al. Inhibition of autophagy ameliorates acute lung injury caused by avian influenza A H5N1 infection. *Sci. Signal.* 5, ra16-ra16 (2012).
78. Vacanti, J. P. & Langer, R. Tissue engineering: The design and fabrication of living replacement devices for surgical reconstruction and transplantation. *Lancet* 354, 32-34 (1999).
79. Freedman, B. R. & Mooney, D. J. Biomaterials to mimic and heal connective tissues. *Adv. Mater.* 31, (2019).
80. Taboada, G. M. et al. Overcoming the translational barriers of tissue adhesives. *Nat. Rev. Mater.* 5, 310-329 (2020).
81. Li, J. et al. Gastrointestinal synthetic epithelial linings. *Sci. Transl. Med.* 12, 441 (2020).
82. Azari, A. A. & Barney, N. P. Conjunctivitis: A systematic review of diagnosis and treatment. *JAMA—Journal of the American Medical Association* vol. 310 1721-1729 (2013).
83. FDA. MAXIDEX®-dexamethasone ophthalmic suspension Label. *FDA, US.* (2019).
84. Kersey, J. P. & Broadway, D. C. Corticosteroid-induced glaucoma: A review of the literature. *Eye* vol. 20 407-416 (2006).
85. Sonis, S. T. The pathobiology of mucositis. *Nat. Rev. Cancer* 4, 277-284 (2004).
86. Scully, C. Aphthous Ulceration. *N. Engl. J. Med.* 355, 165-172 (2006).
87. Vera-Llonch, M., Oster, G., Hagiwara, M. & Sonis, S. Oral mucositis in patients undergoing radiation treatment for head and neck carcinoma: Risk factors and clinical consequences. *Cancer* 106, 329-336 (2006).
88. Lanas, A. et al. Non-variceal upper gastrointestinal bleeding. *Nat. Rev. Dis. Prim.* 4, 18020 (2018).
89. Laine, L. Upper Gastrointestinal Bleeding Due to a Peptic Ulcer. *N. Engl. J. Med.* 374, 2367-2376 (2016).
90. Gralnek, I. M., Barkun, A. N. & Bardou, M. Management of acute bleeding from a peptic ulcer. *N. Engl. J. Med.* 359, 928-937 (2008).
91. Barkun, A. N., Moosavi, S. & Martel, M. Topical hemostatic agents: A systematic review with particular emphasis on endoscopic application in GI bleeding. *Gastrointest. Endosc.* 77, 692-700 (2013).
92. Chahal, D., Lee, J. G. H., Ali-Mohamad, N. & Donnellan, F. High rate of re-bleeding after application of Hemospray for upper and lower gastrointestinal bleeds. *Dig. Liver Dis.* 52, 768-772 (2020).
93. Godin, D. V. & Garnett, M. E. Species-related variations in tissue antioxidant status-I. Differences in antioxidant enzyme profiles. *Comp. Biochem. Physiol.-Part B Biochem. Mol. Biol.* 103, 737-742 (1992).
94. Maier, G. P., Rapp, M. V., Waite, J. H., Israelachvili, J. N. & Butler, A. Adaptive synergy between catechol and lysine promotes wet adhesion by surface salt displacement. *Science* (80-.). 349, 628-632 (2015).
95. Lavker, R. M. & Sun, T. T. Epithelial stem cells: The eye provides a vision. *Eye* 17, 937-942 (2003).
96. Gipson, I. K. Goblet cells of the conjunctiva: A review of recent findings. *Progress in Retinal and Eye Research* vol. 54 49-63 (2016).
97. Yuk, H. et al. Dry double-sided tape for adhesion of wet tissues and devices. *Nature* (2019) doi:10.1038/s41586-019-1710-5.
98. Squier, C. & Brogden, K. A. *Human Oral Mucosa: Development, Structure and Function.* John Wiley & Sons (2010).
99. Gerber, D. E. & Chan, T. A. Recent Advances in Radiation Therapy. *Am. Fam. Physician* 78, 1254-1262 (2008).
100. Goyal, M. M. & Basak, A. Human catalase: Looking for complete identity. *Protein Cell* 1, 888-897 (2010).
101. Forrest, J. A. H., Finlayson, N. D. C. & Shearman, D. J. C. Endoscopy in gastrointestinal bleeding. *Lancet* 304, 394-397 (1974).
102. Sáenz, J. B. & Mills, J. C. Acid and the basis for cellular plasticity and reprogramming in gastric repair and cancer. *Nat. Rev. Gastroenterol. Hepatol.* 15, 257-273 (2018).
103. Arakawa, T. et al. Quality of ulcer healing in gastrointestinal tract: Its pathophysiology and clinical relevance. *World J. Gastroenterol.* 18, 4811-4822 (2012).
104. Xu, X. et al. Bioadhesive hydrogels demonstrating pH-independent and ultrafast gelation promote gastric ulcer healing in pigs. *Sci. Transl. Med.* 12, (2020).
105. Andrews, F. M. et al. Comparison of endoscopic, necropsy and histology scoring of equine gastric ulcers. *Equine Vet. J.* 34, 475-478 (2010).

What is claimed is:

1. A method of forming a dopamine polymer on a surface of a tissue in a subject in need thereof, the method comprising administering to the subject a composition comprising a plurality of molecules of dopamine, or a salt thereof, and at least a minimum amount of an oxygen source to polymerize the dopamine on the surface of the tissue, wherein the administering step delivers the plurality of molecules of dopamine, or a salt thereof and the oxygen source to the tissue of the subject, allowing the oxygen source to contact a catalyst in the tissue of the subject, and wherein the oxygen source reacts with the catalyst in the tissue to release oxygen from the oxygen source, and wherein the oxygen released from the oxygen source polymerizes the plurality of molecules of dopamine, or a salt thereof on the surface of the tissue, thereby forming said dopamine polymer on the surface of said tissue; wherein:
the oxygen source is hydrogen peroxide or urea hydrogen peroxidalk; and the catalyst present in the tissue is catalase or peroxidase.

2. The method of claim 1, wherein the peroxidase is eosinophil peroxidase, lactoperoxidase, or myeloperoxidase.

3. The method of claim 1, wherein the catalyst is a catalase.

4. The method of claim 1, wherein the catalyst is located in the gastrointestinal (GI) tract of the subject.

5. The method of claim 1, wherein the composition further comprises an enzyme, a nutrient blocker, a nutraceutical, a radioprotective agent, an active pharmaceutical ingredient, a diagnostic agent, or a combination thereof.

6. The method of claim 1, wherein the composition is administered orally to the subject.

7. The method of claim 1, wherein the composition comprises about 0.01 to about 50 mg/mL of dopamine.

8. The method of claim 1, wherein the composition comprises about 1 mM to about 30 mM of the oxygen source.

9. The method of claim 1, wherein the composition has a pH of about 7 to about 10.

10. The method of claim 1, wherein the tissue comprises an epithelium and the dopamine polymer forms in contact with the epithelium.

11. The method of claim 5, wherein the composition further comprises an enzyme.

12. The method of claim 11, wherein the enzyme is a digestive enzyme.

13. The method of claim 12, wherein the digestive enzyme is lactase, peptidase, sucrase, maltase, amylase, a lipase, or a protease.

14. The method of claim 1, wherein the composition further comprises an active pharmaceutical ingredient.

15. The method of claim 14, wherein the active pharmaceutical ingredient is praziquantel.

* * * * *